United States Patent [19]

Brinker et al.

[11] Patent Number: 6,020,287
[45] Date of Patent: Feb. 1, 2000

[54] PROCESS AND COMPOSITIONS FOR ENHANCING RELIABILITY OF EXOGENOUS CHEMICAL SUBSTANCES APPLIED TO PLANTS

[75] Inventors: Ronald Joseph Brinker, Ellisville; Jane Laura Gillespie, St. Louis; Peter Joseph Raymond, Wildwood; Joseph Jude Sandbrink, Des Peres; James Michael Warner, Webster Groves; Al Steven Wideman; Daniel Richard Wright, both of St. Louis, all of Mo.

[73] Assignee: Monsanto Company, St. Louis, Mo.

[21] Appl. No.: 09/016,773

[22] Filed: Jan. 30, 1998

Related U.S. Application Data

[60] Provisional application No. 60/034,887, Jan. 31, 1997.

[51] Int. Cl.[7] .............................. A01N 25/00; A01N 57/02
[52] U.S. Cl. ............................................ 504/116; 504/206
[58] Field of Search ..................... 504/206, 116

[56] References Cited

U.S. PATENT DOCUMENTS

| | | | |
|---|---|---|---|
| 3,272,842 | 9/1966 | Easton et al. | 260/326.5 |
| 3,799,758 | 3/1974 | Franz | 71/86 |
| 4,405,531 | 9/1983 | Franz | 260/501.12 |
| 4,436,547 | 3/1984 | Sampson | 71/76 |
| 4,639,538 | 1/1987 | Linares | 558/71 |
| 4,808,208 | 2/1989 | Lee et al. | 71/86 |
| 4,880,624 | 11/1989 | Metcalf et al. | 424/84 |
| 5,006,157 | 4/1991 | Ohba et al. | 71/95 |
| 5,281,571 | 1/1994 | Woodard et al. | 504/225 |
| 5,312,929 | 5/1994 | Ohba et al. | 548/551 |
| 5,356,861 | 10/1994 | Gednalski et al. | 504/206 |
| 5,389,680 | 2/1995 | Ruminski | 514/563 |
| 5,464,807 | 11/1995 | Claude et al. | 504/206 |
| 5,622,546 | 4/1997 | Elbe et al. | 504/289 |

FOREIGN PATENT DOCUMENTS

| | | | |
|---|---|---|---|
| 0 036 106 | 9/1981 | European Pat. Off. | A01N 57/20 |
| 0 243 522 | 4/1986 | European Pat. Off. | A01N 59/02 |
| 0 438 209 | 7/1991 | European Pat. Off. | C07D 239/54 |
| 2 096 713 | 6/1970 | France | A01N 17/00 |
| 2 096 963 | 7/1970 | France | A01N 17/00 |
| 2 529 755 | 6/1983 | France | A01N 35/02 |
| 2 697 133 | 4/1994 | France | A01N 31/00 |
| 60-172903 | 6/1985 | Japan | A01N 43/30 |
| 95/33728 | 12/1995 | WIPO | C07D 231/20 |
| 96/32839 | 10/1996 | WIPO | |

OTHER PUBLICATIONS

International Search Report, PCT/US 98/01841.
*Chemical Abstracts* 115: 207989 (1991).

*Primary Examiner*—S. Mark Clardy
*Attorney, Agent, or Firm*—James C. Forbes

[57] ABSTRACT

A process is provided for enhancing the reliability and consistency of effectiveness of an exogenous chemical substance applied to foliage of a plant, involving application of a phenyl-substituted olefin compound to the foliage, either sequentially or simultaneously with the exogenous chemical substance. Also provided are plant treatment and concentrate compositions comprising an exogenous chemical substance and a phenyl-substituted olefin compound.

86 Claims, No Drawings

PROCESS AND COMPOSITIONS FOR ENHANCING RELIABILITY OF EXOGENOUS CHEMICAL SUBSTANCES APPLIED TO PLANTS

This application claims the benefit of U.S. provisional application Ser. No. 60/034,887 filed Jan. 31, 1997, which is incorporated herein by reference.

FIELD OF THE INVENTION

The present invention relates to a process for enhancing the reliability of biological effectiveness of an exogenous chemical substance applied to foliage of a plant. The process involves application of a phenyl-substituted olefin compound to the foliage, either sequentially or simultaneously with the exogenous chemical substance. The invention also relates to plant treatment compositions comprising an exogenous chemical substance and a phenyl-substituted olefin compound.

BACKGROUND OF THE INVENTION

For many purposes in agriculture and related endeavors it is desired to treat plants with exogenous chemical substances of various kinds. An exogenous chemical substance as defined herein is a chemical substance, whether naturally or synthetically obtained, which is applied to a plant to result in expressing a desired biological activity. By "biological activity" is meant the elicitation of a stimulatory, inhibitory, regulatory, therapeutic, toxic or lethal response in the plant or in a pathogen, parasite or feeding organism present in or on the plant. Examples of exogenous chemical substances include, but are not limited to, chemical pesticides (such as herbicides, fungicides, bactericides, viricides, insecticides, miticides, nematicides and molluscicides), plant growth regulators, fertilizers and nutrients, gametocides, defoliants, desiccants, mixtures thereof and the like.

Plants treatable by the process herein described are those classified as tracheophytes or vascular plants, i.e. those having a differentiated vascular or conducting system comprising phloem and xylem tissues. Vascular plants include pteridophtyes, gymnosperms and angiosperms. The process and compositions provided herein are particularly adapted for treatment of terrestrial plants, though aquatic plants that are semi-submerged or have leaves or fronds above water level can also be treated by such process and compositions.

Many exogenous chemical substances are applied to foliage (i.e. leaves and other non-woody above-ground parts) of a plant, and have a site of action in the plant either close to or remote from the locus of application. Such substances are referred to herein as foliar-applied exogenous chemical substances. Typically, by plant treatment processes known in the art, only a small portion of the amount of an exogenous chemical substance applied to foliage reaches sites of action in the plant where the biological effect of the exogenous chemical substance can be usefully expressed. It is therefore a major desideratum in agriculture and related endeavors to enhance the efficiency of delivery of foliar-applied exogenous chemical substances to their sites of action in plants, and thereby to enhance the biological effectiveness of the exogenous chemical substance for the purpose for which it is used.

Application to foliage of an exogenous chemical substance by processes known in the art does not universally result in inefficient delivery to sites of action. In some situations such processes provide excellent biological effectiveness, even at a low use rate of the exogenous chemical substance. In other situations the same processes, using the same rate of the exogenous chemical substance, provide inadequate biological effectiveness. Thus, these processes are inconsistent in the result they provide, or they cannot be relied upon to provide the desired result. The problem is that it is seldom possible to identify in advance those situations where good biological effectiveness will be obtained, partly because so many factors influence delivery efficiency. These factors include weather (temperature, relative humidity, daylength, cloudiness, precipitation, wind, etc.) preceding, during and following application, soil conditions (fertility, aeration, etc.), plant growth stage, health and physiological status, equipment-related inaccuracies in application, and other factors. Therefore, to help ensure reliable or consistent biological effectiveness of a foliar-applied exogenous chemical substance, the user typically applies the substance at a higher rate than truly necessary in the majority of situations.

Benefits of a process providing greater reliability of biological effectiveness include an ability to reduce rates of application of exogenous chemical substances without sacrificing consistency of biological effectiveness. Pressures felt by the agricultural industry to reduce pesticide, particularly herbicide, usage are well evidenced by symposia on the subject, such as that held in 1993 by the Weed Science Society of America and documented in *Weed Technology* 8, 331–386 (1994). Reduced use rates bring rewards not only environmentally but also economically, as the cost per unit area treated decreases.

A widely practiced method of enhancing reliability of biological effectiveness of a foliar-applied composition of an exogenous chemical substances, particularly a herbicide, is to add an enhancing agent comprising an ammonium salt, most commonly ammonium sulfate, to the composition being applied. It is well known to those practising this method that enhanced biological effectiveness is not assured with every use; however the low cost of the method means that even if biological effectiveness is enhanced in only a small proportion, for example 1 in 5, of times the method is used, it is still worthwhile.

There are limitations to the usefulness of ammonium salts as enhancing agents resulting from the relatively high rates that have to be used. Ammonium sulfate, for example, is typically used at concentrations in an aqueous application solution of 1–5% weight/volume, for example around 2% weight/volume. Common spraying equipment used in agriculture applies a spray volume of 50–1000 liters per hectare (l/ha) of solution;

at a typical spray volume of 200 l/ha containing 2% ammonium sulfate, the use rate of ammonium sulfate is 4 kg/ha. Such a high use rate leads to inconvenience for the user and difficulties for the formulator desiring to provide a product combining both an exogenous chemical substance and an enhancing agent based on ammonium sulfate.

Most exogenous chemical substances are designed to be used at much lower rates than those shown above for ammonium sulfate, for example 1–1000 grams of active ingredient per hectare (g a.i./ha). Thus, in an application process using ammonium sulfate, the amount of ammonium sulfate used is typically much greater than the amount of the exogenous chemical substance. It is consequently uneconomic in most situations for the manufacturer of the exogenous chemical substance to supply a useful amount of ammonium sulfate preformulated with the exogenous chemical substance. Economics in the agricultural pesticide business, for example, mandate that the pesticide be formulated at as high a concentration or loading as possible to minimize packaging, shipping and storage costs. The requirement to coformulate a large amount of ammonium sulfate with the pesticide active ingredient is inconsistent with achieving a high loading of active ingredient.

It is therefore an objective of the present invention to provide an agent that lo enhances the reliability of effectiveness of foliar applied exogenous chemical substances but that achieves this at much lower use rates than is the case with ammonium sulfate.

Many studies have been conducted in pursuit of this elusive goal. As biological effectiveness of an exogenous chemical substance depends upon delivery of the substance into living cells or tissues of the plant, some investigators have focused the search for a low-rate enhancing agent on classes of compounds which, at low rates, can be expected to stimulate various biological processes in plants. U.S. Pat. No. 4,436,547 to Sampson discloses that additives to improve the action of agricultural chemicals can include a carbohydrate source or organic acid to supply metabolizable energy or as precursors of amino acids and nucleotides, a vitamin or coenzyme to stimulate metabolic processes, a nucleic acid precursor to stimulate nucleic acid synthesis, a fatty acid (or fat or oil that can be degraded thereto) as precursor of molecules required in growth processes, an amino acid as structural unit for protein synthesis, and a naturally occurring plant growth regulator to affect metabolism in such a way as to render an applied pesticide more effective. In the case of herbicides, it is postulated in the above cited patent that "by stimulating growth and uptake of applied chemicals it is possible to enhance the activity of a number of herbicides, especially against older more established weeds."

The present invention provides a process for enhancing reliability of biological effectiveness of a foliar-applied exogenous chemical substance involving an enhancing agent not contemplated by Sampson, namely a phenyl-substituted olefin compound as herein defined.

SUMMARY OF THE INVENTION

A process for enhancing reliability of biological effectiveness of an exogenous chemical substance is provided. This process comprises the steps of (a) applying to foliage of the plant a phenyl-substituted olefin compound more particularly defined hereinbelow and (b) applying a biologically effective amount of the exogenous chemical substance to the same foliage, wherein the phenyl-substituted olefin compound is applied in a substantially non-phytotoxic amount of at least about 0.25 grams per hectare (g/ha) but not in an amount sufficient to antagonize biological effectiveness of the exogenous chemical substance.

A biologically effective amount of an exogenous chemical substance is an amount which elicits a useful degree of biological activity when applied in accordance with a process contemplated herein.

A contemplated phenyl-substituted olefin compound is defined as a compound whose molecular weight is about 100 to about 300, and whose molecular structure comprises:

(1) a phenyl ring linked to (2) an olefinic carbon chain that is not part of a ring structure fused to the phenyl ring, the olefinic carbon chain having (3) an ethylenic double bond whose proximal carbon atom is the first or second carbon atom in the chain from the phenyl ring.

The proximal carbon atom of the ethylenic double bond is the carbon atom that is closer to the phenyl ring.

As used herein, the phrase "substantially non-phytotoxic" means that the amount of phenyl-substituted olefin compound used, if applied in the absence of the exogenous chemical substance, causes no significant injury, growth reduction, herbicidal effect or readily visible symptoms to the plant.

In a process of the present invention, application of the exogenous chemical substance and application of the phenyl-substituted olefin compound occur either sequentially or simultaneously. In the case of simultaneous application, the exogenous chemical substance and the phenyl-substituted olefin compound can be applied, for example by spraying, to the foliage of the plant, a single composition adapted for such application and containing both the exogenous chemical substance and the phenyl-substituted olefin compound, together with an application medium.

Thus, one embodiment of the present invention is a plant treatment composition for application to foliage of a plant comprising (a) an application medium, in which is dissolved or dispersed (b) a biologically effective amount of an exogenous chemical substance, and (c) a phenyl-substituted olefin compound as defined above, such that, when the composition is applied to the foliage the phenyl-substituted olefin compound is present in a substantially non-phytotoxic amount of at least about 0.25 g/ha but not in an amount sufficient to antagonize biological effectiveness of the exogenous chemical substance. Typically, the application medium appropriate for compositions of the invention is water.

A phenyl-substituted olefin compound as used herein can be seen from the above definition to be a compound having as part of its molecular structure a vinylbenzene or allylbenzene moiety:

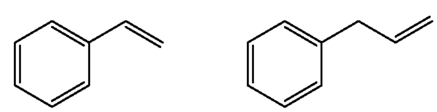

vinylbenzene allylbenzene

As described below, either or both of the phenyl ring and the olefinic carbon chain linked thereto are optionally substituted at one or more positions. Vinylbenzene (styrene) and allylbenzene (3-phenyl-1-propene) themselves have the above structures with no substitution, and are encompassed within the above definition.

U.S. Pat. No. 5,281,571 to Woodard et al. discloses preparation of certain phenylpyrazole compounds as herbicides. Some of these compounds contain a vinylbenzene or allylbenzene moiety as above; they include 3-[2-chloro-5-[4-chloro-1-methyl-5-(trifluoromethyl)-1H-pyrazol-3-yl]-4-fluorophenyl]-2-methyl-2-propenoic acid and its ethyl ester, and 3-[2-chloro-5-[4-chloro-1-methyl-5-(trifluoromethyl)-1H-pyrazol- 3-yl]-4-fluorophenyl]-2-propenoic acid and its methyl ester. It is disclosed that these compounds can be combined with other herbicides including N-phosphonomethylglycine and its salts, other pesticides, or fertilizers.

European Patent Application No. 0 438 209 to Ishii el al. discloses preparation of certain phenylpyrimidinediones as herbicides, including 6-(2-chlorophenyl)-3-[4-[2-(4-methoxyphenyl)ethenyl]phenyl]-2,4(1H,3H)-pyrimidinedione.

Japanese Patent Application No. 03151367 to Miura et al. discloses preparation of phenylpyrazole derivatives as herbicides, including 2-[2-chloro-5-[4-chloro-5-(difluoromethoxy)-1-methyl-1H-pyrazol-3-yl]-4-fluorophenyl]-ethenol formate, the methyl and 2-propenyl esters of 3-[2-chloro-5-[4-chloro-5-(difluoromethoxy)-1-methyl-1 H-pyrazol-3-yl]-4-fluorophenyl]-2-propenoic acid, 4-[2-chloro-5-[4-chloro-5-(difluoromethoxy)-1-methyl-1H-pyrazol-3-yl]-4-fluorophenyl]-3-buten-2-one, and the methyl ester of 2-chloro-5-[4-chloro-5-(difluoromethoxy)-1-methyl-1H-pyrazol-3-yl]-4-fluoro-α-(methoxymethylene)benzeneacetic acid.

Other patent publications disclosing herbicides having a vinylbenzene or allylbenzene moiety include U.S. Pat. No. 3,272,842 to Easton & Dillard, U.S. Pat. No. 5,006,157 to Ohba et al., U.S. Pat. No. 5,312,929 to Ohba et al., and International Patent Application No. WO 95/33728 to von dem Bussche-Hünnefeld et al.

Phenyl-substituted olefin compounds useful in the process and compositions of the present invention differ from compounds disclosed in the above publications in that contemplated phenyl-substituted olefin compounds are not themselves herbicidal or substantially phytotoxic at the rates used herein; i.e. they are present in a substantially non-phytotoxic amount. In addition, phenyl-substituted olefin compounds useful in a process or composition of the present invention differ from many of the herbicidal compounds disclosed in the above publications in having lower molecular weight (not greater than about 300).

U.S. Pat. No. 4,436,547 to Sampson cited above discloses plant growth regulators which are diphenyl-1H-pyrazolium salts. U.S. Pat. No. 4,436,547 also discloses that the naturally occurring plant growth regulator indole-3-acetic acid can be used as an additive to improve the action of agricultural chemicals. The indole group contains within it a structure that might be considered a vinylbenzene moiety, except that the carbon chain containing the ethylenic double bond is part of a ring structure fused to the phenyl ring.

The particular phenyl-substituted olefin compounds useful in the process and compositions of the present invention do not encompass compounds having indole groups or other groups in which the alkenyl chain is part of a ring structure fused to the phenyl ring.

French Patent No. 2 697 133 to Terrom discloses biocidal or biostatic compositions comprising a sesquiterpene compound and an aromatic compound having at least one benzene ring. The aromatic compound is there described as a "synergistic agent" and it is postulated by Terrom that the existence of a benzene ring therein is important in providing the synergistic action alleged to be characteristic of the compositions claimed. Uses indicated for such compositions are in the control of molluscs, algae, fungi or bacteria on surfaces such as the keels of boats. Exemplified among the aromatic compounds said to be useful are some having a vinylbenzene moiety, e.g. isoeugenol, isosafrole, cinnamaldehyde and cinnamyl alcohol, some having an allylbenzene moiety, e.g. eugenol, methyl eugenol and safrole, and some having no such moiety, e.g. methyl benzoate, benzyl benzoate, carvacrol and thymol. Eugenol and carvacrol are said to be particularly preferred. Thus, it can be inferred that the existence of a vinyl or allyl moiety attached to the benzene ring of the aromatic compound is of no particular significance in conferring the advantages claimed. No indication is given as to whether the aromatic compound itself has biocidal or biostatic activity when used alone in amounts equivalent to those present in the claimed compositions.

Phenyl-substituted olefin compounds useful in a presently contemplated process or composition generally enhance reliability of effectiveness of foliar-applied exogenous chemical substances at rates much lower than rates typically required of ammonium sulfate as discussed above. Preferred phenyl-substituted olefin compounds are useful in the present process and compositions at rates up to about 250 g/ha.

The present invention has several benefits and advantages. One benefit is that the invention provides a process for treating plants with a foliar-applied exogenous chemical substance that enhances the reliability of effectiveness of the exogenous chemical substance.

A further benefit is provision of an agent that enhances the reliability of effectiveness of foliar-applied exogenous chemical substances in plants but that achieves this at very low use rates, for example about 0.25 to about 250 g/ha, so that, among other advantages, it becomes economically feasible to include the agent in a concentrate composition without excessively reducing the loading therein of the exogenous chemical substance.

Another benefit of the invention is provision of a composition which, when used in accordance with the process of the invention, provides enhanced reliability of effectiveness in plants of an exogenous chemical substance contained in such compositions.

A yet further benefit of the invention is provision of a composition containing an exogenous chemical substance that, through selection of an appropriate phenyl-substituted olefin compound for inclusion in such composition, is better adapted for specific uses than existing compositions of the exogenous chemical substance.

To the extent that such a phenyl-substituted olefin compound has a characteristic, organoleptically acceptable odor, a still further benefit of the invention is provision of a composition containing an exogenous chemical substance, said composition being readily identifiable to a user by smell. A related advantage of the invention is provision of an agent for modifying the odor of a composition containing an exogenous chemical substance that would otherwise have an unpleasant or noxious odor.

DETAILED DESCRIPTION OF THE INVENTION

The present invention provides a process for enhancing biological effectiveness of an exogenous chemical substance applied to a plant. This process comprises (a) applying to foliage of the plant a phenyl-substituted olefin compound as defined herein and (b) applying a biologically effective amount of the exogenous chemical substance to the same foliage, wherein the phenyl-substituted olefin compound is applied in a substantially non-phytotoxic amount of at least about 0.25 grams per hectare (g/ha) but not in an amount sufficient to antagonize biological effectiveness of the exogenous chemical substance.

Although a process as defined above comprises application of a phenyl-substituted olefin compound and an exogenous chemical substance to foliage, it will be understood by those of skill in the art that a process of the invention can alternatively comprise application of a phenyl-substituted olefin compound and an exogenous chemical substance to a plant part other than foliage, for example to bark, to internal tissues by injection, or to a cut stump.

A contemplated phenyl-substituted olefin compound has a molecular weight of about 100 to about 300, preferably about 125 to about 175. Its molecular structure comprises a phenyl ring linked to an olefinic carbon chain that is not part of a ring structure fused to the phenyl ring. The olefinic carbon chain contains an ethylenic double bond whose proximal carbon atom is the first or second carbon atom in the chain from the phenyl ring.

Although the olefinic carbon chain can have more than one ethylenic double bond, presently preferred phenyl-substituted olefin compounds have only one ethylenic double bond in the olefinic carbon chain, so that the olefinic carbon chain is an alkenyl or substituted alkenyl group.

Preferred phenyl-substituted olefin compounds useful in a process or composition of the invention have a chemical structure that corresponds to formula (I) or formula (II):

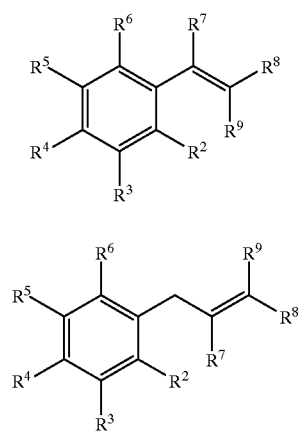

wherein, in either of formulas (I) or (II), substituents are as described below, with the following stipulations unless otherwise indicated:

(1) where a substituent $R^2$ through $R^9$, or a subgroup thereof, is described as a hydrocarbyl, hydrocarbyloxy, halocarbyl, halohydrocarbyl, hydroxyhydrocarbyl, hydrocarboyl or hydrocarbylenedioxy group, that substituent or subgroup contains 1 to 6 carbon atoms and comprises a saturated or unsaturated linear or branched aliphatic or a saturated or unsaturated alicyclic structure; illustratively, therefore, examples of hydrocarbyl groups include, without limitation, $C_{1-6}$ alkyl, $C_{2-6}$ alkenyl and $C_{2-6}$ alkynyl, and examples of hydrocarbyloxy groups include, without limitation, $C_{1-6}$ alkoxy; however the terms "hydrocarbyl", "hydrocarbyloxy", "halocarbyl", "halohydrocarbyl", "hydroxyhydrocarbyl", "hydrocarboyl" and "hydrocarbylenedioxy" as used in the present specification do not encompass aromatic groups;

(2) phenyl substituents or subgroups are themselves optionally and independently substituted at one or more positions with amino, carbamoyl, hydrocarbyl or hydrocarbyloxy groups;

(3) phenylhydrocarbyl, phenylhydrocarboyl, phenylhydrocarbyloxy and phenylamino substituents comprise a phenyl substituent as just described linked to a hydrocarbyl, hydrocarboyl, hydrocarbyloxy or amino group respectively;

(4) the term "hydrido" as used herein refers to a substituent consisting of a covalently bonded hydrogen atom (—H).

Substituents $R^2$ through $R^6$ on the phenyl ring of such preferred phenyl-substituted olefin compounds are as follows. $R^2$ and $R^6$ are independently hydrido, hydroxy or hydrocarbyloxy. $R^3$, $R^4$ and $R^5$ are independently hydrido, halogen, hydroxy, hydrocarbyl, hydrocarbyloxy, phenyl, phenylhydrocarbyloxy, hydroxyhydrocarbyl, halocarbyl, halohydrocarbyl, cyano, amino, nitro, or —COOR$^{11}$ groups where $R^{11}$ is a hydrido, hydrocarbyl, phenyl or phenylhydrocarbyl group; or two adjacent R groups among $R^3$, $R^4$ and $R^5$ form a hydrocarbylenedioxy bridge such as a methylenedioxy, ethylenedioxy or propylenedioxy bridge.

$R^7$, $R^8$ and $R^9$ substituents on the olefinic carbon chain of such preferred phenyl-substituted olefin compounds are as follows.

$R^7$ and $R^9$ are independently hydrido, hydroxy, hydrocarbyl, phenyl, cyano, or —COOR$^{12}$ groups where $R^{17}$ is a hydrido, hydrocarbyl, phenyl or phenylhydrocarbyl group, or $R^7$ together with $R^8$ and the carbon atoms linked by the ethylenic double bond of formula (I) or formula (II) forms a cyclopentenedione ring substituent of formula (III):

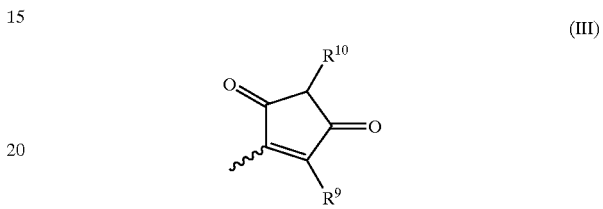

wherein the wavy line depicts the bond adjacent to the ethylenic double bond proximal to the phenyl ring of formula (I) or formula (II), $R^9$ is as defined above and $R^{10}$ is a hydrido, hydrocarbyl, phenyl or cyano group.

$R^8$, unless forming said cyclopentenedione ring with $R^7$, is a hydrido, hydrocarbyl, phenyl, phenylhydrocarbyl, cyano, amino, phenylamino, —ZOR$^{15}$, —ZOCOR$^{15}$, —CHO, —CO-hydrocarbyl, —CO-phenyl, —CO-furanyl, —COOR$^{15}$, —CONR$^{15}$R$^{16}$, —CONHN=CH-phenyl, —ZNR$^{15}$R$^{16}$, —CH=NOH, or —CH=C(CN)COOR$^{15}$ group, or a group of formula (IV):

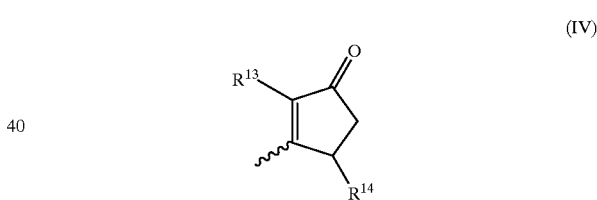

wherein $R^{13}$ is —CH$_2$COOR$^{15}$ and $R^{14}$ is a hydrido, hydroxy or hydrocarbyloxy group; where Z is a $C_{1-6}$ aliphatic or alicyclic hydrocarbylene group, and $R^{15}$ and $R^{16}$ are independently selected from hydrido, hydrocarbyl, phenyl and phenylhydrocarbyl groups. $R^8$ and $R^9$ are stereochemically interchangeable.

In particularly preferred examples of phenyl-substituted olefin compounds of formulas (I) and (II), substituents are as follows. $R^2$ and $R^6$ substituents are independently hydrido, hydroxy or methoxy groups with at least one of $R^2$ and $R^6$ being hydrido. $R^3$ and $R^5$ substituents, except where either forms a methylenedioxy bridge with $R^4$, are independently hydrido, methyl, hydroxy or methoxy groups, most preferably at least one of $R^3$ and $R^5$ being hydrido. Where $R^4$ is hydroxy, it is preferred that one of $R^3$ and $R^5$ be methyl or methoxy. $R^4$ is a hydrido, halogen, methyl, ethyl, hydroxy, methoxy, benzyloxy (—O—CH$_2$-phenyl), trifluoromethyl, amino or nitro group, or $R^4$ forms a methylenedioxy bridge with $R^3$ or $R^5$. $R^7$ is a hydrido or $C_{1-3}$ alkyl group; or $R^7$, together with $R^8$ and the carbon atoms linked by the ethylenic double bond of formula (I) or formula (II), forms a cyclopentenedione ring substituent of formula (III) wherein $R^9$ is hydroxy and $R^{10}$ is hydrido. $R^8$, unless forming said cyclopentenedione ring with $R^7$, is hydrido, methyl, hydroxy-$C_{1-2}$ alkyl or the acetate ester thereof, cyano, anilino, carbamoyl, —CONHN=CH—(4-methoxy)phenyl, —CONHN=CH—(4-acetamido)phenyl, —COOR$^{17}$ where $R^{17}$ is a hydrido, methyl, ethyl, allyl, unsubstituted phenyl or benzyl group, or —COR$^{18}$ where $R^{18}$ is a hydrido, $C_{1-3}$ alkyl, unsubstituted phenyl or 4-methylphenyl group. $R^9$, except where $R^7$ and $R^8$ form said cyclopentenedione ring, is a hydrido, hydroxy, $C_{1-6}$ alkyl, cyano, —COOH or —COCH$_3$ group. $R^8$ and $R^9$ are stereochemically interchangeable.

Phenyl-substituted olefin compounds useful in the process and compositions of the present invention can be selected from the following non-restrictive list of compounds accompanied by CAS Registry numbers where available:

styrene, 100-42-5 (vinylbenzene);
4-hydroxystyrene, 2628-17-3 (4-vinylphenol);
4-methylstyrene, 622-97-9;
3-methylstyrene, 100-80-1;
chloromethylstyrene, mixture of 3- and 4-isomers, 57458-41-0;
4-methoxystyrene, 637-69-4 (4-vinylanisole);
4-phenylstyrene, 2350-89-2;
1-(2-hydroxyphenyl)-1-propene, 6380-21-8;
1-(4-methoxyphenyl)-1-propene, 4180-23-8 (anethole);
1-(4-hydroxy-3-methoxyphenyl)-1-propene, 97-54-1 (isoeugenol);
1-(4-ethoxy-3-hydroxyphenyl)-1-propene, 94-86-0;
1-(3,4-dimethoxyphenyl)-1-propene, 93-16-3;
1-(3,4-(methylenedioxy)phenyl)-1-propene, 120-58-1 (isosafrole);
4-vinylbenzoic acid, 1075-49-6;
1-phenyl-2-methyl-1-propene, 768-49-0;
1,2-diphenyl-1-propene, 833-81-8;
1-phenyl-2-butene;
3-phenyl-2-pentene, 4701-36-4;
2-phenyl-2-pentene, 53172-84-2;
3-phenyl-1-propene, 300-57-2 (allylbenzene);
3-(2-hydroxyphenyl)-1-propene, 1745-81-9;
3-(4-methoxyphenyl)-1-propene, 140-67-0 (estragole);
3-(2-hydroxy-3-methylphenyl)-1-propene, 3354-58-3;
3-(4-hydroxy-3-methoxyphenyl)-1-propene, 97-53-0 (eugenol);
3-(2-hydroxy-3-methoxyphenyl)-1-propene, 579-60-2 (o-eugenol);
3-(3,4-dimethoxyphenyl)--1-propene, 93-15-2 (methyl eugenol);
3-(4-hydroxy-3,5-dimethoxyphenyl)-1-propene, 6627-88-9;
3-(3,4-(methylenedioxy)phenyl)-1-propene, 94-59-7 (safrole);
cinnamyl alcohol, 104-54-1;
cinnamyl acetate, 103-54-8;
α-methylcinnamyl alcohol, 1504-55-8;
4-hydroxy-3-methoxycinnamyl alcohol, 458-35-5 (coniferyl alcohol);
cinnamic acid, 140-10-3;
methyl cinnamate, 103-26-4;
ethyl cinnamate, 103-36-6;
allyl cinnamate, 1866-31-5;
phenyl cinnamate, 2757-04-2;
benzyl cinnamate, 103-41-3;
4-hydroxycinnamic acid, 7400-08-0;
2-hydroxycinnamic acid, 614-60-8;
4-methylcinnamic acid, 1866-39-3;
4-methoxycinnamic acid, 830-09-1;
3-methoxycinnamic acid, 6099-04-3;
4-chlorocinnamic acid, 1615-02-7;
4-nitrocinnamic acid, 619-89-6;
ethyl 4-nitrocinnamate, 953-26-4;
3,4-dihydroxycinnamic acid, 331-39-5 (caffeic acid);
4-methoxy-3-hydroxycinnamic acid, 537-73-5;
4-hydroxy-3-methoxycinnamic acid, 1135-24-6;
ethyl 4-hydroxy-3-methoxycinnamate, 4046-02-0;
methyl 4-hydroxy-3,5-dimethylcinnamate;
ethyl 4-hydroxy-3,5-dimethylcinnamate;
4-hydroxy-3,5-dimethoxycinnamic acid, 530-59-6;
3,4-(methylenedioxy)cinnamic acid, 2373-80-0;
α-methylcinnamic acid, 1199-77-5;
4-methoxy-α-methylcinnamic acid;
2-methoxy-α-methylcinnamic acid;
α-ethylcinnamic acid;
4-hydroxy-α-cyanocinnamic acid, 28166-41-8;
β-methylcinnamic acid;
methyl β-methylcinnamate;
β-phenylcinnamic acid;
methyl β-phenylcinnamate;
methyl 4-amino-β-methylcinnamate;
dimethyl (4-nitrobenzylidene)malonate, 38323-22-7;
cinnamaldehyde, 14371-10-9;
4-methoxycinnamaldehyde, 1963-36-6;
2-methoxycinnamaldehyde, 1504-74-1;
4-nitrocinnamaldehyde, 1734-79-8;
4-hydroxy-3-methoxycinnamaldehyde, 458-36-6;
α-methylcinnamaldehyde, 101-39-3;
4-methoxy-α-methylcinnamaldehyde;
α-butylcinnamaidehyde;
α-amylcinnamaidehyde, 122-40-7;
α-hexylcinnamaldehyde, 101-86-0;
β-phenylcinnamaldehyde, 13702-35-7;
2-phenyl-3-pentenal;
2-phenyl-4-methyl-3-pentenal;
1,3-diphenyl-2-propen-1-one, 614-47-1 (chalcone);
1-phenyl-3-(3,4-(methylenedioxy)phenyl)-2-propen-1-one;
1-(4-bromophenyl)-3-(3,4-(methylenedioxy)phenyl)-2-propen-1-one;
1-(4-fluorophenyl)-3-(3,4-(methylenedioxy)phenyl)-2-propen-1-one;
1-(4-methylphenyl)-3-(3,4-(methylenedioxy)phenyl)-2-propen-1-one;
1-cyclopropyl-3-(3,4-methylenedioxy)phenyl)-2-propen-1-one;
4-phenyl-3-buten-2-one, 122-57-6;
4-(4-methylphenyl)-3-buten-2-one;
4-(4-bromophenyl)-3-buten-2-one;
4-(3-methoxyphenyl)-3-buten-2-one;

4-(2-hydroxyphenyl)-3-buten-2-one;
4-(4-hydroxy-3-methoxyphenyl)-3-buten-2-one, 1080-12-2;
4-phenyl-3-methyl-3-buten-2-one;
3,4-diphenyl-3-buten-2-one;
1,4-diphenyl-3-buten-2-one;
1,3-diphenyl-2-buten-1-one;
1-phenyl-1-penten-3-one;
1-(4-methoxyphenyl)-1-penten-3-one;
1-phenyl-1-hexen-3-one;
1-phenyl-5-methyl-1-hexen-3-one;
cinnamonitrile, 1885-38-7;
4-methoxycinnamonitrile, 28446-68-6;
4-chlorocinnamonitrile, 28446-72-2;
4-methyl-α-(4-methylbenzoyl)cinnamonitrile;
benzylidinemalononitrile, 2700-22-3;
α-cyclopropylbenzylidinemalononitrile;
2-methoxy-4-(2-nitrovinyl)phenol, 6178-42-3;
3-benzylidenepenta-2,4-dione;
1-(4-ethylphenyl)-3-anilino-2-propene;
cinnamamide, 621-79-4;
3-bromo-N-ethylcinnamamide, 58473-74-8;
cinnamic (4-methoxybenzylidene)hydrazide;
cinnamic (4-acetamidobenzylidene)hydrazide;
4-phenyl-3-butenol;
methyl α-cyanocinnamylidineacetate;
4-hydroxy-5-phenyl-4-cyclopentene-1,3-dione, 36394-22-6.

The presence of an ethylenic bond having its proximal carbon atom as the first or second carbon atom in the chain as counted from the phenyl ring is believed to correlate strongly to the biological efficacy enhancing property of phenyl-substituted olefin compounds. This unexpected correlation is based on the finding that of 36 studied compounds that contain a phenyl ring linked to an optionally substituted hydrocarbyl chain of at least two carbon atoms and free of ethylenic unsaturation, 23 (64%) exhibited no enhancement of glyphosate herbicidal effectiveness when used at rates of 20 to 200 10 g/ha in the assay described in Example 1. These results are to be contrasted with the findings shown in Example 1 that of 57 illustrative phenyl-substituted olefin compounds, only 5 (9%) exhibited no enhancement of glyphosate herbicidal effectiveness in the same range of rates in the same assay. Those 23 compounds lacking ethylenic unsaturation and exhibiting no enhancement of glyphosate herbicidal effectiveness are listed below, with their CAS Registry numbers where available:

ethylbenzene, 100-41-4;
4-ethylphenol, 123-07-9;
2,6-di-tert-butyl-4-methylphenol, 128-37-0;
2,6-di-tert-butyl-4-methoxyphenol, 489-01-0;
3,5-di-tert-butyl-4-hydroxybenzoic acid, 1421-49-4;
4-isoamylphenol;
4-tert-amylphenol;
4-cyclopentylphenol, 1518-84-9;
1-(3,4-methylenedioxy)phenylpropane;
2-(4-hydroxyphenyl)butane, 99-71-8;
4-isopropyltoluene, 99-87-6 (p-cymene);
2-hydroxy-4-isopropyltoluene, 499-75-2 (carvacrol);
1-phenyl-1-propanol, 93-54-9;

3-phenylpropionic acid, 501-52-0 (hydrocinnamic acid);
3-(4-hydroxyphenyl)propionic acid, 501-97-3;
3-(3,4-dihydroxyphenyl)propionic acid, 1078-61-1 (hydrocaffeic acid);
methyl 2-phenylbutyrate;
diethyl benzylmalonate, 607-81-8;
diethyl 2-ethyl-2-(4-methylphenyl)malonate, 68692-80-8;
hydrocinnamaldehyde, 104-53-0;
4-(4-methylphenyl)-2-butanone;
4-(4-hydroxyphenyl)-2-butanone, 5471-51-2;
phenethyl levulinate.

For phenyl-substituted olefin compounds showing stereoisomerism, both cis and trans isomers are useful. In most cases, the trans isomer is more readily obtainable and has lower cost, therefore it is generally preferred on economic grounds that a phenyl-substituted olefin compound showing stereoisomerism is present predominantly as the trans isomer.

An especially preferred subclass of compounds useful to enhance reliability of effectiveness of exogenous chemical substances according to a process of the invention are cinnamaldehyde derivatives, defined as compounds of formula (V):

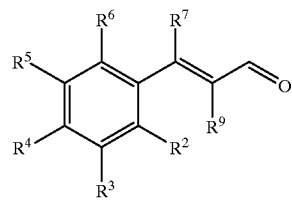

(V)

or stereochemical isomers thereof, wherein $R^7$ and $R^9$ are independently hydrido or $C_{1-6}$ alkyl groups, and the five substituents on the phenyl ring ($R^2$ to $R^6$) are hydrido, hydroxy or methoxy groups with at least three such substituents being hydrido groups and no more than one such substituent being a hydroxy group. A particularly preferred cinnamaldehyde derivative, especially where the exogenous chemical substance is glyphosate, is α-methylcinnamaldehyde, or a compound which readily converts thereto in or on the surface of plant foliage. Especially useful is the trans isomer of α-methylcinnamaldehyde shown in formula (VI) below:

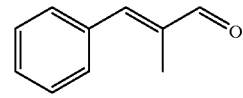

(VI)

Another especially preferred subclass of phenyl-substituted olefin compounds useful to enhance reliability of effectiveness of exogenous chemical substances according to a process of the invention are 3,4-methylenedioxyphenyl compounds, defined as compounds of formula (I) or formula (II) in which $R^2$, $R^5$ and $R^6$ are hydrido groups and $R^3$ and $R^4$ form a methylenedioxy bridge. A particularly preferred 3,4-methylenedioxyphenyl compound is safrole shown in formula (VII) below:

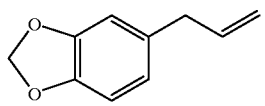

(VII)

Contemplated phenyl-substituted olefin compounds surprisingly enhance reliability of effectiveness of exogenous chemical substances at rates much lower than rates typically required of ammonium sulfate. Preferred phenyl-substituted olefin compounds are useful in the present process at rates up to about 250 g/ha and are themselves substantially non-phytotoxic at such rates.

A further embodiment of the invention is a plant treatment composition comprising an exogenous chemical substance and a phenyl-substituted olefin compound having the chemical structure corresponding to formula (I) or formula (II) as defined above. The weight/weight ratio of phenyl-substituted olefin compound to exogenous chemical substance in such a composition can vary within wide limits, so long as when the composition is applied at a rate appropriate to provide a biologically effective amount of the exogenous chemical substance, it is important that the amount of the phenyl-substituted olefin compound provided by the composition be at least about 0.25 g/ha but not sufficient to antagonize effectiveness of the exogenous chemical substance. Preferably the weight/weight ratio of phenyl-substituted olefin compound to exogenous chemical substance is such that when the composition is applied at a rate appropriate to provide an effective amount of the exogenous chemical substance, the phenyl-substituted olefin compound is applied in a substantially non-phytotoxic amount of about 0.25 to about 250 g/ha. Thus, for example, where the exogenous chemical substance is to be applied at about 5 g a.i./ha, preferred weight/weight ratios of phenyl-substituted olefin compound to exogenous chemical substance are about 1:20 to about 50:1. As a further example, where the exogenous chemical substance is to be applied at about 2 kg a.i./ha, preferred weight/weight ratios of phenyl-substituted olefin compound to exogenous chemical substance are about 1:8000 to about 1:8.

Compositions of the invention can take the form of dilute ready-to-apply solutions or dispersions, referred to herein as plant treatment compositions or spray compositions, as well as liquid and solid concentrates which, on dilution, dispersion or dissolution in water or other carrier, provide such plant treatment compositions.

In making a liquid or solid concentrate, the exogenous chemical substance is typically blended by the manufacturer with suitable excipient ingredients. Such ingredients are well known to those of skill in the art and their selection depends on the exogenous chemical substance and on the use to which it will be put. They include, without limitation, solvents, surfactants, dispersants, thickening agents, antifoams, dyes, antifreezes, preservatives and the like. In an embodiment of the present invention, the process provided includes a step of mixing a phenyl-substituted olefin compound and an exogenous chemical substance with suitable excipient ingredients to form a concentrate composition. This concentrate composition is later diluted, dissolved or dispersed in water to make a spray composition, which is then applied by spraying to foliage of a plant. That dilution, dissolution or dispersion in water can be accomplished by adding water to the concentrate composition, by adding the concentrate composition to water, or by simply mixing the two together in any other way. Thus, the manner of admixture has not been found to be of consequence to the result obtained thereafter. Optionally, other ingredients can be added during the dilution, dissolution or dispersion step if desired.

If both the exogenous chemical substance and the phenyl-substituted olefin compound are readily soluble in water, a liquid concentrate can be provided as a simple aqueous solution. If, on the other hand, neither is readily soluble in water, various ways are known in the art of formulating them as liquid concentrates, including emulsifiable concentrates, suspension concentrates and aqueous emulsions.

Of particular interest are situations in which the exogenous chemical substance is readily water-soluble and the phenyl-substituted olefin compound is oil-soluble. In such situations, a preferred form of concentrate composition of the invention is an emulsion having an aqueous phase and an oil phase, wherein the exogenous chemical substance is lo present primarily in the aqueous phase and the phenyl-substituted olefin compound is present primarily in the oil phase, and wherein the emulsion is stabilized by means of one or more emulsifiers. The oil phase can comprise any of a large number of organic oils and solvents known in the agricultural chemical formulation art, including paraffinic and aromatic oils, or fatty acid alkylesters such as butyl stearate, isopropyl myristate or methyl oleate. Alternatively, the oil phase can consist essentially of the phenyl-substituted olefin compound itself. Emulsion compositions of the invention include oil-in-water macroemulsions and microemulsions, water-in-oil or invert emulsions, and water-in-oil-in-water multiple emulsions.

A process of the invention has proved particularly useful as a herbicidal process, wherein the exogenous chemical substance is a foliar-applied herbicide.

By "foliar-applied herbicide" is meant a herbicide that is typically applied post-emergence to foliage of plants as opposed to those typically applied pre-emergence to soil. Illustratively, foliar-applied herbicides that can be used in the process of the invention include aminotriazole, asulam, bentazon, bialaphos, bipyridyls such as paraquat, bromacil, clopyralid, cyclohexenones such as sethoxydim, dicamba, diphenylethers such as acifluorfen, fomesafen and oxyfluorfen, fosamine, glufosinate, glyphosate, hydroxybenzonitriles such as bromoxynil, imidazolinones such as imazethapyr, isoxaben, phenoxies such as 2,4-D, phenoxypropionates such as quizalofop, picloram, substituted ureas such as fluometuron, sulfonylureas such as chlorimuron, chlorsulfuron, halosulfuron and sulfometuron, and triazines such as atrazine and metribuzin. Phloem-mobile herbicides that are preferred for use by the process of the invention include but are not limited to aminotriazole, asulam, bialaphos, clopyralid, cyclohexenones, dicamba, glufosinate, glyphosate, imidazolinones, phenoxies, phenoxypropionates, picloram and sulfonylureas.

Herbicidally active derivatives of the above herbicides and of other herbicides are also within the scope of the invention if applied by the process herein described. A herbicidally active derivative is any compound which is a minor structural modification, most commonly but not restrictively a salt or ester, of a herbicide, said compound retaining the essential activity of the parent herbicide although not necessarily having a potency equal to that of the parent herbicide. Usually but not always, the derivative converts to the parent herbicide before or after it enters the treated plant, and is analogous to a pro-drug that converts to an active drug in vivo. Mixtures or coformulations of a herbicide or herbicidally active derivative with other ingredients, or of more than one herbicide, are likewise within the scope contemplated by the present invention.

Although the invention is not limited to any particular class of foliar-applied exogenous chemical substance, a contemplated process or composition has been found to have useful benefits for water-soluble exogenous chemical substances, particularly where the water-soluble exogenous chemical substance is a salt comprising a biologically active ion and a counterion that has less or no biological activity in the amount present or used, and more particularly such a salt having a molecular weight, excluding counterions, of less than about 300, for example the herbicide paraquat, which is typically formulated as the salt paraquat dichloride.

Paraquat is generally non-systemic in plants, but many other foliar-applied exogenous chemical substances which are water-soluble salts having a molecular weight, excluding counterions, of less than about 300 provide at least a part of their biological effectiveness by systemic movement in plants. Especially preferred among such substances are those having one or more functional groups selected from amine, amide, carboxylate, phosphonate and phosphinate groups.

Among such especially preferred exogenous chemical substances are herbicides, for example glyphosate and glufosinate, plant growth regulators, for example ethephon, and nematicides, for example those disclosed in U.S. Pat. No. 5,389,680, the disclosure of which is incorporated herein by reference. Preferred nematicides of this group are salts of 3,4,4-trifluoro-3-butenoic acid or of N-(3,4,4-trifluoro-1-oxo-3-butenyl)glycine.

Systemic movement in plants can take place via apoplastic (non-living) pathways, including within xylem vessels and in intercellular spaces and cell walls, via symplastic (living) pathways, including within phloem elements and other tissues composed of cells connected sympastically by plasmodesmata, or via both apoplastic and symplastic pathways. For foliar-applied systemic exogenous chemical substances, the most important pathway is the phloem, and the present invention is believed to provide the greatest benefits for exogenous chemical substances that are phloem-mobile.

Among systemic foliar-applied exogenous chemical substances, those which are water-soluble are particularly favored for use according to the present invention. More preferred among those are water-soluble salts comprising a biologically active ion and a counterion which has less or no biological activity. Even more preferred among such salts are those having a molecular weight, excluding counterions, of less than about 300. Especially preferred are those having one or more functional groups selected from amine, amide, carboxylate, phosphonate and phosphinate groups.

Among such especially preferred exogenous chemical substances are herbicides, for example glyphosate and glufosinate, plant growth regulators, for example ethephon, and nematicides, for example those disclosed in U.S. Pat. No. 5,389,680, the disclosure of which is incorporated herein by reference. Preferred nematicides of this group are salts of 3,4,4-trifluoro-3-butenoic acid or of N-(3,4,4-trifluoro-1-oxo-3-butenyl)glycine.

An especially preferred herbicide useful in the process and compositions of the present invention is glyphosate. The term "glyphosate" is used herein to refer collectively to the parent herbicide N-phosphonomethylglycine (otherwise known as glyphosate acid), to a salt or ester thereof, or to a compound which is converted to N-phosphonomethylglycine in plant tissues or which otherwise provides N-phosphonomethylglycine in ionic form (otherwise known as glyphosate ion).

Illustratively, water-soluble glyphosate salts useful herein are disclosed in U.S. Pat. No. 3,799,758 and No. 4,405,531 to Franz, the disclosure of which is incorporated herein by reference. Glyphosate salts that can be used according to the present invention include but are not restricted to alkali metal, for example sodium and potassium, salts; ammonium salt; $C_{1-16}$ alkylammonium, for example dimethylammonium and isopropylammonium, salts; $C_{1-6}$ alkanolammonium, for example monoethanolammonium, salt; $C_{1-16}$ alkylsulfonium, for example trimethylsulfonium, salts; mixtures thereof and the like. The N-phosphonomethylglycine molecule has three acid sites having different pKa values; accordingly mono-, di- and tribasic salts, or any mixture thereof, or salts of any intermediate level of neutralization, can be used.

Glyphosate salts are commercially significant in part because they are water-soluble. Many ammonium, alkylammonium, alkanolammonium, alkylsulfonium and alkali metal salts are highly water-soluble, allowing for formulation as highly concentrated aqueous solutions which can be diluted in water at the point of use. The present invention encompasses compositions containing a glyphosate salt in aqueous solution, and further containing an appropriate amount of a phenyl-substituted olefin compound, so that on dilution and application to plant foliage both glyphosate and the phenyl-substituted olefin compound are deposited simultaneously on the foliage. As indicated above, the phenyl-substituted olefin compound, if water-soluble, can be dissolved in the same aqueous solution as the glyphosate salt; however more commonly, the phenyl-substituted olefin compound is only sparingly water-soluble and is held in stable dispersion in the aqueous solution by means of one or more emulsifiers. If desired, a sparingly water-soluble phenyl-substituted olefin compound can be dissolved in an oil or organic solvent that is then blended with one or more emulsifiers and an aqueous solution of glyphosate salt to form a stable emulsion having glyphosate primarily in the aqueous phase and the phenyl-substituted olefin compound primarily in the oil phase.

Thus a particular embodiment of the invention is a concentrate composition that is an emulsion having an aqueous phase and an oil phase. Glyphosate or another water-soluble exogenous chemical substance is present primarily in the aqueous phase of the emulsion and a phenyl-substituted olefin compound is present primarily in the oil phase. The concentrate composition further comprises one or more surfactants in an amount sufficient to emulsify the oil phase in the aqueous phase. Such a concentrate can be a water-in-oil, oil-in-water or water-in-oil-in-water (multiple) emulsion; however it is preferred that the emulsion be one that is readily dilutable in water.

Glyphosate concentrates of the invention, whether aqueous solutions or emulsions, can contain about 50 to about 500 grams per liter of glyphosate, expressed as acid equivalent (g a.e./l). Higher glyphosate concentrations, for example about 300 to about 500 g a.e./l, are preferred.

Glyphosate salts are alternatively formulated as water-soluble or water-dispersible compositions, in the form for example of powders, granules, pellets or tablets. Such compositions are often known as dry formulations, although the term "dry" should not be understood in this context to imply the complete absence of water. Typically, dry formulations contain less than about 5% by weight of water, for example about 0.5% to about 2% by weight of water. Such formulations are intended for dissolution or dispersion in water at the point of use.

The present invention encompasses water-soluble or water-dispersible dry formulations containing, in addition to a glyphosate salt, an appropriate amount of a phenyl-substituted olefin compound, so that on application to plant foliage both glyphosate and the phenyl-substituted olefin compound are deposited simultaneously on the foliage. Even if an emulsifier is not necessary to make a stable dry glyphosate formulation containing a sparingly water-soluble phenyl-substituted olefin compound, it is preferred to include one or more emulsifers in the formulation to enhance dispersion and stability of the spray composition formed when the dry formulation is added to water. Contemplated dry glyphosate formulations can contain about 5% to about 80% by weight of glyphosate, expressed as acid equivalent (% a.e.). Higher glyphosate concentrations within the above range, for example about 50% to about 80% a.e., are preferred. Especially useful salts of glyphosate for making dry formulations are sodium and ammonium salts.

Plant treatment compositions and liquid and dry concentrate compositions of the invention can optionally contain, in addition to an exogenous chemical substance and a phenyl-substituted olefin compound, one or more desired excipient ingredients. Especially useful excipient ingredients, at least in the case of glyphosate compositions, are surfactants, which assist in retention of aqueous spray solutions on the relatively hydrophobic surfaces of plant leaves, as well as helping the glyphosate, and perhaps the phenyl-substituted olefin compound, to penetrate the waxy outer layer (cuticle) of the leaf and thereby contact living tissues within the leaf. Surfactants can perform other useful functions as well, including serving as emulsifiers to permit the phenyl-substituted olefin compound to be incorporated in a stable homogeneous formulation, as indicated above.

There is no restriction in the type or chemical class of surfactant that can be used in compositions of the invention. Nonionic, anionic, cationic and amphoteric types, or combinations of more than one of these types, are all useful in particular situations. For glyphosate compositions, however, it is generally preferred that at least one of the surfactants, if any, present should be other than anionic, i.e. at least one of the surfactants should be nonionic, cationic or amphoteric.

Many surfactants useful herein have a chemical structure that comprises one or more moieties each consisting of a single $C_{2-4}$ alkylene oxide unit or a polymerized or copolymerized chain of $C_{2-4}$ alkylene oxide units. Such surfactants are referred to as polyoxyalkylene surfactants and include nonionic, anionic, cationic and amphoteric types. Polyoxyalkylene surfactants useful in presently contemplated compositions contain about 2 to about 100 $C_{2-4}$ alkylene oxide units. In preferred polyoxyalkylene surfactants the alkylene oxide units form one or more chains of either ethylene oxide or copolymerized ethylene oxide and propylene oxide, each chain of alkylene oxide units having a terminal hydrido group or a $C_{1-4}$ alkyl or $C_{1-4}$ alkanoyl end-cap.

Hydrophobic moieties of surfactants useful in compositions of the invention can be essentially hydrocarbon based, in which case the hydrophobic moieties are typically $C_{8-24}$, preferably $C_{12-18}$, alkyl, alkenyl, alkylaryl, alkanoyl or alkenoyl chains. These chains can be linear or branched. Alternatively, the hydrophobic moieties can contain silicon atoms, for example in the form of siloxane groups such as heptamethyltrisiloxane groups, or fluorine atoms, for example as partially-fluorinated alkyl or perfluoroalkyl chains.

Among nonionic surfactants, especially preferred classes include polyoxyethylene alkyl, alkenyl or alkylaryl ethers, such as ethoxylated primary or secondary alcohols or alkylphenols, polyoxyethylene alkyl or alkenyl esters, such as ethoxylated fatty acids, polyoxyethylene sorbitan alkyl esters, glyceryl alkyl esters, sucrose esters, alkyl polyglycosides, and the like. Representative specific examples of such nonionic surfactants include polyoxyethylene (9) nonylphenol, Neodol™ 25-7 of Shell (a polyoxyethylene (7) $C_{12-15}$ linear primary alcohol), Tergitol™ 15-S-9 of Union Carbide (a polyoxyethylene (9) $C_{12-15}$ secondary alcohol), Tween™ 20 of ICI (a polyoxyethylene (20) sorbitan monolaurate) and Agrimul™ PG-2069 of Henkel (a $C_{9-11}$ alkyl polyglucoside).

Among cationic surfactants, especially preferred classes include polyoxyethylene tertiary alkylamines or alkenylamines, such as ethoxylated fatty amines, quaternary ammonium surfactants, polyoxyethylene alkyletheramines, and the like. Representative specific examples of such cationic surfactants include polyoxyethylene (5) cocoamine, polyoxyethylene (15) tallowamine, distearyldimethylammonium chloride, cetyltrimethylammonium bromide, methyl bis(2-hydroxyethyl)cocoammonium chloride, N-dodecylpyridine chloride and polyoxypropylene (8) ethoxytrimethylammonium chloride. Particularly preferred polyoxyethylene alkyletheramines are those disclosed in PCT Publication No. WO 96/32839. Many cationic quaternary ammonium surfactants of diverse structures are known in the art to be useful in combination with glyphosate and other exogenous chemical substances and can be used in compositions contemplated herein; such quaternary ammonium surfactants have the formula

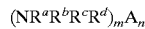

$(NR^aR^bR^cR^d)_m A_n$ where A is a suitable anion such as chloride, bromide, iodide, acetate, sulfate or phosphate, m and n are integers such that the positive electrical charges on cations $(NR^aR^bR^cR^d)$ balance the negative electrical charges on anions A, and options for $R^a$, $R^b$, $R^c$ and $R^d$ include, without limitation:

(i) $R^a$ is benzyl or $C_{8-24}$, preferably $C_{12-24}$, alkyl or alkenyl, and $R^b$, $R^c$ and $R^d$ are independently $C_{1-4}$ alkyl, preferably methyl;

(ii) $R^a$ and $R^b$ are independently $C_{8-24}$, preferably $C_{12-18}$, alkyl or alkenyl, and $R^c$ and $R^d$ are independently $C_{1-4}$ alkyl, preferably methyl;

(iii) $R^a$ is $C_{8-24}$, preferably $C_{12-18}$, alkyl or alkenyl, $R^b$ is a polyoxyalkylene chain having about 2 to about 100 $C_{2-4}$ alkylene oxide units, preferably ethylene oxide units, and $R^c$ and $R^d$ are independently $C_{1-4}$ alkyl, preferably methyl;

(iv) $R^a$ is $C_{8-24}$, preferably $C_{12-18}$, alkyl or alkenyl, $R^b$ and $R^c$ are polyoxyalkylene chains having in total about 2 to about 100 $C_{2-4}$ alkylene oxide units, preferably ethylene oxide units, and Rd is $C_{1-4}$ alkyl, preferably methyl; or (v) $R^a$ is a polyoxyalkylene chain having about 2 to about 100 $C_{2-4}$ alkylene oxide units in which $C_{3-4}$ alkylene oxide units, preferably propylene oxide units, predominate and $R^b$, $R^c$ and $R^d$ are independently $C_{1-4}$ alkyl, preferably methyl or ethyl. Particularly preferred quaternary ammonium surfactants of this type are those disclosed in U.S. Pat. No. 5,464,807 to Claude et al.

In one embodiment, the anion A associated with such a quaternary ammonium surfactant can be the exogenous chemical substance itself in anionic form, for example a glyphosate anion.

Among amphoteric surfactants, including as is customary in the art surfactants more correctly described as zwitterionic, especially preferred classes include polyoxyethylene alkylamine oxides, alkylbetaines, alkyl-substituted amino acids and the like. Representative examples of such amphoteric surfactants include dodecyldimethylamine oxide, polyoxyethylene (2) cocoamine oxide and stearyldimethylbetaine.

Standard reference sources from which one of skill in the art can select suitable surfactants, without limitation to the above mentioned classes, include *Handbook of Industrial Surfactants*, Second Edition (1997) published by Gower, *McCutcheon's Emulsifiers and Detergents*, North American and International Editions (1997) published by MC Publishing Company, and *International Cosmetic Ingredient Dictionary*, Sixth Edition (1995) Volumes 1 and 2, published by the Cosmetic, Toiletry and Fragrance Association.

Other optional components of compositions of the invention include agents to modify color, viscosity, gelling properties, freezing point, hygroscopicity, caking behavior, dissolution rate, dispersibility, or other formulation characteristics.

The phenyl-substituted olefin compound can be provided in a separate composition, as an alternative to providing that compound as a component of the exogenous chemical formulation. In such a case, the composition comprising the phenyl-substituted olefin compound is typically tank-mixed with the exogenous chemical substance. A tank-mixed composition is prepared by the user as a single spray composition by dilution, dissolution or dispersion in water of two concentrate compositions, one containing the exogenous chemical substance and the other containing the phenyl-substituted olefin compound. The two concentrate compositions can be supplied independently or in a twin-pack or other form of combined packaging.

A particular embodiment of the invention is a concentrate composition comprising a phenyl-substituted olefin compound together with one or more surfactants; this composition being useful as an adjuvant for tank-mixing with an exogenous chemical substance prior to application to plant foliage. Where the phenyl-substituted olefin compound composition is to be used as an adjuvant to glyphosate, it is preferred that at least one surfactant, if any, in the composition should other than anionic. Preferred classes of surfactant are as listed above.

A phenyl-substituted olefin compound, or composition thereof, can illustratively be used according to a process provided herein in tank-mixture with a commercial formulation of glyphosate. Examples of such formulations include, without restriction, those sold by Monsanto Company as ROUNDUP®, ROUNDUP® ULTRA, ROUNDUP® CT, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Zeneca Limited as TOUCHDOWN® herbicide, which contains glyphosate as its trimethylsulfonium salt.

Alternatively, a phenyl-substituted olefin compound, or composition thereof, can illustratively be used according to the process provided herein as a pre-treatment or post-treatment before or after foliar application of any commercial formulation of glyphosate including, without restriction, those exemplified above. When a phenyl-substituted olefin compound is applied to foliage as a pre-treatment or post-treatment, the interval between this treatment and application of the glyphosate or other exogenous chemical substance should be such as to allow the phenyl-substituted olefin compound to enhance reliability of effectiveness of the exogenous chemical substance. Such an interval is described herein as an "effective time period". The duration of an effective time period varies depending on species of plant, on the particular exogenous chemical substance and on the particular phenyl-substituted olefin compound, among other factors. In the case of glyphosate, for example, an interval of 0 to about 96 hours can be an effective time period, but preferably the interval is 0 to about 24 hours. Thus, an embodiment of the invention is a process for enhancing reliability of biological effectiveness of an exogenous chemical substance comprising steps (a) and (b) as hereinbefore defined, wherein step (b) occurs within about 24 hours before or after step (a). Where sequential application is employed, a preferred sequence is for the exogenous chemical substance to be applied within about 24 hours after the phenyl-substituted olefin compound. An optimum interval can readily be determined for any combination of exogenous chemical substance, phenyl-substituted olefin compound and plant species by preliminary tests.

The selection of application rates for a specific exogenous chemical substance that are biologically effective is also within the skill of the ordinary agricultural technician. One of skill in the art will likewise recognize that individual plant conditions, weather and growing conditions, as well as the specific exogenous chemical substance selected, can affect the results achieved in practicing the process of the present invention. Where the exogenous chemical substance is glyphosate, much information is available in published literature about appropriate application rates. Over two decades of glyphosate use and published studies relating to such use have provided abundant information from which a weed control practitioner can select glyphosate application rates that are herbicidally effective on particular species at particular growth stages in particular environmental conditions.

A process of the present invention where the exogenous chemical substance is glyphosate, more particularly a water-soluble glyphosate salt, is applicable to any and all plant species on which glyphosate is biologically effective as a herbicide or plant growth regulator. This encompasses a very wide variety of plant species worldwide. Likewise, compositions of the invention containing glyphosate can be applied to any and all plant species on which glyphosate is biologically effective. For example, where the exogenous chemical substance is glyphosate, annual broadleaf species on which the process and compositions of the invention can be employed include, without limitation, *Abutilon theophrasti* (velvetleaf), Amaranthus spp. (pigweed), Borreria spp. (buttonweed), Brassica spp. (oilseed rape, canola, indian mustard, etc.), Commelina spp. (commelina), Erodium spp. (filaree), Helianthus spp. (sunflower), Ipomoea spp. (morningglory), *Kochia scoparia* (kochia), Malva spp. (mallow), Polygonum spp. (wild buckwheat, smartweed, etc.), Portulaca spp. (purslane), Salsola spp. (russian thistle), Sida spp. (sida), *Sinapis arvensis* (wild mustard), and Xanthium spp. (cocklebur).

Again where the exogenous chemical substance is glyphosate, annual narrowleaf species on which the process and compositions of the invention can be employed include, without limitation, *Avena fatua* (wild oat), Axonopus spp. (carpetgrass), *Bromus tectorum* (downy brome), Digitaria spp. (crabgrass), *Echinochloa crus-galli* (barnyardgrass), *Eleusine indica* (goosegrass), *Lolium multiflorum* (annual ryegrass), *Oryza sativa* (rice), *Ottochloa nodosa* (ottochloa), *Paspalum notatum* (bahiagrass), Phalaris spp. (canarygrass), Setaria spp. (foxtail), *Triticum aestivum* (wheat) and *Zea mays* (corn or maize).

Again where the exogenous chemical substance is glyphosate, perennial broadleaf species on which the process and compositions of the invention can be employed include, without limitation, Artemisia spp. (mugwort), Asclepias spp. (milkweed), *Cirsium arvense* (canada thistle), *Convolvulus arvensis* (field bindweed) and Pueraria spp. (kudzu).

Again where the exogenous chemical substance is glyphosate, perennial narrowleaf species on which the process and compositions of the invention can be employed include, without limitation, Brachiaria spp. (brachiaria), *Cynodon dactylon* (bermudagrass), *Cyperus esculentus* (yellow nutsedge), *Cyperus rotundus* (purple nutsedge), *Elymus repens* (quackgrass or couch), *Imperata cylindrica* (cogongrass or lalang), *Lolium perenne* (perennial ryegrass), *Panicum maximum* (guineagrass), *Paspalum dilatatum* (dallisgrass), Phragmites spp. (reed), *Sorghum halepense* Oohnsongrass) and Typha spp. (cattail).

Again where the exogenous chemical substance is glyphosate, other perennial species not listed above on which the process and compositions of the invention can be employed include, without limitation, Equisetum spp. (horsetail), *Pteridium aquilinum* (bracken), Rubus spp. (blackberry) and *Ulex europaeus* (gorse).

A phenyl-substituted olefin compound is particularly useful in a process of the invention at rates of about 0.25 to about 250 g/ha, preferably about 1 to about 25 g/ha, provided such rates are insufficient to antagonize biological effectiveness of the exogenous chemical substance. Several phenyl-substituted olefin compounds have been found to be antagonistic to glyphosate, i.e. to reduce the herbicidal effectiveness of glyphosate, if used for example at a rate of 50 g/ha or higher. Antagonism due to a phenyl-substituted olefin compound at a given rate can be readily ascertained under the conditions of use by means of standard test procedures well known to those of skill in the art, involving comparison of biological effectiveness of an exogenous chemical substance in the presence and absence of the phenyl-substituted olefin compound at the rate in question.

In a particularly useful composition of the invention, a phenyl-substituted olefin compound is present in an amount such that, when the composition is applied to foliage of a plant at a biologically effective rate of the exogenous chemical substance, the phenyl-substituted olefin compound is applied at a rate of about 0.25 to about 250 g/ha, preferably about 1 to about 25 g/ha, again provided such rates are insufficient to antagonize biological effectiveness of the exogenous chemical substance.

When a phenyl-substituted olefin compound is coformulated with glyphosate, the weight/weight ratio of phenyl-substituted olefin compound to glyphosate acid equivalent is preferably about 1:500 to about 1:5, for example about 1:200 to about 1:10.

Such low ratios of phenyl-substituted olefin compound to exogenous chemical substance mean that the phenyl-substituted olefin compound can generally be included in a concentrate formulation while still enjoying the benefits of very high loading of active ingredient (i.e. exogenous chemical substance) in the concentrate formulation. For example, in the case of an aqueous solution or emulsion concentrate formulation of a water-soluble glyphosate salt such as the isopropylammonium or trimethylsulfonium salt, a useful amount, for example about 1 to about 5 g/l, of a phenyl-substituted olefin compound can be included in the presence of a high concentration, for example about 350 to about 500 g a.e./l, of glyphosate. Especially high loadings of glyphosate, for example about 450 to about 500 g a.e./l, in an aqueous solution or emulsion concentrate formulation are often achievable only when the amount of surfactant in the formulation is reduced below the levels normally associated with consistent, reliable herbicidal performance; it is in this very situation where particularly great benefits can be obtained by including a small amount of a phenyl-substituted olefin compound.

A particular embodiment of the present invention is a herbicidal process comprising the steps of (a) mixing together (i) α-methyl-trans-cinnamaldehyde, (ii) an alkali metal, ammonium, $C_{1-16}$ alkylammonium, $C_{1-16}$ alkanolammonium or $C_{1-16}$ alkylsulfonium salt of N-phosphonomethylglycine, (iii) one or more surfactants in a total surfactant amount sufficient to emulsify the α-methyl-trans-cinnamaldehyde, and (iv) water, to form a concentrate, (b) dispersing the concentrate in water to form a spray composition in which the α-methyl-trans-cinnamaldehyde is present in an amount sufficient to provide a rate of about 1 to about 25 g/ha and the salt of N-phosphonomethylglycine is present in a herbicidally effective amount, and (c) spraying the spray composition on to foliage of a plant.

Preferably at least one of the surfactants used in the above process is a cationic surfactant selected from polyoxyalkylene tertiary alkylamines and alkenylamines, quaternary ammonium surfactants and polyoxyalkylene alkyletheramines.

Another particular embodiment of the present invention is a concentrate herbicidal composition comprising (i) about 1 to about 5 g/l of α-methyl-trans-cinnamaldehyde, (ii) about 350 to about 500 g a.e./l, most preferably about 450 to about 500 g a.e./l, of an alkali metal, ammonium, $C_{1-16}$ alkylammonium, $C_{1-16}$ alkanolammonium or $C_{1-16}$ alkylsulfonium salt of N-phosphonomethylglycine, (iii) one or more surfactants in a total surfactant amount sufficient to emulsify the α-methyl-trans-cinnamaldehyde, and (iv) water.

Preferably at least one of the surfactants in such a composition is a cationic surfactant selected from polyoxyalkylene tertiary alkylamines and alkenylamines, quaternary ammonium surfactants and polyoxyalkylene alkyletheramines. In this embodiment, the weight/weight ratio of α-methyl-trans-cinnamaldehyde to N-phosphonomethylglycine acid equivalent is preferably about 1:200 to about 1:100.

Certain phenyl-substituted olefin compounds possess a characteristic odor, which in most cases is organoleptically acceptable, often pleasant or attractive. For example, a-methyl-trans-cinnamaldehyde has a characteristic aroma of cinnamon. It has been found that even at the low concentrations of such phenyl-substituted olefin compounds needed to provide the desired enhancement in reliability of effectiveness of a composition containing an exogenous chemical substance, a characteristic odor is imparted to the composition. In the case of glyphosate compositions, this is of particular utility when a glyphosate salt having itself an unpleasant odor is being used, as the unpleasant odor is to some extent masked or counteracted by the more acceptable odor of the phenyl-substituted olefin compound. An example of this benefit is provided by an aqueous concentrate of the trimethylsulfonium salt of glyphosate containing about 0.25 to about 250 g/l, preferably about I to about 25 g/l, of a cinnamaldehyde derivative such as α-methyl-trans-cinnamaldehyde.

Even where a non-odoriferous exogenous chemical substance, such as for example the isopropylammonium salt of glyphosate, is being used, there can be value in including in a formulation therewith a phenyl-substituted olefin compound, for example a cinnamaldehyde derivative such as (x-methyl-trans-cinnamaldehyde, having an organoleptically acceptable odor. Such value arises not only from the enhancement in reliability of effectiveness of the exogenous chemical substance that can be expected, but also from the instant recognizability of the formulation by sense of smell. This recognizability assists in prevention of errors in the field whereby the wrong chemical or formulation is applied, or whereby a spray tank contains a residue of a previously applied formulation. In this regard, it is noted that of all the senses, the sense of smell has the most immediate effect in raising awareness of the presence of an undesired material.

EXAMPLES

The following Examples are provided for illustrative purposes only and are not intended to limit the scope of the present invention. In the tables below Et=ethyl, Me=methyl, cPr=cyclopropyl and Ph=phenyl.

Phenyl-substituted olefin compounds of formula (I) above used in the Examples have substituents as follows:

| Compound | $R^2$ | $R^3$ | $R^4$ | $R^5$ | $R^6$ | $R^7$ | $R^8$ | $R^9$ |
|---|---|---|---|---|---|---|---|---|
| 1 | OH | H | H | H | H | H | COOH | H |
| 2 | OMe | H | H | H | H | H | CHO | H |
| 3 | H | OH | OMe | H | H | H | COOH | H |
| 4 | H | OH | OH | H | H | H | COOH | H |
| 5 | H | OMe | OH | OMe | H | H | COOH | H |
| 7 | H | OMe | OH | H | H | H | CHO | H |
| 9 | H | H | OH | H | H | H | COOH | H |
| 10 | H | H | OMe | H | H | H | CN | H |
| 11 | H | H | Me | H | H | H | CN | CO(4-Me)Ph |
| 12 | H | H | H | H | H | H | COOCH$_2$CH:CH$_2$ | H |
| 14 | H | H | H | H | H | H | CHO | Amyl |
| 15 | H | H | H | H | H | H | CHO | Butyl |
| 16 | H | H | H | H | H | H | CHO | Hexyl |
| 17 | H | H | H | H | H | H | CHO | Me |
| 18 | H | H | OMe | H | H | H | COEt | H |
| 19 | H | H | H | H | H | H | COOCH$_2$Ph | H |
| 22 | H | H | H | H | H | H | CONHN:CH(4-NHCOMe)Ph | H |
| 23 | H | H | H | H | H | H | CONHN:CH(4-OMe)Ph | H |
| 24 | H | H | H | H | H | H | CN | H |
| 25 | H | H | H | H | H | H | CH$_2$OCOMe | H |
| 26 | H | H | H | H | H | H | CH$_2$OH | H |
| 27 | H | OMe | OH | H | H | H | CH$_2$OH | H |
| 32 | H | H | NO$_2$ | H | H | H | COOEt | H |
| 33 | H | H | H | H | H | H | COOEt | H |
| 34 | H | H | H | H | H | H | CH$_2$:CH(CN)-COOMe | H |
| 35 | H | OMe | OH | H | H | H | COOEt | H |
| 36 | H | OMe | OH | H | H | H | Me | H |
| 37 | H | H | H | H | H | Me | COOMe | H |
| 38 | H | H | H | H | H | H | COOMe | H |
| 39 | H | H | H | H | H | H | COOPh | H |
| 40 | H | H | H | H | H | H | H | H |
| 42 | H | H | H | H | H | H | COOH | H |
| 43 | H | OMe | OH | H | H | H | COOH | H |
| 45 | H | H | H | H | H | H | COPh | H |
| 46 | H | H | H | H | H | H | CHO | H |
| 47 | H | H | H | H | H | H | CH$_2$CH$_2$OH | H |
| 56 | H | OMe | OH | H | H | H | COMe | H |
| 57 | H | OH | OEt | H | H | H | Me | H |
| 58 | H | H | NO$_2$ | H | H | H | COOMe | COOMe |
| 59 | H | H | OMe | H | H | H | Me | H |
| 64 | H | H | H | H | H | H | COMe | H |
| 81 | H | H | H | H | H | H | COMe | Me |
| 98 | H | H | H | H | H | cPr | CN | CN |
| 104 | H | H | OMe | H | H | H | H | H |
| 108 | H | OMe | OMe | H | H | H | Me | H |
| 109 | H | OCH$_2$O | | H | H | H | COOH | H |
| 110 | H | OCH$_2$O | | H | H | H | COPh | H |
| 111 | H | OCH$_2$O | | H | H | H | CO(4-F)Ph | H |
| 112 | H | OCH$_2$O | | H | H | H | CO(4-Br)Ph | H |
| 113 | H | OCH$_2$O | | H | H | H | CO(4-Me)Ph | H |
| 114 | H | OCH$_2$O | | H | H | H | Me | H |

Compound 8 has formula (I) above wherein $R^2$, $R^3$, $R^4$, $R^5$, $R^6$ are each hydrido groups, $R^7$ and $R^8$ together with the carbon atoms linked by the ethylenic double bond of structure (I) form a cyclopentenedione ring as depicted in formula (III), $R^9$ is a hydroxy group and $R^{10}$ is a hydrido group.

Phenyl-substituted olefin compounds of formula (II) above used in the Examples have substituents as follows:

| Compound | $R_2$ | $R_3$ | $R_4$ | $R_5$ | $R_6$ | $R_7$ | $R_8$ | $R_9$ |
|---|---|---|---|---|---|---|---|---|
| 103 | H | OMe | OH | OMe | H | H | H | H |
| 105 | H | OMe | OH | H | H | H | H | H |
| 106 | H | H | OMe | H | H | H | H | H |
| 107 | H | OMe | OMe | H | H | H | H | H |
| 106 | H | OCH$_2$O | | H | H | H | H | H |

Example 1

A short-term whole plant assay was used to evaluate the effect of phenyl-substituted olefin compounds on the herbicidal performance of a glyphosate formulation on a test species, barley (Hordeum vulgare cv. Perry). The glyphosate formulation used was an aqueous concentrate containing 41% by weight of the isopropylammonium salt of glyphosate and 15% by weight of a surfactant (MON 0818 of Monsanto Company) based on polyoxyethylene (15) tallowamine, which has an average of 15 moles of ethylene oxide per mole of tallowamine. This aqueous concentrate has a glyphosate acid equivalent concentration of 360 g a.e./l.

Uniformly sized seeds of barley were planted, three per pot, in 50 mm square pots containing a soil mix prefertilized with a 14-14-14 NPK slow release fertilizer at a rate of 3.5 kg/m$^3$. Pots were placed in a greenhouse with sub-irrigation where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27–29° C. during the day and 18–21° C. during the night. Plants were sub-irrigated throughout the assay to ensure adequate soil moisture levels.

After emergence of the barley, seedlings were thinned to two per pot to achieve best possible uniformity. Pots were then assigned to different treatments in a fully randomized experimental design with 6 replications. A set of pots was left untreated as a reference against which the effects of the treatments could later be evaluated.

About 9 days after planting, treatments were applied by spraying with a track sprayer fitted with a TeeJet 9501E flat fan nozzle calibrated to deliver a spray volume of 187 l/ha at a pressure of 166 kPa. The glyphosate formulation, diluted to the required degree in water as described below, was applied alone at the three rates indicated, and, at the middle rate only, in mixture with each phenyl-substituted olefin compound being tested. The required degree of dilution for the glyphosate formulation was calculated from the equation $$A = RSNC$$

where A is the volume in milliliters (ml) of the glyphosate formulation to be added to the spray mixture being prepared, R is the desired glyphosate rate in grams of acid equivalent per hectare (g a.e./ha), S is the total volume in milliliters (ml) of spray mixture being prepared, V is the application rate in liters per hectare (l/ha) of spray mixture, conventionally referred to as "spray volume", and C is the concentration of glyphosate in grams of acid equivalent per liter (g a.e./l) in the glyphosate formulation. In the present Example, V=187 and C=360.

In preparation of spray mixtures, each phenyl-substituted olefin compound, obtained from a commercial source, was first dissolved in a minimal quantity of a suitable solvent, which was dimethyl sulfoxide except where otherwise noted below. The volume of phenyl-substituted olefin compound solution to be added to the spray mixture was determined by a calculation similar to that for the volume of glyphosate formulation, above. After treatment, pots were returned to the greenhouse.

Two days after treatment, all plants were cut at a height of I cm above the surface of the growing medium, and were then permitted to regrow from the base. Height of regrowth was measured after the time interval indicated (typically about 5 days after treatment). Measurements were taken from the point of cutting to the tip of the regrown shoot. Each plant (12 per treatment) was individually measured. A mean of regrowth heights of all plants receiving each treatment was calculated.

The assay was performed several times with different phenyl-substituted olefin compounds; regrowth height for a treatment illustrative of the process of the invention (glyphosate plus phenyl-substituted olefin compound) is always compared in the data tables below with regrowth height for glyphosate-only treated and untreated plants within the same assay.

TABLE 1.1

| Compound 1 | regrowth height (mm) Glyphosate rate (g a.e./ha) | | | |
|---|---|---|---|---|
| rate (g/ha) | 0 | 56 | 112 | 224 |
| 0 | 63 | 61 | 54 | 27 |
| 2 | | | 52 | |
| 20 | | | 39 | |
| 50 | | | 38 | |

Compound 1 at 20 g/ha and 50 g/ha in mixture with glyphosate enhanced the degree of regrowth reduction over that obtained with the same rate of glyphosate alone. At 2 g/ha, compound 1 failed to enhance to a significant degree the herbicidal effectiveness of glyphosate in this assay.

TABLE 1.2

| Compound 2 | regrowth height (mm) Glyphosate rate (g a.e./ha) | | | |
|---|---|---|---|---|
| rate (g/ha) | 0 | 56 | 112 | 224 |
| 0 | 55 | 55 | 55 | 25 |
| 20 | | | 59 | |
| 200 | 60 | | 46 | |

Compound 2 at 200 g/ha in mixture with glyphosate enhanced the degree of regrowth reduction over that obtained with the same rate of glyphosate alone. At 20 g/ha, compound 2 failed to enhance the herbicidal effectiveness of glyphosate in this assay.

TABLE 1.3

| Compound 3 | regrowth height (mm) | | | |
|---|---|---|---|---|
| | Glyphosate rate (g a.e./ha) | | | |
| rate (g/ha) | 0 | 56 | 112 | 224 |
| 0 | 55 | 52 | 52 | 25 |
| 2 | | | 49 | |
| 20 | | | 45 | |
| 50 | | | 57 | |

Compound 3 at 2 g/ha and 20 g/ha in mixture with glyphosate slightly enhanced the degree of regrowth reduction over that obtained with the same rate of glyphosate alone. At 50 g/ha, compound 3 failed to enhance the herbicidal effectiveness of glyphosate in this assay.

TABLE 1.4

| Compound 4 | regrowth height (mm) | | | |
|---|---|---|---|---|
| | Glyphosate rate (g a.e./ha) | | | |
| rate (g/ha) | 0 | 56 | 112 | 224 |
| 0 | 63 | 61 | 54 | 27 |
| 2 | | | 41 | |
| 20 | | | 51 | |
| 50 | | | 43 | |

Compound 4 at least at 2 g/ha and 50 g/ha in mixture with glyphosate enhanced the degree of regrowth reduction over that obtained with the same rate of glyphosate alone.

TABLE 1.5

| Compound 4 | regrowth height (mm) | | | |
|---|---|---|---|---|
| | Glyphosate rate (g a.e./ha) | | | |
| rate (g/ha) | 0 | 56 | 112 | 224 |
| 0 | 63 | 59 | 56 | 36 |
| 2 | | | 45 | |
| 20 | | | 54 | |
| 50 | | | 45 | |

Compound 4 at least at 2 g/ha and 50 g/ha in mixture with glyphosate enhanced the degree of regrowth reduction over that obtained with the same rate of glyphosate alone.

TABLE 1.6

| Compound 5 | regrowth height (mm) | | | |
|---|---|---|---|---|
| | Glyphosate rate (g a.e./ha) | | | |
| rate (g/ha) | 0 | 56 | 112 | 224 |
| 0 | 63 | 61 | 54 | 27 |
| 2 | | | 35 | |
| 20 | | | 44 | |
| 50 | | | 45 | |

Compound 5 at 2 g/ha, 20 g/ha and 50 g/ha in mixture with glyphosate enhanced the degree of regrowth reduction over that obtained with the same rate of glyphosate alone, the strongest enhancement being noted at the 2 g/ha rate of compound 5.

TABLE 1.7

| Compound 5 | regrowth height (mm) | | | |
|---|---|---|---|---|
| | Glyphosate rate (g a.e./ha) | | | |
| rate (g/ha) | 0 | 56 | 112 | 224 |
| 0 | 55 | 52 | 52 | 25 |
| 2 | | | 43 | |
| 20 | | | 45 | |
| 50 | | | 51 | |

Compound 5 at 2 g/ha and 20 g/ha in mixture with glyphosate slightly enhanced the degree of regrowth reduction over that obtained with the same rate of glyphosate alone. At 50 g/ha, compound 5 failed to enhance to a significant degree the herbicidal effectiveness of glyphosate in this assay.

TABLE 1.8

| Compound 5 | regrowth height (mm) | | | |
|---|---|---|---|---|
| | Glyphosate rate (g a.e./ha) | | | |
| rate (g/ha) | 0 | 56 | 112 | 224 |
| 0 | 57 | 56 | 43 | 24 |
| 2 | | | 33 | |
| 20 | | | 42 | |
| 50 | | | 38 | |

Compound 5 at 2 g/ha and 50 g/ha in mixture with glyphosate slightly enhanced the degree of regrowth reduction over that obtained with the same rate of glyphosate alone. At 50 g/ha, compound 5 failed to enhance to a significant degree the herbicidal effectiveness of glyphosate in this assay.

TABLE 1.9

| Compound 5 | regrowth height (mm) | | | |
|---|---|---|---|---|
| | Glyphosate rate (g a.e./ha) | | | |
| rate (g/ha) | 0 | 56 | 112 | 224 |
| 0 | 60 | 49 | 36 | 26 |
| 2 | | | 38 | |
| 20 | | | 39 | |
| 50 | | | 38 | |

Compound 5 at 2 g/ha, 20 g/ha or 50 g/ha in mixture with glyphosate did not in this assay enhance the degree of regrowth reduction over that obtained with the same rate of glyphosate alone. Note that glyphosate alone gave exceptionally great regrowth reduction in this assay.

TABLE 1.10

| Compound 7 | regrowth height (mm) | | | |
|---|---|---|---|---|
| | Glyphosate rate (g a.e./ha) | | | |
| rate (g/ha) | 0 | 56 | 112 | 224 |
| 0 | 52 | 55 | 53 | 34 |
| 2 | | | 49 | |
| 20 | | | 48 | |
| 50 | | | 43 | |

Compound 7 at 2 g/ha, 20 g/ha and 50 g/ha in mixture with glyphosate enhanced the degree of regrowth reduction over that obtained with the same rate of glyphosate alone. The most pronounced effect of compound 7 was seen at 50 g/ha.

TABLE 1.11

| Compound 8 rate (g/ha) | regrowth height (mm) Glyphosate rate (g a.e./ha) | | | |
|---|---|---|---|---|
| | 0 | 56 | 112 | 224 |
| 0 | 51 | 53 | 46 | 29 |
| 2 | | | 29 | |
| 20 | | | 30 | |
| 50 | | | 44 | |

Compound 8 at 2 g/ha and 20 g/ha in mixture with glyphosate enhanced the degree of regrowth reduction over that obtained with the same rate of glyphosate alone. At 50 g/ha, compound 8 failed to enhance to a significant degree the herbicidal effectiveness of glyphosate in this assay.

TABLE 1.12

| Compound 9 rate (g/ha) | regrowth height (mm) Glyphosate rate (g a.e./ha) | | | |
|---|---|---|---|---|
| | 0 | 56 | 112 | 224 |
| 0 | 63 | 61 | 54 | 27 |
| 2 | | | 41 | |
| 20 | | | 48 | |
| 50 | | | 43 | |

Compound 9 at 2 g/ha, 20 g/ha and 50 g/ha in mixture with glyphosate enhanced the degree of regrowth reduction over that obtained with the same rate of glyphosate alone.

TABLE 1.13

| Compound 9 rate (g/ha) | regrowth height (mm) Glyphosate rate (g a.e./ha) | | | |
|---|---|---|---|---|
| | 0 | 56 | 112 | 224 |
| 0 | 65 | 54 | 26 | 20 |
| 2 | | | 35 | |
| 20 | | | 35 | |
| 50 | | | 37 | |

Compound 9 at 2 g/ha, 20 g/ha or 50 g/ha in mixture with glyphosate did not in this assay enhance the degree of regrowth reduction over that obtained with the same rate of glyphosate alone. Note that glyphosate alone gave exceptionally great regrowth reduction this assay.

TABLE 1.14

| Compound 10 rate (g/ha) | regrowth height (mm) Glyphosate rate (g a.e./ha) | | | |
|---|---|---|---|---|
| | 0 | 56 | 112 | 224 |
| 0 | 60 | 60 | 44 | 31 |
| 2 | | | 38 | |
| 20 | | | 41 | |
| 50 | | | 48 | |

Compound 10 at 2 g/ha and 20 g/ha in mixture with glyphosate slightly enhanced the degree of regrowth reduction over that obtained with the same rate of glyphosate alone. At 50 g/ha, compound 10 failed to enhance the herbicidal effectiveness of glyphosate in this assay.

TABLE 1.15

| Compound 11 rate (g/ha) | regrowth height (mm) Glyphosate rate (g a.e./ha) | | | |
|---|---|---|---|---|
| | 0 | 112 | 224 | 448 |
| 0 | 54 | 59 | 39 | 36 |
| 20 | | | 27 | |
| 200 | 54 | | 28 | |

Compound 11 at both 20 g/ha and 200 g/ha in mixture with glyphosate enhanced the degree of regrowth reduction over that obtained with the same rate, or even two times that rate, of glyphosate alone.

TABLE 1.16

| Compound 11 rate (g/ha) | regrowth height (mm) Glyphosate rate (g a.e./ha) | | | |
|---|---|---|---|---|
| | 0 | 56 | 112 | 224 |
| 0 | 58 | 47 | 40 | 21 |
| 20 | | | 34 | |
| 200 | 58 | | 36 | |

Compound 11 at both 20 g/ha and 200 g/ha in mixture with glyphosate enhanced the degree of regrowth reduction over that obtained with the same rate of glyphosate alone.

TABLE 1.17

| Compound 12 rate (g/ha) | regrowth height (mm) Glyphosate rate (g a.e./ha) | | | |
|---|---|---|---|---|
| | 0 | 56 | 112 | 224 |
| 0 | 58 | 54 | 47 | 27 |
| 2 | | | 41 | |
| 20 | | | 37 | |
| 50 | | | 37 | |

Compound 12 at 2 g/ha, 20 g/ha and 50 g/ha in mixture with glyphosate enhanced the degree of regrowth reduction over that obtained with the same rate of glyphosate alone.

TABLE 1.18

| Compound 14 rate (g/ha) | regrowth height (mm) Glyphosate rate (g a.e./ha) | | | |
|---|---|---|---|---|
| | 0 | 56 | 112 | 224 |
| 0 | 65 | 60 | 45 | 28 |
| 20 | | | 33 | |
| 200 | 59 | | 31 | |

Compound 14 at both 20 g/ha and 200 g/ha in mixture with glyphosate enhanced the degree of regrowth reduction over that obtained with the same rate of glyphosate alone.

TABLE 1.19

| Compound 15 | regrowth height (mm) Glyphosate rate (g a.e./ha) | | | |
|---|---|---|---|---|
| rate (g/ha) | 0 | 56 | 112 | 224 |
| 0 | 55 | 56 | 43 | 32 |
| 2 | | | 40 | |
| 20 | | | 31 | |
| 50 | | | 38 | |

Compound 15 at 2 g/ha, 20 g/ha and 50 g/ha in mixture with glyphosate enhanced the degree of regrowth reduction over that obtained with the same rate of glyphosate alone, with the strongest effect being noted at the 20 g/ha rate of compound 15.

TABLE 1.20

| Compound 16 | regrowth height (mm) Glyphosate rate (g a.e./ha) | | | |
|---|---|---|---|---|
| rate (g/ha) | 0 | 56 | 112 | 224 |
| 0 | 70 | 62 | 54 | 25 |
| 20 | | | 55 | |
| 200 | 65 | | 38 | |

Compound 16 at 200 g/ha in mixture with glyphosate enhanced the degree of regrowth reduction over that obtained with the same rate of glyphosate alone. At 20 g/ha, compound 16 failed to enhance the herbicidal effectiveness of glyphosate in this assay.

TABLE 1.21

| Compound 17 | regrowth height (mm) Glyphosate rate (g a.e./ha) | | | |
|---|---|---|---|---|
| rate (g/ha) | 0 | 56 | 112 | 224 |
| 0 | 51 | 54 | 50 | 28 |
| 2 | | | 47 | |
| 20 | | | 53 | |
| 50 | | | 43 | |

Compound 17 at 50 g/ha in mixture with glyphosate slightly enhanced the degree of regrowth reduction over that obtained with the same rate of glyphosate alone. At 2 g/ha and 20 g/ha, compound 17 did not enhance to a significant degree the herbicidal effectiveness of glyphosate in this assay.

TABLE 1.22

| Compound 18 | regrowth-height (mm) Glyphosate rate (g a.e./ba) | | | |
|---|---|---|---|---|
| rate (g/ha) | 0 | 56 | 112 | 224 |
| 0 | 58 | 54 | 47 | 27 |
| 2 | | | 40 | |
| 20 | | | 36 | |
| 50 | | | 38 | |

Compound 18 at 2 g/ha, 20 g/ha and 50 g/ha in mixture with glyphosate enhanced the degree of regrowth reduction over that obtained with the same rate of glyphosate alone, with the strongest effect being noted at the 20 g/ha rate of compound 18.

TABLE 1.23

| Compound 19 | regrowth height (mm) Glyphosate rate (g a.e./ha) | | | |
|---|---|---|---|---|
| rate (g/ha) | 0 | 56 | 112 | 224 |
| 0 | 50 | 30 | 23 | 18 |
| 20 | | | 28 | |
| 200 | 43 | | 32 | |

Compound 19 at 20 g/ha or 200 g/ha in mixture with glyphosate did not in this assay enhance the degree of regrowth reduction over that obtained with the same rate of glyphosate alone. Note that glyphosate alone gave exceptionally great regrowth reduction, even at the lowest rate tested, in this assay.

TABLE 1.24

| Compound 19 | regrowth height (mm) Glyphosate rate (g a.e./ha) | | | |
|---|---|---|---|---|
| rate (g/ha) | 0 | 56 | 112 | 224 |
| 0 | 65 | 60 | 45 | 28 |
| 20 | | | 29 | |
| 200 | 45 | | 27 | |

Compound 19 at both 20 g/ha and 200 g/ha in mixture with glyphosate enhanced the degree of regrowth reduction over that obtained with the same rate of glyphosate alone. A degree of regrowth reduction was obtained similar to that given by glyphosate at twice the rate in the absence of compound 19.

TABLE 1.25

| Compound 19 | regrowth height (mm) Glyphosate rate (g a.e./ha) | | | |
|---|---|---|---|---|
| rate (g/ha) | 0 | 56 | 112 | 224 |
| 0 | 41 | 45 | 42 | 28 |
| 2 | | | 38 | |
| 20 | | | 43 | |
| 50 | | | 43 | |

Compound 19 at 2 g/ha in mixture with glyphosate slightly enhanced the degree of regrowth reduction over that obtained with the same rate of glyphosate alone. At 20 g/ha and 50 g/ha, compound 19 failed to enhance the herbicidal effectiveness of glyphosate in this assay.

TABLE 1.26

| Compound 22 | regrowth height (mm) Glyphosate rate (g a.e./ha) | | | |
|---|---|---|---|---|
| rate (g/ha) | 0 | 112 | 224 | 448 |
| 0 | 54 | 59 | 39 | 36 |
| 20 | | | 24 | |
| 200 | 50 | | 25 | |

Compound 22 at both 20 g/ha and 200 g/ha in mixture with glyphosate enhanced the degree of regrowth reduction over that obtained with the same rate, or even two times that rate, of glyphosate alone.

TABLE 1.27

| Compound 22 | regrowth height (mm) | | | |
|---|---|---|---|---|
| | Glyphosate rate (g a.e./ha) | | | |
| rate (g/ha) | 0 | 56 | 112 | 224 |
| 0 | 58 | 47 | 40 | 21 |
| 20 | | | 36 | |
| 200 | 57 | | 40 | |

Compound 22 at 20 g/ha in mixture with glyphosate slightly enhanced the degree of regrowth reduction over that obtained with the same rate of glyphosate alone. At 200 g/ha, compound 22 failed to enhance the herbicidal effectiveness of glyphosate in this assay.

TABLE 1.28

| Compound 23 | regrowth height (mm) | | | |
|---|---|---|---|---|
| | Glyphosate rate (g a.e./ha) | | | |
| rate (g/ha) | 0 | 112 | 224 | 448 |
| 0 | 54 | 59 | 39 | 36 |
| 20 | | | 27 | |
| 200 | 49 | | 28 | |

Compound 23 at both 20 g/ha and 200 g/ha in mixture with glyphosate enhanced the degree of regrowth reduction over that obtained with the same rate, or even two times that rate, of glyphosate alone.

TABLE 1.29

| Compound 23 | regrowth height (mm) | | | |
|---|---|---|---|---|
| | Glyphosate rate (g a.e./ha) | | | |
| rate (g/ha) | 0 | 56 | 112 | 224 |
| 0 | 58 | 47 | 40 | 21 |
| 20 | | | 28 | |
| 200 | 44 | | 44 | |

Compound 23 at 20 g/ha in mixture with glyphosate enhanced the degree of regrowth reduction over that obtained with the same rate of glyphosate alone. At 200 g/ha, compound 23 failed to enhance the herbicidal effectiveness of glyphosate in this assay.

TABLE 1.30

| Compound 24 | regrowth height (mm) | | | |
|---|---|---|---|---|
| | Glyphosate rate (g a.e./ha) | | | |
| rate (g/ha) | 0 | 112 | 224 | 448 |
| 0 | 54 | 59 | 39 | 36 |
| 20 | | | 29 | |
| 200 | 37 | | 23 | |

Compound 24 at both 20 g/ha and 200 g/ha in mixture with glyphosate enhanced the degree of regrowth reduction over that obtained with the same rate, or even two times that rate, of glyphosate alone.

TABLE 1.31

| Compound 24 | regrowth height (mm) | | | |
|---|---|---|---|---|
| | Glyphosate rate (g a.e./ha) | | | |
| rate (g/ha) | 0 | 56 | 112 | 224 |
| 0 | 58 | 47 | 40 | 21 |
| 20 | | | 28 | |
| 200 | 52 | | 30 | |

Compound 24 at both 20 g/ha and 200 g/ha in mixture with glyphosate enhanced the degree of regrowth reduction over that obtained with the same rate of glyphosate alone.

TABLE 1.32

| Compound 25 | regrowth height (mm) | | | |
|---|---|---|---|---|
| | Glyphosate rate (g a.e./ha) | | | |
| rate (g/ha) | 0 | 56 | 112 | 224 |
| 0 | 63 | 56 | 32 | 20 |
| 20 | | | 31 | |
| 200 | 48 | | 29 | |

Compound 25 at 20 g/ha or 200 g/ha in mixture with glyphosate did not enhance to a significant degree the herbicidal effectiveness of glyphosate in this assay.

TABLE 1.33

| Compound 25 | regrowth height (mm) | | | |
|---|---|---|---|---|
| | Glyphosate rate (g a.e./ha) | | | |
| rate (g/ha) | 0 | 56 | 112 | 224 |
| 0 | 61 | 60 | 55 | 28 |
| 2 | | | 36 | |
| 20 | | | 38 | |
| 50 | | | 39 | |

Compound 25 at 2 g/ha, 20 g/ha and 50 g/ha in mixture with glyphosate enhanced the degree of regrowth reduction over that obtained with the same rate of glyphosate alone.

TABLE 1.34

| Compound 26 | regrowth height (mm) | | | |
|---|---|---|---|---|
| | Glyphosate rate (g a.e./ha) | | | |
| rate (g/ha) | 0 | 56 | 112 | 224 |
| 0 | 63 | 56 | 32 | 20 |
| 20 | | | 38 | |
| 200 | 50 | | 30 | |

Compound 26 at 20 g/ha or 200 g/ha in mixture with glyphosate did not in this assay enhance the degree of regrowth reduction over that obtained with the same rate of glyphosate alone.

TABLE 1.35

| Compound 27 rate (g/ha) | regrowth height (mm) Glyphosate rate (g a.e./ha) | | | |
|---|---|---|---|---|
| | 0 | 56 | 112 | 224 |
| 0 | 52 | 55 | 53 | 34 |
| 2 | | | 33 | |
| 20 | | | 45 | |
| 50 | | | 53 | |

Compound 27 at 2 g/ha and 20 g/ha in mixture with glyphosate enhanced the degree of regrowth reduction over that obtained with the same rate of glyphosate alone, with the strongest enhancement being noted at the 2 g/ha rate of compound 27. At 50 g/ha, compound 27 failed to enhance the herbicidal effectiveness of glyphosate in this assay.

TABLE 1.36

| Compound 32 rate (g/ha) | regrowth height (mm) Glyphosate rate (g a.e./ha) | | | |
|---|---|---|---|---|
| | 0 | 56 | 112 | 224 |
| 0 | 61 | 61 | 52 | 28 |
| 2 | | | 45 | |
| 20 | | | 50 | |
| 50 | | | 45 | |

Compound 32 at least at 2 g/ha and 50 g/ha in mixture with glyphosate slightly enhanced the degree of regrowth reduction over that obtained with the same rate of glyphosate alone.

TABLE 1.37

| Compound 33 rate (g/ha) | regrowth height (mm) Glyphosate rate (g a.e./ha) | | | |
|---|---|---|---|---|
| | 0 | 56 | 112 | 224 |
| 0 | 70 | 62 | 54 | 25 |
| 20 | | | 34 | |
| 200 | 60 | | 46 | |

Compound 33 at both 20 g/ha and 200 g/ha in mixture with glyphosate enhanced the degree of regrowth reduction over that obtained with the same rate of glyphosate alone.

TABLE 1.38

| Compound 34 rate (g/ha) | regrowth height (mm) Glyphosate rate (g a.e./ha) | | | |
|---|---|---|---|---|
| | 0 | 56 | 112 | 224 |
| 0 | 50 | 48 | 35 | 28 |
| 2 | | | 30 | |
| 20 | | | 33 | |
| 50 | | | 34 | |

Compound 34 at 2 g/ha in mixture with glyphosate slightly enhanced the degree of regrowth reduction over that obtained with the same rate of glyphosate alone. At 20 g/ha and g/ha, compound 34 did not enhance to a significant degree the herbicidal effectiveness of glyphosate in this assay.

TABLE 1.39

| Compound 35 rate (g/ha) | regrowth height (mm) Glyphosate rate (g a.e./ha) | | | |
|---|---|---|---|---|
| | 0 | 56 | 112 | 224 |
| 0 | 41 | 45 | 42 | 28 |
| 2 | | | 45 | |
| 20 | | | 37 | |
| 50 | | | 38 | |

Compound 35 at 20 and 50 g/ha in mixture with glyphosate slightly enhanced the degree of regrowth reduction over that obtained with the same rate of glyphosate alone. At 2 g/ha, compound 35 failed to enhance the herbicidal effectiveness of glyphosate in this assay.

TABLE 1.40

| Compound 36 rate (g/ha) | regrowth height (mm) Glyphosate rate (g a.e./ha) | | | |
|---|---|---|---|---|
| | 0 | 56 | 112 | 224 |
| 0 | 65 | 60 | 41 | 19 |
| 20 | | | 64* | |
| 200 | 63 | | 36 | |

Compound 36 at 200 g/ha in mixture with glyphosate slightly enhanced the degree of regrowth reduction over that obtained with the same rate of glyphosate alone. It is believed that the treatment with 20 g/ha of compound 36 was accidentally applied without glyphosate and the data for this treatment (marked * in the table above) should be disregarded.

TABLE 1.41

| Compound 36 rate (g/ha) | regrowth height (mm) Glyphosate rate (g a.e./ha) | | | |
|---|---|---|---|---|
| | 0 | 56 | 112 | 224 |
| 0 | 63 | 61 | 54 | 27 |
| 2 | | | 41 | |
| 20 | | | 43 | |
| 50 | | | 45 | |

Compound 36 at 2 g/ha, 20 g/ha and 50 g/ha in mixture with glyphosate enhanced the degree of regrowth reduction over that obtained with the same rate of glyphosate alone.

TABLE 1.42

| Compound 36 rate (g/ha) | regrowth height (mm) Glyphosate rate (g a.e./ha) | | | |
|---|---|---|---|---|
| | 0 | 56 | 112 | 224 |
| 0 | 58 | 51 | 56 | 45 |
| 2 | | | 59 | |
| 20 | | | 56 | |
| 50 | | | 43 | |

Compound 36 at 50 g/ha in mixture with glyphosate enhanced the degree of regrowth reduction over that obtained with the same rate, or even two times that rate, of glyphosate alone. At 2 g/ha and 20 g/ha, compound 36 failed to enhance the herbicidal effectiveness of glyphosate in this assay.

TABLE 1.43

| Compound 37 rate (g/ha) | regrowth height (mm) Glyphosate rate (g a.e./ha) | | | |
|---|---|---|---|---|
| | 0 | 56 | 112 | 224 |
| 0 | 61 | 61 | 52 | 28 |
| 2 | | | 44 | |
| 20 | | | 35 | |
| 50 | | | 46 | |

Compound 37 at 2 g/ha, 20 g/ha and 50 g/ha in mixture with glyphosate enhanced the degree of regrowth reduction over that obtained with the same rate of glyphosate alone, with the strongest enhancement being noted at the 20 g/ha rate of compound 37.

TABLE 1.44

| Compound 38 rate (g/ha) | regrowth height (mm) Glyphosate rate (g a.e./ha) | | | |
|---|---|---|---|---|
| | 0 | 56 | 112 | 224 |
| 0 | 48 | 50 | 28 | 20 |
| 2 | | | 28 | |
| 20 | | | 24 | |
| 50 | | | 28 | |

Compound 38 at 20 g/ha in mixture with glyphosate slightly enhanced the degree of regrowth reduction over that obtained with the same rate of glyphosate alone. At 2 g/ha and 50 g/ha, compound 38 failed to enhance the herbicidal effectiveness of glyphosate in this assay.

TABLE 1.45

| Compound 39 rate (g/ha) | regrowth height (mm) Glyphosate rate (g a.e./ha) | | | |
|---|---|---|---|---|
| | 0 | 56 | 112 | 224 |
| 0 | 61 | 61 | 52 | 28 |
| 2 | | | 47 | |
| 20 | | | 52 | |
| 50 | | | 46 | |

Compound 39 at 2 and 50 g/ha in mixture with glyphosate slightly enhanced the degree of regrowth reduction over that obtained with the same rate of glyphosate alone. At 20 g/ha, compound 39 failed to enhance the herbicidal effectiveness of glyphosate in this assay.

TABLE 1.46

| Compound 40 rate (g/ha) | regrowth height (mm) Glyphosate rate (g a.e./ha) | | | |
|---|---|---|---|---|
| | 0 | 56 | 112 | 224 |
| 0 | 54 | 56 | 50 | 30 |
| 2 | | | 46 | |
| 20 | | | 43 | |
| 50 | | | 51 | |

Compound 40 at 2 g/ha and 20 g/ha in mixture with glyphosate slightly enhanced the degree of regrowth reduction over that obtained with the same rate of glyphosate alone. At 50 g/ha, compound 40 failed to enhance the herbicidal effectiveness of glyphosate in this assay.

TABLE 1.47

| Compound 42 rate (g/ha) | regrowth height (mm) Glyphosate rate (g a.e./ha) | | | |
|---|---|---|---|---|
| | 0 | 112 | 224 | 448 |
| 0 | 94 | 72 | 60 | 41 |
| 20 | | | 49 | |
| 200 | 67 | | 64 | |

The solvent used for compound 42 in this assay was isopropyl alcohol. Compound 42 at 20 g/ha in mixture with glyphosate enhanced the degree of regrowth reduction over that obtained with the same rate of glyphosate alone. At 200 g/ha, compound 42 failed to enhance the herbicidal effectiveness of glyphosate in this assay.

TABLE 1.48

| Compound 42 rate (g/ha) | regrowth height (mm) Glyphosate rate (g a.e./ha) | | | |
|---|---|---|---|---|
| | 0 | 112 | 224 | 448 |
| 0 | 54 | 59 | 39 | 36 |
| 20 | | | 29 | |
| 200 | 51 | | 27 | |

Compound 42 at both 20 g/ha and 200 g/ha in mixture with glyphosate enhanced the degree of regrowth reduction over that obtained with the same rate, or even two times that rate, glyphosate alone.

TABLE 1.49

| Compound 42 rate (g/ha) | regrowth height (mm) Glyphosate rate (g a.e./ha) | | | |
|---|---|---|---|---|
| | 0 | 56 | 112 | 224 |
| 0 | 58 | 47 | 40 | 21 |
| 20 | | | 31 | |
| 200 | 59 | | 40 | |

Compound 42 at 20 g/ha in mixture with glyphosate enhanced the degree of regrowth reduction over that obtained with the same rate of glyphosate alone. At 200 g/ha, compound 42 failed to enhance the herbicidal effectiveness of glyphosate in this assay.

TABLE 1.50

| Compound 42 rate (g/ha) | regrowth height (mm) Glyphosate rate (g a.e./ha) | | | |
|---|---|---|---|---|
| | 0 | 56 | 112 | 224 |
| 0 | 63 | 56 | 32 | 20 |
| 20 | | | 28 | |
| 200 | 55 | | 30 | |

Compound 42 at 20 g/ha in mixture with glyphosate slightly enhanced the degree of regrowth reduction over that obtained with the same rate of glyphosate alone. The degree of enhancement of herbicidal effectiveness of glyphosate observed with compound 42 at 200 g/ha was insignificant in this assay.

TABLE 1.51

| Compound 43 rate (g/ha) | regrowth height (mm) Glyphosate rate (g a.e./ha) | | | |
|---|---|---|---|---|
| | 0 | 56 | 112 | 224 |
| 0 | 63 | 61 | 54 | 27 |
| 2 | | | 45 | |
| 20 | | | 36 | |
| 50 | | | 36 | |

Compound 43 at 2 g/ha, 20 g/ha and 50 g/ha in mixture with glyphosate enhanced the degree of regrowth reduction over that obtained with the same rate of glyphosate alone.

TABLE 1.52

| Compound 43 rate (g/ha) | regrowth height (mm) Glyphosate rate (g a.e./ha) | | | |
|---|---|---|---|---|
| | 0 | 56 | 112 | 224 |
| 0 | 52 | 55 | 53 | 34 |
| 2 | | | 54 | |
| 20 | | | 47 | |
| 50 | | | 37 | |

Compound 43 at 20 g/ha and 50 g/ha in mixture with glyphosate enhanced the degree of regrowth reduction over that obtained with the same rate of glyphosate alone, with the strongest enhancement being noted at the 50 g/ha rate of compound 43. At 2 g/ha, compound 43 failed to enhance the herbicidal effectiveness of glyphosate in this assay.

TABLE 1.53

| Compound 45 rate (g/ha) | regrowth height (mm) Glyphosate rate (g a.e./ha) | | | |
|---|---|---|---|---|
| | 0 | 112 | 224 | 448 |
| 0 | 54 | 59 | 39 | 36 |
| 20 | | | 23 | |
| 200 | 55 | | 46 | |

Compound 45 at 20 g/ha in mixture with glyphosate enhanced the degree of regrowth reduction over that obtained with the same rate, or even two times that rate, of glyphosate alone. At 200 g/ha, compound 45 antagonized the herbicidal effectiveness of glyphosate.

TABLE 1.54

| Compound 45 rate (g/ha) | regrowth height (mm) Glyphosate rate (g a.e./ha) | | | |
|---|---|---|---|---|
| | 0 | 56 | 112 | 224 |
| 0 | 58 | 47 | 40 | 21 |
| 20 | | | 28 | |
| 200 | 57 | | 40 | |

Compound 45 at 20 g/ha in mixture with glyphosate enhanced the degree of regrowth reduction over that obtained with the same rate of glyphosate alone. At 200 g/ha, compound 45 failed to enhance the herbicidal effectiveness of glyphosate in this assay.

TABLE 1.55

| Compound 46 rate (g/ha) | regrowth height (mm) Glyphosate rate (g a.e./ha) | | | |
|---|---|---|---|---|
| | 0 | 56 | 112 | 224 |
| 0 | 53 | 48 | 32 | 19 |
| 20 | | | 25 | |
| 200 | 35 | | 21 | |

Compound 46 at both 20 g/ha and 200 g/ha in mixture with glyphosate enhanced the degree of regrowth reduction over that obtained with the same rate of glyphosate alone.

TABLE 1.56

| Compound 46 rate (g/ha) | regrowth height (mm) Glyphosate rate (g a.e./ha) | | | |
|---|---|---|---|---|
| | 0 | 56 | 112 | 224 |
| 0 | 63 | 61 | 54 | 27 |
| 2 | | | 43 | |
| 20 | | | 40 | |
| 50 | | | 35 | |

Compound 46 at 2 g/ha, 20 g/ha and 50 g/ha in mixture with glyphosate enhanced the degree of regrowth reduction over that obtained with the same rate of glyphosate alone, with the strongest enhancement being noted at the 50 g/ha rate of compound 46.

TABLE 1.57

| Compound 47 rate (g/ha) | regrowth height (mm) Glyphosate rate (g a.e./ha) | | | |
|---|---|---|---|---|
| | 0 | 56 | 112 | 224 |
| 0 | 55 | 56 | 43 | 32 |
| 2 | | | 42 | |
| 20 | | | 46 | |
| 50 | | | 39 | |

Compound 47 at 50 g/ha in mixture with glyphosate slightly enhanced the degree of regrowth reduction over that obtained with the same rate of glyphosate alone. At 2 g/ha and 20 g/ha, compound 47 failed to enhance the herbicidal effectiveness of glyphosate in this assay.

TABLE 1.58

| Compound 56 rate (g/ha) | regrowth height (mm) Glyphosate rate (g a.e./ha) | | | |
|---|---|---|---|---|
| | 0 | 56 | 112 | 224 |
| 0 | 52 | 55 | 53 | 34 |
| 2 | | | 38 | |
| 20 | | | 41 | |
| 50 | | | 51 | |

Compound 56 at 2 g/ha and 20 g/ha in mixture with glyphosate enhanced the degree of regrowth reduction over that obtained with the same rate of glyphosate alone, with the strongest enhancement being noted at the 2 g/ha rate of compound 56. At 50 g/ha, compound 56 did not enhance to a significant degree the herbicidal effectiveness of glyphosate in this assay.

TABLE 1.59

| Compound 57 | regrowth height (mm) | | | |
|---|---|---|---|---|
| | Glyphosate rate (g a.e./ha) | | | |
| rate (g/ha) | 0 | 56 | 112 | 224 |
| 0 | 55 | 52 | 52 | 25 |
| 2 | | | 52 | |
| 20 | | | 53 | |
| 50 | | | 53 | |

Compound 57 at 2, 20 or 50 g/ha in mixture with glyphosate did not in this assay enhance the degree of regrowth reduction over that obtained with the same rate of glyphosate alone.

TABLE 1.60

| Compound 58 | regrowth height (mm) | | | |
|---|---|---|---|---|
| | Glyphosate rate (g a.e./ha) | | | |
| rate (g/ha) | 0 | 56 | 112 | 224 |
| 0 | 61 | 61 | 52 | 28 |
| 2 | | | 43 | |
| 20 | | | 45 | |
| 50 | | | 47 | |

Compound 58 at 2 g/ha, 20 g/ha and 50 g/ha in mixture with glyphosate slightly enhanced the degree of regrowth reduction over that obtained with the same rate of glyphosate alone.

TABLE 1.61

| Compound 59 | regrowth height (mm) | | | |
|---|---|---|---|---|
| | Glyphosate rate (g a.e./ha) | | | |
| rate (g/ha) | 0 | 56 | 112 | 224 |
| 0 | 41 | 45 | 42 | 28 |
| 2 | | | 38 | |
| 20 | | | 37 | |
| 50 | | | 34 | |

Compound 59 at 2 g/ha, 20 g/ha and 50 g/ha in mixture with glyphosate slightly enhanced the degree of regrowth reduction over that obtained with the same rate of glyphosate alone, with the strongest enhancement being noted at the 50 g/ha rate of compound 59.

TABLE 1.62

| Compound 64 | regrowth height (mm) | | | |
|---|---|---|---|---|
| | Glyphosate rate (g a.e./ha) | | | |
| rate (g/ha) | 0 | 56 | 112 | 224 |
| 0 | 54 | 56 | 50 | 30 |
| 2 | | | 50 | |
| 20 | | | 50 | |
| 50 | | | 50 | |

Compound 64 at 2 g/ha, 20 g/ha and 50 g/ha failed to enhance the herbicidal effectiveness of glyphosate in this assay.

TABLE 1.63

| Compound 81 | regrowth height (mm) | | | |
|---|---|---|---|---|
| | Glyphosate rate (g a.e./ha) | | | |
| rate (g/ha) | 0 | 56 | 112 | 224 |
| 0 | 55 | 56 | 43 | 32 |
| 2 | | | 35 | |
| 20 | | | 48 | |
| 50 | | | 35 | |

Compound 81 at 2 g/ha and 50 g/ha in mixture with glyphosate enhanced the degree of regrowth reduction over that obtained with the same rate of glyphosate alone. At 20 g/ha, compound 81 failed to enhance the herbicidal effectiveness of glyphosate in this assay.

TABLE 1.64

| Compound 98 | regrowth height (mm) | | | |
|---|---|---|---|---|
| | Glyphosate rate (g a.e./ha) | | | |
| rate (g/ha) | 0 | 56 | 112 | 224 |
| 0 | 63 | 64 | 45 | 20 |
| 20 | | | 42 | |
| 200 | 66 | | 38 | |

Compound 98 at both 20 g/ha and 200 g/ha in mixture with glyphosate slightly enhanced the degree of regrowth reduction over that obtained with the same rate of glyphosate alone.

TABLE 1.65

| Compound 103 | regrowth height (mm) | | | |
|---|---|---|---|---|
| | Glyphosate rate (g a.e./ha) | | | |
| rate (g/ha) | 0 | 56 | 112 | 224 |
| 0 | 55 | 52 | 52 | 25 |
| 2 | | | 50 | |
| 20 | | | 56 | |
| 50 | | | 56 | |

Compound 103 at 2 g/ha, 20 g/ha and 50 g/ha failed to enhance the herbicidal effectiveness of glyphosate in this assay.

TABLE 1.66

| Compound 103 | regrowth height (mm) | | | |
|---|---|---|---|---|
| | Glyphosate rate (g a.e./ha) | | | |
| rate (g/ha) | 0 | 56 | 112 | 224 |
| 0 | 57 | 56 | 43 | 24 |
| 2 | | | 42 | |
| 20 | | | 38 | |
| 50 | | | 38 | |

Compound 103 at 20 g/ha and 50 g/ha in mixture with glyphosate slightly enhanced the degree of regrowth reduction over that obtained with the same rate of glyphosate alone At 2 g/ha, compound 103 failed to enhance the herbicidal effectiveness of glyphosate in this assay.

TABLE 1.67

| Compound 104 rate (g/ha) | regrowth height (mm) Glyphosate rate (g a.e./ha) | | | |
|---|---|---|---|---|
| | 0 | 56 | 112 | 224 |
| 0 | 60 | 60 | 44 | 31 |
| 2 | | | 51 | |
| 20 | | | 43 | |
| 50 | | | 38 | |

Compound 104 at 50 g/ha in mixture with glyphosate slightly enhanced the degree of regrowth reduction over that obtained with the same rate of glyphosate alone. At 2 g/ha and 20 g/ha, compound 104 failed to enhance the herbicidal effectiveness of glyphosate in this assay.

TABLE 1.68

| Compound 105 rate (g/ha) | regrowth height (mm) Glyphosate rate (g a.e./ha) | | | |
|---|---|---|---|---|
| | 0 | 56 | 112 | 224 |
| 0 | 58 | 51 | 56 | 45 |
| 2 | | | 52 | |
| 20 | | | 50 | |
| 50 | | | 54 | |

Compound 105 at 2 g/ha, 20 g/ha and 50 g/ha in mixture with glyphosate slightly enhanced the degree of regrowth reduction over that obtained with the same rate of glyphosate alone.

TABLE 1.69

| Compound 106 rate (g/ha) | regrowth height (mm) Glyphosate rate (g a.e./ha) | | | |
|---|---|---|---|---|
| | 0 | 56 | 112 | 224 |
| 0 | 65 | 60 | 45 | 28 |
| 20 | | | 27 | |
| 200 | 58 | | 36 | |

Compound 106 at 20 g/ha and 200 g/ha in mixture with glyphosate enhanced the degree of regrowth reduction over that obtained with the same rate of glyphosate alone, with the strongest enhancement being shown at the 20 g/ha rate of compound 106.

TABLE 1.70

| Compound 107 rate (g/ha) | regrowth height (mm) Glyphosate rate (g a.e./ha) | | | |
|---|---|---|---|---|
| | 0 | 56 | 112 | 224 |
| 0 | 65 | 60 | 45 | 28 |
| 20 | | | 23 | |
| 200 | 53 | | 26 | |

Compound 107 at 20 g/ha and 200 g/ha in mixture with glyphosate enhanced the degree of regrowth reduction over that obtained with the same rate, or even two times that rate, of glyphosate alone.

TABLE 1.71

| Compound 108 rate (g/ha) | regrowth height (mm) Glyphosate rate (g a.e./ha) | | | |
|---|---|---|---|---|
| | 0 | 56 | 112 | 224 |
| 0 | 51 | 50 | 26 | 20 |
| 20 | | | 22 | |
| 200 | 36 | | 30 | |

Compound 108 at 20 g/ha in mixture with glyphosate slightly enhanced the degree of regrowth reduction over that obtained with the same rate of glyphosate alone. At 200 g/ha, compound 108 failed to enhance the herbicidal effectiveness of glyphosate in this assay.

TABLE 1.72

| Compound 109 rate (g/ha) | regrowth height (mm) Glyphosate rate (g a.e./ha) | | | |
|---|---|---|---|---|
| | 0 | 56 | 112 | 224 |
| 0 | 65 | 60 | 36 | 24 |
| 20 | | | 25 | |
| 200 | 30 | | 23 | |

Compound 109 at 20 g/ha and 200 g/ha in mixture with glyphosate enhanced the degree of regrowth reduction over that obtained with the same rate, to a level comparable with that obtained with two times that rate, of glyphosate alone.

TABLE 1.73

| Compound 109 rate (g/ha) | regrowth height (mm) Glyphosate rate (g a.e./ha) | | | |
|---|---|---|---|---|
| | 0 | 56 | 112 | 224 |
| 0 | 72 | 73 | 48 | 23 |
| 20 | | | 59 | |
| 200 | 46 | | 39 | |

Compound 109 at 200 g/ha in mixture with glyphosate enhanced the degree of regrowth reduction over that obtained with the same rate of glyphosate alone. At 20 g/ha, compound 109 failed to enhance the herbicidal effectiveness of glyphosate in this assay.

TABLE 1.74

| Compound 109 rate (g/ha) | regrowth height (mm) Glyphosate rate (g a.e./ha) | | | |
|---|---|---|---|---|
| | 0 | 56 | 112 | 224 |
| 0 | 63 | 64 | 45 | 20 |
| 20 | | | 43 | |
| 200 | 58 | | 33 | |

Compound 109 at 200 g/ha in mixture with glyphosate enhanced the degree of regrowth reduction over that obtained with the same rate of glyphosate alone. At 20 g/ha, compound 109 failed to enhance the herbicidal effectiveness of glyphosate in this assay.

TABLE 1.75

| Compound 110 rate (g/ha) | regrowth height (mm) Glyphosate rate (g a.e./ha) | | | |
|---|---|---|---|---|
| | 0 | 56 | 112 | 224 |
| 0 | 54 | 56 | 61 | 48 |
| 2 | | | 54 | |
| 20 | | | 50 | |
| 50 | | | 60 | |

Compound 110 at 2 g/ha and 20 g/ha in mixture with glyphosate enhanced the degree of regrowth reduction over that obtained with the same rate of glyphosate alone. At 50 g/ha, compound 1 10 failed to enhance the herbicidal effectiveness of glyphosate in this assay.

TABLE 1.76

| Compound 111 rate (g/ha) | regrowth height (mm) Glyphosate rate (g a.e./ha) | | | |
|---|---|---|---|---|
| | 0 | 56 | 112 | 224 |
| 0 | 54 | 56 | 61 | 48 |
| 2 | | | 56 | |
| 20 | | | 58 | |
| 50 | | | 48 | |

Compound 111 at 2 g/ha, 20 g/ha and 50 g/ha in mixture with glyphosate enhanced the degree of regrowth reduction over that obtained with the same rate of glyphosate alone, with the strongest enhancement being noted at the 50 g/ha rate of compound 111.

TABLE 1.77

| Compound 112 rate (g/ha) | regrowth height (mm) Glyphosate rate (g a.e./ha) | | | |
|---|---|---|---|---|
| | 0 | 56 | 112 | 224 |
| 0 | 54 | 56 | 61 | 48 |
| 2 | | | 59 | |
| 20 | | | 51 | |
| 50 | | | 58 | |

Compound 112 at 20 g/ha in mixture with glyphosate enhanced the degree of regrowth reduction over that obtained with the same rate of glyphosate alone. At 2 g/ha and 50 g/ha, compound 112 did not significantly enhance the herbicidal effectiveness of glyphosate in this assay.

TABLE 1.78

| Compound 113 rate (g/ha) | regrowth height (mm) Glyphosate rate (g a.e./ha) | | | |
|---|---|---|---|---|
| | 0 | 56 | 112 | 224 |
| 0 | 54 | 56 | 61 | 48 |
| 2 | | | 42 | |
| 20 | | | 55 | |
| 50 | | | 50 | |

Compound 113 at 2 g/ha, 20 g/ha and 50 g/ha in mixture with glyphosate enhanced the degree of regrowth reduction over that obtained with the same rate of glyphosate alone, with the strongest enhancement being noted at the 2 g/ha rate of compound 113.

TABLE 1.79

| Compound 114 rate (g/ha) | regrowth height (mm) Glyphosate rate (g a.e./ha) | | | |
|---|---|---|---|---|
| | 0 | 56 | 112 | 224 |
| 0 | 54 | 56 | 61 | 48 |
| 2 | | | 41 | |
| 20 | | | 45 | |
| 50 | | | 40 | |

Compound 114 at 2 g/ha, 20 g/ha and 50 g/ha in mixture with glyphosate enhanced the degree of regrowth reduction over that obtained with the same rate, or even two times that rate, of glyphosate alone.

TABLE 1.80

| Compound 114 rate (g/ha) | regrowth height (mm) Glyphosate rate (g a.e./ha) | | | |
|---|---|---|---|---|
| | 0 | 56 | 112 | 224 |
| 0 | 63 | 64 | 45 | 20 |
| 20 | | | 40 | |
| 200 | 66 | | 33 | |

Compound 114 at 20 g/ha and 200 g/ha in mixture with glyphosate enhanced the degree of regrowth reduction over that obtained with the same rate of glyphosate alone.

Example 2

Seeds of velvetleaf (Abutilon theophrasti, ABUTH) and Japanese millet, a form of barnyardgrass (Echinochloa crusgalli, ECHCF), were planted in 85 mm square pots in a soil mix which was previously steam sterilized and prefertilized with a 14-14-14 NPK slow release fertilizer at a rate of 3.6 kg/m$^3$. The pots were placed in a greenhouse with sub-irrigation. About one week after emergence, seedlings were thinned as needed, including removal of any unhealthy or abnormal plants, to create a uniform series of test pots.

The plants were maintained for the duration of the test in a greenhouse where they received a minimum of 14 hours of light per day. If natural light was insufficient to achieve the daily requirement, artificial light with an intensity of approximately 475 microeinsteins was used to make up the difference. Exposure temperatures were not precisely controlled but averaged about 27° C. during the day and 18° C. during the night. Plants were sub-irrigated throughout the test to ensure adequate soil moisture levels. ECHCF plants were clipped at least once but were allowed to regrow for at least 3 days before chemical treatment.

Pots were assigned to different treatments in a fully randomized experimental design with 3 replications. A set of pots was left untreated as a reference against which effects of the treatments could later be evaluated.

Chemical treatments were applied as post-emergence applications to the plants 12 days after planting ABUTH and 14 days after planting ECHCF. Applications were made by spraying with a track sprayer fitted with a 9501E nozzle calibrated to deliver a spray volume of 93 l/ha at a pressure of 166 kPa. After treatment, pots were returned to the greenhouse until ready for evaluation.

Spray compositions used for comparative purposes were made by dilution in water of the same glyphosate formulation as used in Example 1. Spray compositions illustrative of the present invention were made in exactly the same way, except that calculated amounts of compound 17 (α-methyl-trans-cinnamaldehyde), dissolved in a small amount of dimethyl sulfoxide, were added to the compositions.

Sixteen days after application, all plants in the test were examined by a single practiced technician to evaluate percent inhibition, which is a visual measurement of the herbicidal effectiveness of the treatment by comparison with untreated plants. A percent inhibition of 0% indicates no effect, and a percent inhibition of 100% indicates that all of the plants are completely dead. A percent inhibition of 85% or more is in most cases considered commercially acceptable for normal herbicidal use, although lower percent inhibition values give useful indication of relative herbicidal effectiveness for the purposes of tests such as illustrated in this Example.

Treatments and corresponding percent inhibitions, averaged for all replicates of each treatment, are given in Table 2.

TABLE 2

| Glyphosate rate | Compound 17 | % inhibition | |
|---|---|---|---|
| (g a.e./ha) | rate (g/ha) | ABUTH | ECHCF |
| 0 | 200 | 0 | 0 |
| 112 | 0 | 68 | 53 |
| 224 | 0 | 85 | 95 |
| 448 | 0 | 98 | 100 |
| 224 | 2 | 95 | 97 |
| 224 | 20 | 85 | 98 |
| 224 | 100 | 90 | 98 |

Example 3

As test was conducted following exactly the procedures described in Example 2, except that applications were made 13 days after planting ABUTH and 16 days after planting ECHCF. Evaluation of percent inhibition was done 15 days after treatment. Treatments and corresponding percent inhibitions, averaged for all replicates of each treatment, are given in Table 3.

TABLE 3

| Glyphosate rate | Compound 17 | % inhibition | |
|---|---|---|---|
| (g a.e./ha) | rate (g/ha) | ABUTH | ECHCF |
| 0 | 200 | 0 | 0 |
| 56 | 0 | 10 | 28 |
| 112 | 0 | 46 | 75 |
| 224 | 0 | 85 | 94 |
| 112 | 2 | 30 | 77 |
| 112 | 20 | 55 | 86 |
| 112 | 100 | 65 | 75 |

Example 4

A test was conducted following exactly the procedures described in Example 2, except that applications were made 13 days after planting ABUTH and 16 days after planting ECHCF. Evaluation of percent inhibition was done 15 days after treatment. Treatments and corresponding percent inhibitions, averaged for all replicates of each treatment, are given in Table 4.

TABLE 4

| Glyphosate rate | Compound 17 | % inhibition | |
|---|---|---|---|
| (g a.e./ha) | rate (g/ha) | ABUTH | ECHCF |
| 0 | 200 | 0 | 0 |
| 56 | 0 | 2 | 36 |
| 112 | 0 | 33 | 73 |
| 224 | 0 | 73 | 99 |
| 112 | 2 | 38 | 75 |
| 112 | 20 | 38 | 85 |
| 112 | 100 | 50 | 95 |

Example 5

A test was conducted following exactly the procedures described in Example 2, except that applications were made 13 days after planting ABUTH and 17 days after planting ECHCF. Evaluation of percent inhibition was done 21 days after treatment. Treatments and corresponding percent inhibitions, averaged for all replicates of each treatment, are given in Table 5.

TABLE 5

| Glyphosate rate | Compound 17 | % inhibition | |
|---|---|---|---|
| (g a.e./ha) | rate (g/ha) | ABUTH | ECHCF |
| 0 | 200 | 0 | 0 |
| 56 | 0 | 16 | 23 |
| 112 | 0 | 38 | 40 |
| 224 | 0 | 54 | 81 |
| 112 | 2 | 38 | 43 |
| 112 | 20 | 28 | 43 |
| 112 | 100 | 49 | 41 |

Example 6

A test was conducted following exactly the procedures described in Example 2, except that applications were made 14 days after planting ABUTH and 17 days after planting ECHCF. Evaluation of percent inhibition was done 14 days after treatment. Treatment and corresponding percent inhibitions, averaged for all replicates of each treatment, are given in Table 6.

TABLE 6

| Glyphosate rate | Compound 17 | % inhibition | |
|---|---|---|---|
| (g a.e./ha) | rate (g/ha) | ABUTH | ECHCF |
| 0 | 200 | 0 | 0 |
| 56 | 0 | 0 | 0 |
| 112 | 0 | 45 | 29 |
| 224 | 0 | 73 | 79 |
| 112 | 2 | 53 | 31 |
| 112 | 20 | 68 | 35 |
| 112 | 100 | 48 | 33 |

The tests of Examples 2–6 showed some variation in the ability of compound 17 to enhance the herbicidal effectiveness of glyphosate on ABUTH and ECHCF.

Example 7

A test was conducted following the procedures described in Example 2, except that the phenyl-substituted olefin compound used was compound 116 (safrole). Applications were made 11 days after planting ABUTH and 13 days after planting ECHCF. Evaluation of percent inhibition was done 19 days after treatment. Treatments and corresponding percent inhibitions, averaged for all replicates of each treatment, are given in Table 7.

TABLE 7

| Glyphosate rate | Compound 116 | % inhibition | |
|---|---|---|---|
| (g a.e./ha) | rate (g/ha) | ABUTH | ECHCF |
| 0 | 200 | 0 | 0 |
| 56 | 0 | 28 | 46 |
| 112 | 0 | 53 | 68 |
| 224 | 0 | 74 | 97 |
| 112 | 0.2 | 33 | 64 |
| 112 | 2 | 33 | 58 |
| 112 | 10 | 38 | 69 |
| 112 | 20 | 44 | 70 |
| 112 | 50 | 39 | 56 |
| 112 | 100 | 41 | 59 |
| 112 | 200 | 45 | 60 |

Example 8

A test was conducted following the procedures described in Example 2, except that the phenyl-substituted olefin compound used was compound 116 (safrole). Applications were made 11 days after planting ABUTH and ECHCF. Evaluation of percent inhibition was done 20 days after treatment. Treatments and corresponding percent inhibitions, averaged for all replicates of each treatment, are given in Table 8.

TABLE 8

| Glyphosate rate | Compound 116 | % inhibition | |
|---|---|---|---|
| (g a.e./ha) | rate (g/ha) | ABUTH | ECHCF |
| 0 | 200 | 0 | 0 |
| 112 | 0 | 20 | 81 |
| 224 | 0 | 58 | 92 |
| 112 | 2 | 30 | 86 |
| 112 | 20 | 41 | 81 |
| 112 | 200 | 18 | 61 |

The tests of Examples 7 and 8 showed some variation in the ability of compound 116 to enhance the herbicidal effectiveness of glyphosate on ABUTH and ECHCF.

Example 9

A test was conducted following the procedures described in Example 2, except that in addition to ABUTH and ECHCF two other species were included: momingglory (Isomea sp. IPOSS) and annual ryegrass (Lolium multiflorum, LOLMG). ECHCF and LOLMG plants were clipped at least once, but were allowed to regrow for at least 3 days before chemical treatment. Each treatment was replicated 4 times.

Applications were made 12 days after planting ABUTH and IPOSS and 14 days after planting ECHCF. Evaluation of percent inhibition was done 20 days after treatment. Treatments and corresponding percent inhibitions, averaged for all replicates of each treatment, are given in Table 9.

TABLE 9

| Glyphosate rate | Compound 17 | % inhibition | | | |
|---|---|---|---|---|---|
| (g a.e./ha) | rate (g/ha) | ABUTH | IPOSS | LOLMG | ECHCF |
| 200 | 0 | 57 | 38 | 82 | 83 |
| 300 | 0 | 71 | 52 | 90 | 100 |
| 400 | 0 | 98 | 73 | 96 | 99 |
| 500 | 0 | 100 | 87 | 100 | 100 |
| 600 | 0 | 100 | 92 | 100 | 100 |
| 800 | 0 | 100 | 92 | 100 | 100 |
| 200 | 2 | 66 | 60 | 100 | 86 |
| 200 | 20 | 80 | 66 | 100 | 81 |
| 200 | 50 | 86 | 73 | 100 | 93 |
| 300 | 2 | 90 | 80 | 100 | 100 |
| 300 | 20 | 89 | 81 | 100 | 100 |
| 300 | 50 | 96 | 84 | 95 | 94 |
| 400 | 2 | 95 | 88 | 100 | 100 |
| 400 | 20 | 99 | 95 | 100 | 100 |
| 400 | 50 | 100 | 94 | 100 | 100 |

Example 10

A test was conducted following the procedures of Example 9. Applications were made 11 days after planting ABUTH and [POSS and 14 days after planting ECHCF. Evaluation of percent inhibition was done 20 days after treatment. Treatments and corresponding percent inhibitions, averaged for all replicates of each treatment, are given in Table 10.

TABLE 10

| Glyphosate rate | Compound 17 | % inhibition | | | |
|---|---|---|---|---|---|
| (g a.e./ha) | rate (g/ha) | ABUTH | IPOSS | LOLMG | ECHCF |
| 200 | 0 | 66 | 63 | 83 | 78 |
| 300 | 0 | 73 | 77 | 100 | 100 |
| 400 | 0 | 98 | 81 | 100 | 100 |
| 500 | 0 | 100 | 85 | 100 | 100 |
| 600 | 0 | 100 | 86 | 100 | 100 |
| 800 | 0 | 100 | 99 | 100 | 100 |
| 200 | 2 | 85 | 77 | 100 | 100 |
| 200 | 20 | 91 | 78 | 88 | 100 |
| 300 | 2 | 96 | 81 | 100 | 100 |
| 300 | 20 | 96 | 87 | 100 | 100 |
| 400 | 2 | 100 | 85 | 100 | 100 |
| 400 | 20 | 100 | 89 | 100 | 100 |

Example 11

A test was conducted following the procedures of Example 9. Applications were made 14 days after planting ABUTH and IPOSS and 16 days after planting ECHCF. Evaluation of percent inhibition was done 20 days after treatment. Treatments and corresponding percent inhibitions, averaged for all replicates of each treatment, are given in Table 11.

TABLE 11

| Glyphosate rate | Compound 17 | % inhibition | | | |
|---|---|---|---|---|---|
| (g a.e./ha) | rate (g/ha) | ABUTH | IPOSS | LOLMG | ECHCF |
| 200 | 0 | 30 | 12 | 41 | 18 |
| 300 | 0 | 58 | 50 | 63 | 65 |

TABLE 11-continued

| Glyphosate rate | Compound 17 | % inhibition | | | |
|---|---|---|---|---|---|
| (g a.e./ha) | rate (g/ha) | ABUTH | IPOSS | LOLMG | ECHCF |
| 400 | 0 | 76 | 65 | 81 | 63 |
| 500 | 0 | 83 | 77 | 85 | 100 |
| 600 | 0 | 85 | 83 | 92 | 98 |
| 800 | 0 | 90 | 87 | 100 | 100 |
| 200 | 2 | 35 | 37 | 61 | 29 |
| 200 | 20 | 44 | 39 | 59 | 29 |
| 300 | 2 | 65 | 54 | 69 | 62 |
| 300 | 20 | 62 | 55 | 67 | 68 |
| 400 | 2 | 79 | 71 | 86 | 87 |
| 400 | 20 | 80 | 78 | 88 | 93 |

Example 12

A tests conducted following the procedures of Example 9. Applications were made 13 days after planting ABUTH and IPOSS and 16 days after planting ECHCF. Evaluation of percent inhibition was done 21 days after treatment. Treatments and corresponding percent inhibitions, averaged for all replicates of each treatment, are given in Table 12.

TABLE 12

| Glyphosate rate | Compound 17 | % inhibition | | | |
|---|---|---|---|---|---|
| (g a.e./ha) | rate (g/ha) | ABUTH | IPOSS | LOLMG | ECHCF |
| 200 | 0 | 54 | 13 | 58 | 69 |
| 300 | 0 | 75 | 42 | 70 | 83 |
| 400 | 0 | 80 | 65 | 81 | 91 |
| 600 | 0 | 100 | 81 | 91 | 96 |
| 800 | 0 | 99 | 82 | 100 | 100 |
| 1000 | 0 | 100 | 97 | 100 | 100 |
| 200 | 2 | 45 | 39 | 56 | 68 |
| 200 | 20 | 59 | 43 | 72 | 75 |
| 300 | 2 | 78 | 49 | 86 | 98 |
| 300 | 20 | 61 | 43 | 68 | 87 |
| 400 | 2 | 80 | 47 | 87 | 100 |
| 400 | 20 | 83 | 74 | 71 | 87 |

Example 13

A test was conducted following the procedures of Example 9 except that yellow foxtail (Setaria glauca, SETLU) was used in place of LOLMG, and the phenyl-substituted olefin compound used was compound 116 (safrole). Applications were made 14 days after planting SETLU and ECHCF and 11 days after planting ABUTH and IPOSS. Evaluation of percent inhibition was done 15 days after treatment. Treatments and corresponding percent inhibitions, averaged for all replicates of each treatment, are given in Table 13.

TABLE 13

| Glyphosate rate | Compound 116 | % inhibition | | | |
|---|---|---|---|---|---|
| (g a.e./ha) | rate (g/ha) | ABUTH | IPOSS | SETLU | ECHCF |
| 56 | 0 | 33 | 12 | 15 | 8 |
| 112 | 0 | 40 | 20 | 33 | 13 |
| 224 | 0 | 55 | 23 | 73 | 63 |
| 336 | 0 | 79 | 70 | 92 | 79 |
| 56 | 2 | 10 | 3 | 13 | 8 |
| 56 | 20 | 23 | 18 | 42 | 10 |

TABLE 13-continued

| Glyphosate rate | Compound 116 | % inhibition | | | |
|---|---|---|---|---|---|
| (g a.e./ha) | rate (g/ha) | ABUTH | IPOSS | SETLU | ECHCF |
| 56 | 200 | 40 | 42 | 50 | 22 |
| 112 | 2 | 42 | 23 | 40 | 30 |
| 112 | 20 | 40 | 40 | 18 | 22 |
| 112 | 200 | 58 | 35 | 66 | 50 |

Example 14

A test was conducted following the procedures described in Example 2, with the following exceptions. Each treatment was replicated 4 times. Applications were made 12 days after planting ABUTH and 14 days after planting ECHCF. Evaluation of percent inhibition was done 18 days after treatment.

Spray compositions used for comparative purposes were made by dilution in water of a 62% by weight isopropylammonium glyphosate aqueous solution together with a surfactant, so as to give a weight/weight ratio of glyphosate a.e. to surfactant of either 2:1 or 4:1. Different surfactants were used, as detailed below.

Surfactant A: polyoxyethylene (15) tallowamine (MON 0818 of Monsanto Company.)

Surfactant B: a polyoxyethylene alkyletheramine surfactant of formula

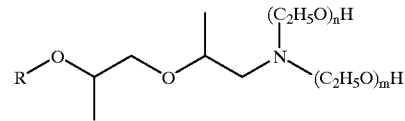

as disclosed in PCT Patent Application No. WO 96/32839, published Oct. 24, 1996, wherein R is $C_{12-14}$ alkyl and m+n has an average value of 5.

Surfactant C: $C_{9-11}$ alkyl polyglucoside, 1.5 moles glucose (Agrimul™ PG 2069 of Henkel).

Surfactant D: polyoxyethylene (8) $C_9$ i] alcohol ethoxylate (Neodol™ 91-8 of Shell).

Spray compositions were also made with no surfactant, and with the surfactant component replaced by glycerol. Spray compositions illustrative of the present invention were made exactly as above, except that calculated amounts of compound 17, dissolved in a small amount of dimethyl sulfoxide, were added to the compositions.

Treatments and corresponding percent inhibitions, averaged for all replicates of each treatment, are given in Table 14.

TABLE 14

| Glyphosate rate | | G/S | Compound 17 | % inhibition | |
|---|---|---|---|---|---|
| (g a.e./ha) | Surfactant | ratio* | rate (g/ha) | ABUTH | ECHCF |
| 112 | none | | 0 | 6 | 5 |
| 224 | none | | 0 | 11 | 6 |
| 336 | none | | 0 | 71 | 51 |
| 448 | none | | 0 | 77 | 68 |
| 112 | none | | 2 | 6 | 0 |
| 224 | none | | 2 | 44 | 24 |
| 112 | none | | 50 | 0 | 0 |
| 224 | none | | 50 | 54 | 54 |

TABLE 14-continued

| Glyphosate rate (g a.e./ha) | Surfactant | G/S ratio* | Compound 17 rate (g/ha) | % inhibition ABUTH | % inhibition ECHCF |
|---|---|---|---|---|---|
| 112 | A | 2:1 | 0 | 3 | 10 |
| 224 | A | 2:1 | 0 | 58 | 70 |
| 336 | A | 2:1 | 0 | 93 | 99 |
| 448 | A | 2:1 | 0 | 93 | 100 |
| 112 | A | 2:1 | 2 | 6 | 23 |
| 224 | A | 2:1 | 2 | 69 | 72 |
| 112 | A | 2:1 | 50 | 10 | 31 |
| 224 | A | 2:1 | 50 | 80 | 72 |
| 112 | A | 4:1 | 0 | 5 | 23 |
| 224 | A | 4:1 | 0 | 68 | 80 |
| 336 | A | 4:1 | 0 | 83 | 98 |
| 448 | A | 4:1 | 0 | 97 | 99 |
| 112 | A | 4:1 | 2 | 5 | 5 |
| 224 | A | 4:1 | 2 | 68 | 75 |
| 112 | A | 4:1 | 50 | 4 | 6 |
| 224 | A | 4:1 | 50 | 63 | 58 |
| 112 | B | 2:1 | 0 | 9 | 13 |
| 224 | B | 2:1 | 0 | 60 | 60 |
| 336 | B | 2:1 | 0 | 90 | 96 |
| 448 | B | 2:1 | 0 | 89 | 99 |
| 112 | B | 2:1 | 2 | 5 | 4 |
| 224 | B | 2:1 | 2 | 63 | 60 |
| 112 | B | 2:1 | 50 | 0 | 13 |
| 224 | B | 2:1 | 50 | 63 | 81 |
| 112 | B | 4:1 | 0 | 3 | 13 |
| 224 | B | 4:1 | 0 | 48 | 55 |
| 336 | B | 4:1 | 0 | 94 | 96 |
| 448 | B | 4:1 | 0 | 94 | 96 |
| 112 | B | 4:1 | 2 | 15 | 5 |
| 224 | B | 4:1 | 2 | 58 | 71 |
| 112 | B | 4:1 | 50 | 3 | 11 |
| 224 | B | 4:1 | 50 | 76 | 78 |
| 112 | C | 2:1 | 0 | 0 | 1 |
| 224 | C | 2:1 | 0 | 61 | 59 |
| 336 | C | 2:1 | 0 | 76 | 80 |
| 448 | C | 2:1 | 0 | 87 | 81 |
| 112 | C | 2:1 | 2 | 3 | 15 |
| 224 | C | 2:1 | 2 | 64 | 44 |
| 112 | C | 2:1 | 50 | 0 | 23 |
| 224 | C | 2:1 | 50 | 50 | 66 |
| 112 | C | 4:1 | 0 | 3 | 3 |
| 224 | C | 4:1 | 0 | 43 | 56 |
| 336 | C | 4:1 | 0 | 70 | 85 |
| 448 | C | 4:1 | 0 | 79 | 95 |
| 112 | C | 4:1 | 2 | 3 | 5 |
| 224 | C | 4:1 | 2 | 39 | 58 |
| 112 | C | 4:1 | 50 | 3 | 14 |
| 224 | C | 4:1 | 50 | 53 | 67 |
| 112 | D | 2:1 | 0 | 3 | 5 |
| 224 | D | 2:1 | 0 | 56 | 30 |
| 336 | D | 2:1 | 0 | 91 | 83 |
| 448 | D | 2:1 | 0 | 93 | 87 |
| 112 | D | 2:1 | 2 | 1 | 0 |
| 224 | D | 2:1 | 2 | 65 | 53 |
| 112 | D | 2:1 | 50 | 15 | 0 |
| 224 | D | 2:1 | 50 | 68 | 50 |
| 112 | D | 4:1 | 0 | 5 | 5 |
| 224 | D | 4:1 | 0 | 50 | 45 |
| 336 | D | 4:1 | 0 | 73 | 85 |
| 448 | D | 4:1 | 0 | 80 | 89 |
| 112 | D | 4:1 | 2 | 4 | 0 |
| 224 | D | 4:1 | 2 | 43 | 54 |
| 112 | D | 4:1 | 50 | 8 | 0 |
| 224 | D | 4:1 | 50 | 70 | 48 |
| 112 | glycerol | 2:1 | 0 | 0 | 0 |
| 224 | glycerol | 2:1 | 0 | 40 | 21 |
| 336 | glycerol | 2:1 | 0 | 93 | 51 |
| 448 | glycerol | 2:1 | 0 | 86 | 60 |
| 112 | glycerol | 2:1 | 2 | 3 | 0 |
| 224 | glycerol | 2:1 | 2 | 60 | 26 |
| 112 | glycerol | 2:1 | 50 | 9 | 3 |
| 224 | glycerol | 2:1 | 50 | 48 | 40 |
| 112 | glycerol | 4:1 | 0 | 3 | 0 |
| 224 | glycerol | 4:1 | 0 | 50 | 29 |
| 336 | glycerol | 4:1 | 0 | 77 | 50 |
| 448 | glycerol | 4:1 | 0 | 89 | 63 |
| 112 | glycerol | 4:1 | 2 | 0 | 0 |
| 224 | glycerol | 4:1 | 2 | 56 | 26 |
| 112 | glycerol | 4:1 | 50 | 0 | 0 |
| 224 | glycerol | 4:1 | 50 | 49 | 40 |

*weight/weight ratio of glyphosate a.e. to surfactant or glycerol

Example 15

Concentrate formulations (F1 to F5) of the isopropylammonium salt of glyphosate were made containing various surfactants and safrole (compound 116). In each case the formulation was made by simple mixing of (a) 62% by weight isopropylammonium glyphosate aqueous solution, (b) a surfactant as detailed below, (c) safrole in "neat" form, i.e. not pre-dissolved in solvent, and (d) water. It was found that safrole could be emulsified at the concentrations used in the presence of the surfactant used in each case.

All the following formulations have a glyphosate a.e. loading, or weight/volume concentration, of 360 g/l. Surfactant loading was 8.4% by weight in each case, expressed on a true surfactant basis, i.e. excluding water or other solvent in which the surfactant may be supplied commercially. Safrole loading was 13 g/l in each formulation. Surfactants used in Formulations F 1 to F5 were:

F1: Polyoxyethylene (5) cocoamine (Ethomeen™ C/15 of Akzo).

F2: Polyoxyethylene (5) tallowamine (Ethomeen™ T/5 of Akzo).

F3: Surfactant A as described in Example 14 (MON 0818).

F4: Surfactant B as described in Example 14 (polyoxyethylene alkyletheramine).

F5: Surfactant E, a polyoxyethylene alkyletheramine surfactant of formula

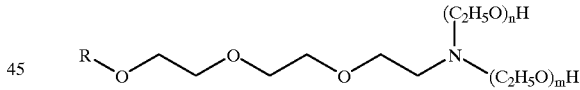

as disclosed in PCT Patent Application No. WO 96/32839, published Oct. 24, 1996, wherein R is $C_{12-14}$ alkyl and m+n has an average value of 5.

All of the above formulations showed acceptable physical stability when stored at room temperature for at least one week. Cloud points of all the above formulations were higher than 50° C.

Formulations F1 to F5 were diluted or dispersed in water and applied to velvetleaf (ABUTH) and Japanese millet (ECHCF) plants in a greenhouse test, following a procedure similar to that of Example 14. Applications were made 20 days after planting ABUTH and 18 days after planting ECHCF. Evaluation of percent inhibition was done 21 days after application. Additionally, Formulation F0, containing no surfactant but containing 360 g a.e./l glyphosate as the isopropylammonium salt and 13 g/l safrole, was included in the test. For comparative purposes, blank formulations B0 to B5, containing the same glyphosate and surfactant loadings as formulations F0 to F5 respectively but containing no safrole, were applied by the same procedures.

Treatments and corresponding percent inhibitions, averaged for all replicates of each treatment, are given in Table 15.

TABLE 15

| Formulation no. | Glyphosate rate (g a.e./ha) | percent inhibition ABUTH | ECHCF |
|---|---|---|---|
| B0 | 112 | 0 | 0 |
|  | 224 | 26 | 36 |
|  | 336 | 58 | 63 |
| F0 | 112 | 0 | 3 |
|  | 224 | 25 | 21 |
|  | 336 | 59 | 40 |
| B1 | 112 | 3 | 30 |
|  | 224 | 38 | 74 |
|  | 336 | 65 | 93 |
| F1 | 112 | 5 | 21 |
|  | 224 | 34 | 70 |
|  | 336 | 61 | 85 |
| B2 | 112 | 5 | 25 |
|  | 224 | 39 | 68 |
|  | 336 | 64 | 88 |
| F2 | 112 | 0 | 31 |
|  | 224 | 45 | 78 |
|  | 336 | 56 | 96 |
| B3 | 112 | 0 | 30 |
|  | 224 | 39 | 69 |
|  | 336 | 50 | 93 |
| F3 | 112 | 4 | 16 |
|  | 224 | 64 | 86 |
|  | 336 | 75 | 98 |
| B4 | 112 | 0 | 30 |
|  | 224 | 44 | 78 |
|  | 336 | 50 | 93 |
| F4 | 112 | 3 | 33 |
|  | 224 | 45 | 85 |
|  | 336 | 69 | 93 |
| B5 | 112 | 0 | 35 |
|  | 224 | 44 | 80 |
|  | 336 | 61 | 97 |
| F5 | 112 | 0 | 28 |
|  | 224 | 50 | 83 |
|  | 336 | 73 | 100 |

In this test safrole did not enhance the herbicidal effectiveness of glyphosate in the absence of surfactant. Glyphosate concentrate formulations of the invention containing safrole and surfactant showed superior herbicidal effectiveness by comparison with similar formulations containing no safrole, with the sole exception of the formulation (F1) in which the surfactant was Ethomeen™ C/15.

Example 16

Concentrate formulations of the isopropylammonium salt of glyphosate were made containing various surfactants and α-methyl-trans-cinnamaldehyde (compound 17). In each case the formulation was made by simple mixing of (a) 62% by weight isopropylammonium glyphosate aqueous solution, (b) one or more surfactants as detailed below, (c) α-methyl-trans-cinnamaldehyde in "neat" form, i.e. not pre-dissolved in solvent, and (d) water. It was found that α-methyl-trans-cinnamaldehyde, which is an oily liquid of low water solubility, could be emulsified at the concentrations used in the presence of the surfactant(s) used in each case.

All the following formulations have a glyphosate a.e. loading, or weight/volume concentration, of 480 g/l. Surfactant loadings shown below are expressed on a true surfactant basis, i.e. excluding water or other solvent in which the surfactant may be supplied commercially. The formulations illustratively listed in Table 16 below each contain a cationic surfactant and a nonionic surfactant. Similar formulations can be made with the cationic surfactant only. Cationic surfactants used are:

Methyl bis(2-hydroxyethyl)cocoammonium chloride, 35% in water (Ethoquad™ C/12W of Akzo).

Polyoxyethylene alkyletheramine (Surfactant B as described in Example I 1).

Nonionic surfactants used are:

Polyoxyethylene (7) $C_{10-12}$ linear alcohol (Witconol™ SN-90 of Witco).

Polyoxyethylene (5) $C_{11}$ linear alcohol (Neodol™ 1-5 of Shell).

Polyoxyethylene (7) $C_{11}$ linear alcohol (Neodol™ 1-7 of Shell).

Polyoxyethylene (8) $C_{11-12}$ linear alcohol (Surfonic™ L12-8 of Huntsman).

Polyoxyethylene (5) $C_{12-13}$ linear alcohol (Neodol™ 23-5 of Shell).

Polyoxyethylene (6.5) $C_{12-14}$ linear alcohol (Surfonic™ L24-6.5 of Huntsman).

Polyoxyethylene (7) $C_{12-15}$ linear alcohol (Neodol™ 25-7 of Shell).

Polyoxyethylene (9) $C_{12}C_{15}$ linear alcohol (Neodol™ 25-9 of Shell).

$C_{8-10}$ alkyl polyglucoside, 1.5 moles glucose (Agrimul™ PG 2076 of Henkel).

TABLE 16

| Formulation no. | Cationic surfactant | Cationic surf., g/l | Nonionic surfactant | Nonionic surf., g/l | Compound 17, g/l |
|---|---|---|---|---|---|
| F6 | Ethoquad C/12W | 32 | Neodol 25-7 | 16 | 2.1 |
| F7 | Ethoquad C/12W | 32 | Neodol 25-9 | 16 | 2.1 |
| F8 | Ethoquad C/12W | 32 | Surfonic L24-6.5 | 16 | 2.1 |
| F9 | Ethoquad C/12W | 32 | Surfonic L12-8 | 16 | 2.1 |
| F10 | Ethoquad C/12W | 32 | Witconol SN-90 | 16 | 2.1 |
| F11 | Ethoquad C/12W | 32 | Neodol 23-5 | 16 | 2.1 |
| F12 | Ethoquad C/12W | 40 | Surfonic L24-6.5 | 20 | 2.1 |
| F13 | Ethoquad C/12W | 40 | Surfonic L12-8 | 20 | 2.1 |
| F14 | Ethoquad C/12W | 40 | Neodol 23-5 | 20 | 2.1 |
| F15 | Ethoquad C/12W | 48 | Surfonic L24-6.5 | 12 | 2.1 |
| F16 | Ethoquad C/12W | 48 | Surfonic L12-8 | 12 | 2.1 |
| F17 | Ethoquad C/12W | 48 | Neodol 23-5 | 12 | 2.1 |
| F18 | Surfactant B | 64 | Neodol 1-5 | 16 | 2.1 |
| F19 | Surfactant B | 64 | Witconol SN-90 | 16 | 2.1 |
| F20 | Surfactant B | 64 | Surfonic L24-6.5 | 16 | 2.1 |
| F21 | Surfactant B | 64 | Agrimul PG 2076 | 16 | 2.1 |

TABLE 16-continued

| Formulation no. | Cationic surfactant | Cationic surf., g/l | Nonionic surfactant | Nonionic surf., g/l | Compound 17, g/l |
|---|---|---|---|---|---|
| F22 | Surfactant B | 64 | Agrimul PG 2076 | 16 | 4.2 |
| F23 | Surfactant B | 64 | Neodol 25-7 | 16 | 2.1 |
| F24 | Surfactant B | 96 | Surfonic L24-6.5 | 24 | 2.1 |
| F25 | Surfactant B | 96 | Neodol 1-7 | 24 | 2.1 |
| F26 | Surfactant B | 96 | Neodol 1-5 | 24 | 2.1 |

All of the above formulations were diluted in water and applied to plants in greenhouse tests. All showed acceptable physical stability when stored at room temperature for at least one week. Cloud points of all the above formulations were higher than 50° C. All had a characteristic odor of cinnamon, imparted by the presence of α-methyl-trans-cinnamaldehyde.

Example 17

A field test was conducted on bermudagrass (Cynodon dactylon, CYNDA) in a citrus plantation in Brazil. CYNDA plants were well developed. The following glyphosate formulations were diluted in water and applied in a spray volume of 100 l/ha: ROUNDUP® ULTRA of Monsanto Company, containing 41% by weight of isopropylammonium glyphosate (about 360 g a.e./l) together with a surfactant, as a commercial standard, Formulation F8 as described in Example 16, and Formulation B8, which is a "blank" formulation identical to F8 except that α-methyl-trans-cinnamaldehyde is replaced by additional water. A randomized block experimental design was used with 3 replications. Herbicidal effectiveness was recorded as percent inhibition 15, 30 and 45 days after treatment (DAT), based on visual examination by a single practiced technician.

Treatments and corresponding percent inhibitions, averaged for all replicates of each treatment, are given in Table 17.

TABLE 17 percent inhibition of CYNDA

| Formulation | Rate (g a.e./ha) | 15 DAT | 30 DAT | 45 DAT |
|---|---|---|---|---|
| Roundup ® Ultra | 1080 | 67 | 73 | 79 |
|  | 1440 | 86 | 96 | 96 |
|  | 1800 | 90 | 97 | 99 |
| B8 | 1080 | 63 | 78 | 77 |
|  | 1440 | 81 | 90 | 91 |
|  | 1800 | 89 | 98 | 98 |
| F8 | 1080 | 63 | 76 | 79 |
|  | 1440 | 80 | 90 | 92 |
|  | 1800 | 92 | 98 | 97 |

Example 18

A field test was conducted on Brachiaria decumbens (BRADC) on a research farm in Brazil. BRADC plants were well developed, 80–120 cm in height and beginning to flower. Formations tested were as in Example 17.

Treatments and corresponding percent inhibitions, averaged for all replicates of each treatment, are given in Table 18.

TABLE 18 percent inhibition of BRADC

| Formulation | Rate (g a.e./ha) | 15 DAT | 30 DAT | 45 DAT |
|---|---|---|---|---|
| Roundup ® Ultra | 1080 | 84 | 95 | 95 |
|  | 1440 | 90 | 98 | 97 |
|  | 1800 | 94 | 99 | 99 |
| B8 | 1080 | 69 | 88 | 81 |
|  | 1440 | 78 | 95 | 93 |
|  | 1800 | 90 | 98 | 97 |
| F8 | 1080 | 85 | 84 | 95 |
|  | 1440 | 94 | 97 | 97 |
|  | 1800 | 98 | 99 | 99 |

Example 19

A field test was conducted on goosegrass (Eleusine indica, ELEIN) on a research farm in Brazil. ELEIN plants were in flower. Formulations tested were as in Example 17. Evaluation took place 15 and 30 days after treatment.

Treatment and corresponding percent inhibitions, averaged for all replicates of each treatment, are given in Table 19.

TABLE 19 percent inhibition of ELEIN

| Formulation | Rate (g a.e./ha) | 15 DAT | 30 DAT |
|---|---|---|---|
| Roundup ® Ultra | 270 | 69 | 79 |
|  | 360 | 82 | 95 |
|  | 540 | 87 | 99 |
| B8 | 270 | 63 | 72 |
|  | 360 | 77 | 92 |
|  | 540 | 83 | 98 |
| F8 | 270 | 63 | 77 |
|  | 360 | 78 | 93 |
|  | 540 | 84 | 98 |

Example 20

A field test was conducted on wild poinsettia (Euphorbia heterophylla, EPHHL) and morningglory (Ipomoea aristolochiaefolia, IPOAO) on a research farm in Brazil. EPHHL and IPOAO plants were well developed and flowering. Formulations tested were as in Example 17. Evaluations took place 15 and 30 days after treatment.

Treatments and corresponding percent inhibitions, averaged for all replicates of each treatment, are given in Table 20.

TABLE 20 percent inhibition of EPHHL and IPOAO

| Formulation | Rate (g a.e./ha) | EPHHL 15 DAT | EPHHL 30 DAT | IPOAO 15 DAT | IPOAO 30 DAT |
|---|---|---|---|---|---|
| Roundup ® Ultra | 360 | 89 | 89 | 83 | 84 |
| | 720 | 97 | 97 | 89 | 95 |
| | 1080 | 98 | 99 | 96 | 98 |
| B8 | 360 | 87 | 87 | 79 | 81 |
| | 720 | 93 | 95 | 86 | 86 |
| | 1080 | 97 | 98 | 93 | 96 |
| F8 | 360 | 87 | 88 | 81 | 81 |
| | 720 | 94 | 95 | 90 | 92 |
| | 1080 | 96 | 97 | 94 | 94 |

Example 21

A field test was conducted on beggarticks (Bidens pilosa, BIDRA) and smooth pigweed (*Amaranthus hybridus*, AMACH) on a research farm in Brazil. BIDRA and AMACH plants were flowering. Formulations tested were as in Example 17. Evaluation took place 15 and 30 days after treatment.

Treatments and corresponding percent inhibitions, averaged for all replicates of each treatment, are given in Table 21.

TABLE 21 percent inhibition of BIDRA and AMACH

| Formulation | Rate (g a.e./ha) | BIDRA 15 DAT | BIDRA 30 DAT | AMACH 15 DAT | AMACH 30 DAT |
|---|---|---|---|---|---|
| Roundup ® Ultra | 360 | 68 | 75 | 16 | 27 |
| | 720 | 86 | 87 | 60 | 77 |
| | 1080 | 89 | 96 | 69 | 86 |
| B8 | 360 | 62 | 72 | 11 | 23 |
| | 720 | 81 | 84 | 50 | 69 |
| | 1080 | 87 | 95 | 68 | 81 |
| F8 | 360 | 63 | 76 | 20 | 25 |
| | 720 | 85 | 83 | 63 | 72 |
| | 1080 | 89 | 95 | 68 | 82 |

The data of Examples 17–21 are illustrative of the ability of α-methyl-trans-cinnamaldehyde, in very low amounts, to provide useful enhancement of glyphosate herbicidal effectiveness on some species under field conditions. Formulation B8, which contains no α-methyl-trans-cinnamaldehyde, showed slightly weaker herbicidal effectiveness at the last evaluation than the commercial standard, Roundup® Ultra, particularly on BARDC (Table 14). With Formulation F8, which contains α-methyl-trans-cinnamaldehyde at a weight/weight ratio to glyphosate a.e. of 1:229, performance equal to the commercial standard was substantially restored. In this case, α-methyl-trans-cinnamaldehyde provides an enabling means to concentrate glyphosate from the 360 g a.e./l loading of the commercial standard to 480 g a.e./l, through use of a different surfactant system at lower concentration, yet without sacrificing herbicidal effectiveness. On no species tested did α-methyl-trans-cinnamaldehyde reduce the herbicidal a significant degree.

Example 22

A test to compare tank-mix (i.e. simultaneous) versus sequential applications of glyphosate and compound 17 (α-methyl-trans-cinnamaldehyde) was conducted using the procedure of Example 2 except where otherwise noted.

The glyphosate formulation used was ACCORD® herbicide of Monsanto Company, an aqueous concentrate containing 41% by weight isopropylammonium glyphosate (about 360 g a.e./l) and no surfactant. In each case the polyoxyethylene tallowamine based surfactant MON 0818 of Monsanto Company was added at 0.05% by volume to the glyphosate spray solution. In some treatments compound 17 was added in tank-mix to the glyphosate spray solution exactly as in Example 2. In other treatments, compound 17 was applied as a separate application in 93 l/ha water, either before or after the glyphosate application. For these sequential applications, the time interval was in the range from 3 to 4 hours in each case.

Applications were made 16 days after planting ABUTH and 19 days after planting ECHCF. Evaluation took place 18 days after treatment. Treatments and corresponding percent inhibitions, averaged for all replicates of each treatment, are given in Table 22.

TABLE 22

| Glyphosate rate (g a.e./ha) | Compound 17 rate (g/ha) | Relative timing | % inhibition ABUTH | % inhibition ECHCF |
|---|---|---|---|---|
| 350 | 0 | | 60 | 68 |
| 450 | 0 | | 68 | 76 |
| 550 | 0 | | 79 | 81 |
| 650 | 0 | | 84 | 91 |
| 850 | 0 | | 89 | 98 |
| 350 | 5 | simultaneous | 63 | 79 |
| 350 | 20 | | 61 | 76 |
| 350 | 50 | | 58 | 70 |
| 450 | 5 | simultaneous | 68 | 89 |
| 450 | 20 | | 65 | 86 |
| 450 | 50 | | 65 | 89 |
| 350 | 5 | compound 17 | 63 | 91 |
| 350 | 20 | before | 64 | 91 |
| 350 | 50 | glyphosate | 65 | 59 |
| 450 | 5 | compound 17 | 65 | 90 |
| 450 | 20 | before | 68 | 96 |
| 450 | 50 | glyphosate | 63 | 85 |
| 350 | 5 | compound 17 | 55 | 80 |
| 350 | 20 | after | 54 | 79 |
| 350 | 50 | glyphosate | 53 | 66 |
| 450 | 5 | compound 17 | 56 | 79 |
| 450 | 20 | after | 58 | 75 |
| 450 | 50 | glyphosate | 60 | 74 |

Compound 17 in this study enhanced the herbicidal effectiveness of glyphosate on ECHCF when applied simultaneously with, as a pre-treatment before the glyphosate or as a post-treatment after the glyphosate. Best results were obtained with pre-treatment.

Example 23

The procedure of Example 2 was followed, except where noted below. Herbicides used were as follows:

Glyphosate, isopropylammonium salt (ACCORD®, Monsanto Company)

Paraquat dichloride (GRAMOXONE®, Zeneca)

Glufosinate, ammonium salt (IGNITE®, AgrEvo)

2,4-D, butoxyethyl ester (WEEDONE® LV4, Rhone-Poulenc)

Oxyfluorfen (GOAL®, Rohm & Haas)

Imazethapyr (PURSUIT®, AHP)

The above herbicides were applied without added surfactant, except in the case of the glyphosate product, to which the polyoxyethylene tallowamine based surfactant MON 0818 of Monsanto Company was added at 0.05% by volume of the spray solution. Compound 17 was added in tank-mix to the herbicide spray solution exactly as in Example 2.

Applications were made 18 days after planting ABUTH and 21 days after planting ECHCF. Evaluation took place 19 days after treatment. Treatments and corresponding percent inhibitions, averaged for all replicates of each treatment, are given in Table 23.

TABLE 23

| Herbicide | Herbicide rate (g a.e. or a.i./ha) | Compound 17 rate (g/ha) | % inhibition ABUTH | % inhibition ECHCF |
|---|---|---|---|---|
| glyphosate | 200 | 0 | 53 | 59 |
|  | 300 | 0 | 64 | 80 |
|  | 400 | 0 | 86 | 89 |
|  | 600 | 0 | 90 | 97 |
| glyphosate | 200 | 5 | 48 | 65 |
|  | 200 | 20 | 48 | 74 |
|  | 200 | 50 | 55 | 71 |
| glyphosate | 300 | 5 | 56 | 74 |
|  | 300 | 20 | 64 | 78 |
|  | 300 | 50 | 69 | 85 |
| paraquat | 200 | 0 | 58 | 66 |
|  | 300 | 0 | 100 | 83 |
|  | 400 | 0 | 88 | 83 |
|  | 600 | 0 | 100 | 90 |
| paraquat | 200 | 5 | 60 | 63 |
|  | 200 | 20 | 80 | 70 |
|  | 200 | 50 | 65 | 80 |
| paraquat | 300 | 5 | 73 | 75 |
|  | 300 | 20 | 75 | 69 |
|  | 300 | 50 | 73 | 78 |
| glufosinate | 200 | 0 | 80 | 84 |
|  | 300 | 0 | 80 | 96 |
|  | 400 | 0 | 80 | 95 |
|  | 600 | 0 | 93 | 100 |
| glufosinate | 200 | 5 | 75 | 73 |
|  | 200 | 20 | 69 | 88 |
|  | 200 | 50 | 76 | 90 |
| glufosinate | 300 | 5 | 90 | 98 |
|  | 300 | 20 | 79 | 90 |
|  | 300 | 50 | 80 | 89 |
| 2,4-D | 80 | 0 | 49 | 8 |
|  | 160 | 0 | 66 | 19 |
|  | 300 | 0 | 73 | 28 |
|  | 600 | 0 | 86 | 49 |
| 2,4-D | 80 | 5 | 48 | 18 |
|  | 80 | 20 | 38 | 9 |
|  | 80 | 50 | 51 | 10 |
| 2,4-D | 160 | 5 | 76 | 19 |
|  | 160 | 20 | 68 | 19 |
|  | 160 | 50 | 68 | 28 |
| oxyfluorfen | 80 | 0 | 81 | 45 |
|  | 160 | 0 | 89 | 66 |
|  | 300 | 0 | 94 | 85 |
|  | 600 | 0 | 99 | 90 |
| oxyfluorfen | 80 | 5 | 93 | 34 |
|  | 80 | 20 | 91 | 58 |
|  | 80 | 50 | 91 | 53 |
| oxyfluorfen | 160 | 5 | 94 | 46 |
|  | 160 | 20 | 92 | 68 |
|  | 160 | 50 | 94 | 76 |
| imazethapyr | 10 | 0 | 61 | 66 |
|  | 20 | 0 | 59 | 70 |
|  | 40 | 0 | 54 | 69 |
|  | 80 | 0 | 60 | 76 |
| imazethapyr | 10 | 5 | 33 | 70 |
|  | 10 | 20 | 31 | 59 |
|  | 10 | 50 | 30 | 31 |
| imazethapyr | 20 | 5 | 36 | 54 |
|  | 20 | 20 | 41 | 43 |
|  | 20 | 50 | 40 | 49 |

It is believed that an error occurred in the imazethapyr treatments resulting in no apparant rate response in either ABUTH or ECHCF over an eightfold range of rates. Accordingly the data for imazethapyr in Example 23 should be disregarded.

The preceding description of specific embodiments of the invention is not intended to be a complete list of every possible embodiment of the invention. People skilled in the art will recognize that modifications can be made to the specific embodiments described herein without departing from the scope of the present invention.

What is claimed is:

1. A plant treatment composition for application to foliage of a plant, comprising (a) an application medium, having dissolved or dispersed therein (b) a biologically effective amount of a herbicide, and (c) a phenyl-substituted olefin compound having a molecular weight of about 100 to about 300, and having a molecular structure that comprises a phenyl ring linked to an olefinic carbon chain, said olefinic carbon chain being other than part of a ring structure fused to said phenyl ring and having an ethylenic double bond whose proximal carbon atom is the first or second carbon atom in the chain from said phenyl ring;

wherein, when the composition is applied to the foliage, said phenyl-substituted olefin compound is present in a substantially non-phytotoxic amount of at least about 0.25 g/ha but not in an amount sufficient to antagonize biological effectiveness of the herbicide.

2. The composition of claim 1 wherein the application medium is water.

3. The composition of claim 1 wherein the phenyl-substituted olefin compound is present in an amount such that when the composition is applied to foliage of a plant at a biologically effective rate of the herbicide, the phenyl-substituted olefin compound is applied at a rate of about 0.25 to about 250 g/ha.

4. The composition of claim 1 wherein the phenyl-substituted olefin compound is present in an amount such that when the composition is applied to foliage of a plant at a biologically effective rate of the herbicide, the phenyl-substituted olefin compound is applied at a rate of about 1 to about 25 g/ha.

5. The composition of claim 1 that further comprises one or more surfactants in a total surfactant amount sufficient to enhance biological effectiveness of the herbicide.

6. A plant treatment composition for application to foliage of a plant, comprising (a) water as an application medium, having dissolved or dispersed therein (b) a biologically effective amount of a herbicide, and (c) a phenyl-substituted olefin compound having a molecular weight of about 100 to about 300, and having a structure corresponding to formula (I) or (II):

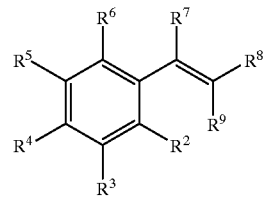

(I)

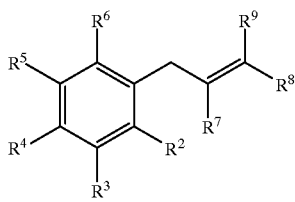

(II)

wherein:
R² and R⁶ are independently hydrido, hydroxy or hydrocarbyloxy groups;
R³, R⁴ and R⁵ are independently hydrido, halogen, hydroxy, hydrocarbyl, hydrocarbyloxy, phenyl, phenylhydrocarbyloxy, hydroxyhydrocarbyl, halocarbyl, halohydrocarbyl, cyano, amino, nitro, or —COOR¹¹ groups where R¹¹ is a hydrido, hydrocarbyl, phenyl or phenylhydrocarbyl group; or two adjacent R groups among R³, R⁴ and R⁵ form a hydrocarbylenedioxy bridge;
R⁷ and R⁹ are independently hydrido, hydroxy, hydrocarbyl, phenyl, cyano, or -COOR¹² groups where R¹² is a hydrido, hydrocarbyl, phenyl or phenylhydrocarbyl group, or R⁷ together with R⁸ and the carbon atoms linked by the ethylenic double bond of formula (I) or formula (II) forms a cyclopentenedione ring substituent of formula (III):

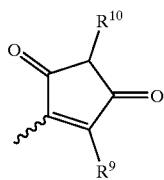

(III)

wherein the wavy line depicts the bond adjacent to the ethylenic double bond proximal to the phenyl ring of formula (I) or formula (II), R⁹ is as defined above and R¹⁰ is a hydrido, hydrocarbyl, phenyl or cyano group;
R⁸, unless forming said cyclopentenedione ring with R⁷, is a hydrido, hydrocarbyl, phenyl, phenylhydrocarbyl, cyano, amino, phenylamino, —ZOR¹⁵, —ZOCOR¹⁵, —CHO, —CO-hydrocarbyl, —CO-phenyl, —CO-furanyl, —COOR¹⁵, —CONR¹⁵R¹⁶, —CONHN=CH-phenyl, —ZNR¹⁵R¹⁶, —CH=NOH, or —CH=C(CN)COOR¹⁵ group, or a group of formula (IV):

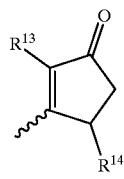

(IV)

wherein R¹³ is —CH₂COOR¹⁵ and R¹⁴ is a hydrido, hydroxy or hydrocarbyloxy group;
where Z is a C₁₋₁₆ hydrocarbylene group, and R¹⁵ and R¹⁶ are independently selected from hydrido, hydrocarbyl, phenyl and phenylhydrocarbyl groups; and R⁸ and R⁹ are stereochemically interchangeable;
wherein hydrocarbyl, hydrocarbyloxy, halocarbyl, halohydrocarbyl, hydroxyhydrocarbyl, hydrocarboyl and hydrocarbylenedioxy groups contain 1 to 6 carbon atoms and comprise a saturated or unsaturated linear or branched aliphatic or a saturated or unsaturated alicyclic structure;
wherein phenyl groups are themselves optionally and independently substituted at one or more positions with amino, carbamoyl, hydrocarbyl or hydrocarbyloxy groups;
and wherein phenylhydrocarbyl, phenylhydrocarboyl, phenylhydrocarbyloxy and phenylamino substituents comprise a phenyl substituent linked to a hydrocarbyl, hydrocarboyl, hydrocarbyloxy or amino group respectively;
wherein, when the composition is applied to the foliage, said phenyl-substituted olefin compound is present in a substantially non-phytotoxic amount of at least about 0.25 g/ha but not in an amount sufficient to antagonize biological effectiveness of the herbicide.

7. The composition of claim 6 wherein:
R² and R⁶ substituents are independently hydrido, hydroxy or methoxy groups with at least one of R² and R⁶ being a hydrido group;
R³ and R⁵ substituents, except where either forms a methylenedioxy bridge with R⁴, are independently hydrido, methyl, hydroxy or methoxy groups, with at least one of R³ and Rs being a hydrido group, and wherein one of R³ and R⁵ is a methyl or methoxy group when R⁴ is a hydroxy group;
R⁴ is a hydrido, halogen, methyl, ethyl, hydroxy, methoxy, benzyloxy, trifluoromethyl, amino or nitro group, or R⁴ forms a methylenedioxy bridge with R³ or R⁵;
R⁷ is a hydrido or C₁₋₃ alkyl group, or R⁷ together with R⁸ and the carbon atoms linked by the ethylenic double bond of formula (I) or formula (II) form a cyclopentenedione ring substituent of formula (III) wherein R⁹ is a hydroxy group and R¹⁰ is a hydrido group;
R⁸, unless forming said cyclopentenedione ring with R⁷, is hydrido, methyl, hydroxy-C₁₋₂ alkyl or the acetate ester thereof, cyano, anilino, carbamoyl, —CONHN=CH—(4-methoxy)phenyl, —CONHN=CH—(4-acetamido)phenyl, —COOR¹⁷ where R¹⁷ is a hydrido, methyl, ethyl, allyl, unsubstituted phenyl or benzyl group, or —COR¹⁸ where R¹⁸ is a hydrido, C₁₋₃ alkyl, unsubstituted phenyl or 4-methylphenyl group;
R⁹, except where R⁷ and R⁸ form said cyclopentenedione ring, is a hydrido, hydroxy, C₁₋₆ alkyl, cyano, —COOH or —COCH₃ group; and
R⁸ and R⁹ are stereochemically interchangeable.

8. The composition of claim 7 wherein the phenyl-substituted olefin compound is safrole.

9. The composition of claim 7 wherein the phenyl-substituted olefin compound displays stereoisomerism and is present predominantly as the trans isomer.

10. The composition of claim 7 wherein the phenyl-substituted olefin compound has a structure corresponding to formula (V):

(V)

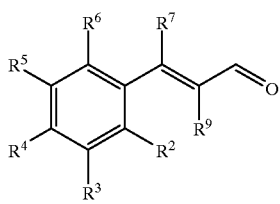

or a stereochemical isomer thereof, wherein $R^7$ and $R^9$ are independently hydrido or $C_{1-6}$ alkyl groups, $R^2$, $R^3$, $R^4$, $R^5$ and $R^6$ are independently hydrido, hydroxy or methoxy groups with at least three $R^2$ to $R^6$ substituents being hydrido groups and no more than one $R^2$ to $R^6$ substituent being a hydroxy group.

11. The composition of claim 10 wherein the phenyl-substituted olefin compound is α-methylcinnamaldehyde.

12. The composition of claim 10 wherein the phenyl-substituted olefin compound is α-methyl-trans-cinnamaldehyde.

13. A concentrate composition for application to foliage of a plant upon dilution, dispersion or dissolution in water, comprising (a) a herbicide; and (b) a phenyl-substituted olefin compound having a molecular weight of about 100 to about 300, and having a molecular structure that comprises a phenyl ring linked to an olefinic carbon chain, said olefinic carbon chain being other than part of a ring structure fused to said phenyl ring and having an ethylenic double bond whose proximal carbon atom is the first or second carbon atom in the chain from said phenyl ring;

said concentrate composition, when diluted, dissolved or dispersed in water and applied to the foliage, providing said herbicide in a biologically effective amount and said phenyl-substituted olefin compound in a substantially non-phytotoxic amount of at least about 0.25 g/ha but not in an amount sufficient to antagonize biological effectiveness of said herbicide.

14. A concentrate composition for application to foliage of a plant upon dilution, dispersion or dissolution in water, comprising (a) a biologically effective amount of a herbicide;

(b) a phenyl-substituted olefin compound having a molecular weight of about 100 to about 300, and having a structure corresponding to formula (I) or (II):

(I)

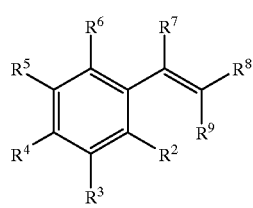

-continued (II)

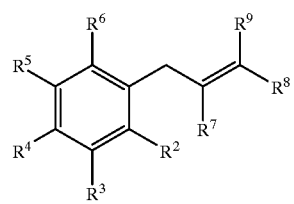

wherein:

$R^2$ and $R^6$ are independently hydrido, hydroxy or hydrocarbyloxy groups;

$R^3$, $R^4$ and $R^5$ are independently hydrido, halogen, hydroxy, hydrocarbyl, hydrocarbyloxy, phenyl, phenylhydrocarbyloxy, hydroxyhydrocarbyl, halocarbyl, halohydrocarbyl, cyano, amino, nitro, or —COOR$^{11}$ groups where $R^{11}$ is a hydrido, hydrocarbyl, phenyl or phenylhydrocarbyl group; or two adjacent R groups among $R^3$, $R^4$ and $R^5$ form a hydrocarbylenedioxy bridge;

$R^7$ and $R^9$ are independently hydrido, hydroxy, hydrocarbyl, phenyl, cyano, or —COOR$^{12}$ groups where $R^{12}$ is a hydrido, hydrocarbyl, phenyl or phenylhydrocarbyl group, or $R^7$ together with $R^8$ and the carbon atoms linked by the ethylenic double bond of formula (I) or formula (II) form a cyclopentenedione ring substituent of formula (III):

(III)

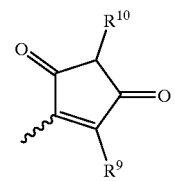

wherein the wavy line depicts the bond adjacent to the ethylenic double bond proximal to the phenyl ring of formula (I) or formula (II), $R^9$ is as defined above and $R^{10}$ is a hydrido, hydrocarbyl, phenyl or cyano group;

$R^8$, unless forming said cyclopentenedione ring with $R^7$, is a hydrido, hydrocarbyl, phenyl, phenylhydrocarbyl, cyano, amino, phenylamino, —ZOR$^{15}$, —ZOCOR$^{15}$, —CHO, —CO-hydrocarbyl, —CO-phenyl, —CO-furanyl, —COOR$^{15}$, —CONR$^{15}$R$^{16}$, —CONRHN=CH-phenyl, —ZNR$^{15}$R$^{16}$, —CH=NOH, or —CH=C(CN)COOR$^{15}$ group, or a group of formula (IV):

(IV)

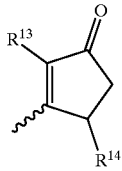

wherein $R^{13}$ is —CH$_2$COOR$^{15}$ and $R^{14}$ is a hydrido, hydroxy or hydrocarbyloxy group; where Z is a $C_{1-6}$ hydrocarbylene group, and $R^{15}$ and $R^{16}$ are independently selected from hydrido, hydrocarbyl, phenyl and phenylhydrocarbyl groups; and $R^8$ and $R^9$ are stereochemically interchangeable;

wherein hydrocarbyl, hydrocarbyloxy, halocarbyl, halohydrocarbyl, hydroxyhydrocarbyl, hydrocarboyl and hydrocarbylenedioxy groups contain 1 to 6 carbon atoms and comprise a saturated or unsaturated linear or branched aliphatic or a saturated or unsaturated alicyclic structure;

wherein phenyl groups are themselves optionally and independently substituted at one or more positions with amino, carbamoyl, hydrocarbyl or hydrocarbyloxy groups;

and wherein phenylhydrocarbyl, phenylhydrocarboyl, phenylhydrocarbyloxy and phenylamino substituents comprise a phenyl substituent linked to a hydrocarbyl, hydrocarboyl, hydrocarbyloxy or amino group respectively;

said concentrate composition, when diluted, dispersed or dissolved in water and applied to the foliage, providing said herbicide in a biologically effective amount and said phenyl-substituted olefin compound in a substantially non-phytotoxic amount of at least about 0.25 g/ha but not in an amount sufficient to antagonize biological effectiveness of said herbicide.

15. The composition of claim 14 wherein:

$R^2$ and $R^6$ substituents are independently hydrido, hydroxy or methoxy groups with at least one of $R^2$ and $R^6$ being a hydrido group;

$R^3$ and $R^5$ substituents, except where either forms a methylenedioxy bridge with $R^4$, are independently hydrido, methyl, hydroxy or methoxy groups, with at least one of $R^3$ and $R^5$ being a hydrido group, and wherein one of $R^3$ and $R^5$ is a methyl or methoxy group when $R^4$ is a hydroxy group;

$R^4$ is a hydrido, halogen, methyl, ethyl, hydroxy, methoxy, benzyloxy, trifluoromethyl, amino or nitro group, or $R^4$ forms a methylenedioxy bridge with $R^3$ or $R^5$;

$R^7$ is a hydrido or $C_{1-3}$ alkyl group, or $R^7$ together with $R^8$ and the carbon atoms linked by the ethylenic double bond of formula (I) or formula (II) form a cyclopentenedione ring substituent of formula (III) wherein $R^9$ is a hydroxy group and $R^{10}$ is a hydrido group;

$R^8$ unless forming said cyclopentenedione ring with $R^7$, is hydrido, methyl, hydroxy-$C_{1-2}$ alkyl or the acetate ester thereof, cyano, anilino, carbamoyl, —CONHN=CH—(4-methoxy)phenyl, —CONHN=CH—(4-acetamido) phenyl, —COOR$^{17}$ where $R^{17}$ is a hydrido, methyl, ethyl, allyl, unsubstituted phenyl or benzyl group, or —COR$^{18}$ where $R^{18}$ is a hydrido, $C_{1-3}$ alkyl, unsubstituted phenyl or 4-methylphenyl group;

$R^9$, except where $R^7$ and $R^8$ form said cyclopentenedione ring, is a hydrido, hydroxy, $C_{1-6}$ alkyl, cyano, —COOH or —COCH$_3$ group; and $R^8$ and $R^9$ are stereochemically interchangeable.

16. The composition of claim 15 wherein the phenyl-substituted olefin compound is safrole.

17. The composition of claim 15 wherein the phenyl-substituted olefin compound displays stereoisomerism and is present predominantly as the trans isomer.

18. The composition of claim 15 wherein the phenyl-substituted olefin compound has a structure corresponding to formula (V):

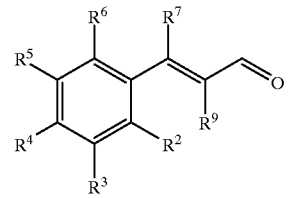

or a stereochemical isomer thereof, wherein $R^7$ and $R^9$ are independently hydrido or $C_{1-6}$ alkyl groups, $R^2$, $R^3$, $R^4$, $R^5$ and $R^6$ are independently hydrido, hydroxy or methoxy groups with at least three $R^2$ to $R^6$ substituents being hydrido groups and no more than one $R^2$ to $R^6$ substituent being a hydroxy group.

19. The composition of claim 18 wherein the phenyl-substituted olefin compound is α-methylcinnamaldehyde.

20. The composition of claim 18 wherein the phenyl-substituted olefin compound is α-methyl-trans-cinnamaldehyde.

21. The concentrate composition of claim 14 wherein the phenyl-substituted olefin compound is present in an amount such that when the concentrate composition is diluted, dispersed or dissolved in water and applied to the foliage at a biologically effective rate of the herbicide, the phenyl-substituted olefin compound is applied at a rate of about 0.25 to about 250 g/ha.

22. The concentrate composition of claim 14 wherein the phenyl-substituted olefin compound is present in an amount such that when the concentrate composition is diluted, dispersed or dissolved in water and applied to the foliage at a biologically effective rate of the herbicide, the phenyl-substituted olefin compound is applied at a rate of about 1 to about 25 g/ha.

23. The concentrate composition of claim 14 that further comprises water and one or more surfactants in a total surfactant amount sufficient to emulsify the phenyl-substituted olefin compound in the water.

24. The concentrate composition of claim 14 wherein the phenyl-substituted olefin compound imparts an organoleptically acceptable odor to the composition.

25. The concentrate composition of claim 24 wherein the compound is α-methyl-trans-cinnamaldehyde and is present in an amount of about 1 to about 5 g/l.

26. A herbicidal spray composition comprising
(a) a herbicidally effective amount of an alkali metal, ammonium, $C_{1-16}$ alkylammonium, $C_{1-16}$ alkanolammonium or $C_{1-16}$ alkylsulfonium salt of N-phosphonomethylglycine;
(b) α-methyl-trans-cinnamaldehyde in an amount that, when the composition is applied to foliage of a plant, is sufficient to provide a rate of about 0.25 to about 250 g/ha;
(c) one or more surfactants in a total surfactant amount sufficient to enhance the herbicidal effectiveness of the N-phosphonomethylglycine; and
(d) water.

27. The composition of claim 26 wherein the salt of N-phosphonomethylglycine is a sodium, ammonium, dimethylammonium, isopropylammonium, monoethanolammonium or trimethylsulfonium salt.

28. The composition of claim 26 wherein the α-methyl-trans-cinnamaldehyde is present in an amount that, when the composition is applied to foliage of a plant, is sufficient to provide a rate of about 1 to about 25 g/ha.

29. The composition of claim 26 wherein at least one of the surfactants is other than anionic.

30. The composition of claim 26 wherein at least one of the surfactants is a nonionic surfactant selected from the group consisting of polyoxyalkylene $C_{8-24}$ alkyl, alkenyl and alkylaryl ethers having about 2 to about 100 $C_{2-4}$ alkylene oxide units, polyoxyalkylene $C_{8-24}$ alkyl and alkenyl esters having about 2 to about 100 $C_{2-4}$ alkylene oxide units, sorbitan $C_{8-24}$ alkyl esters, glyceryl $C_{8-24}$ alkyl esters, sucrose $C_{8-24}$ alkyl esters and $C_{8-24}$ alkyl polyglycosides.

31. The composition of claim 26 wherein at least one of the surfactants is a cationic surfactant selected from the group consisting of polyoxyalkylene tertiary $C_{8-24}$ alkylamines and alkenylamines, quaternary ammonium surfactants and polyoxyalkylene $C_{8-24}$ alkyletheramines.

32. The composition of claim 26 wherein at least one of the surfactants is an amphoteric surfactant selected from the group consisting of polyoxyalkylene $C_{8-24}$ alkylamine oxides having about 2 to about 100 $C_{2-4}$ alkylene oxide units, $C_{8-24}$ alkylbetaines and $C_{8-24}$ alkyl-substituted amino acids.

33. A liquid concentrate herbicidal composition comprising
 (a) about 50 to about 500 g a.e./l of an alkali metal, ammonium, $C_{1-16}$ alkylammonium, $C_{1-16}$ alkanolammonium or $C_{1-16}$ alkylsulfonium salt of N-phosphonomethylglycine;
 (b) cc-methyl-trans-cinnamaldehyde; and
 (c) water;
 wherein the α-methyl-trans-cinnamaldehyde is present in an amount sufficient, when the composition is further diluted in water and applied to foliage of a plant at a herbicidally effective rate of the N-phosphonomethylglycine, to provide a rate of about 0.25 to about 250 g/ha of α-methyl-trans-cinnamaldehyde.

34. The concentrate composition of claim 33 wherein the salt of N-phosphonomethylglycine is a sodium, ammonium, dimethylammonium, isopropylammonium, monoethanolammonium or trimethylsulfonium salt.

35. The concentrate composition of claim 33 wherein the α-methyl-trans-cinnamaldehyde is present in an amount sufficient, when the composition is further diluted in water and applied to foliage of a plant at a herbicidally effective rate of the N-phosphonomethylglycine, to provide a rate of about 1 to about 25 g/ha of α-methyl-trans-cinnamaldehyde.

36. A liquid concentrate herbicidal composition which is an emulsion having an aqueous phase and an oil phase, said composition comprising
 (a) about 50 to about 500 g a.e./l of an alkali metal, ammonium, $C_{1-16}$ alkylammonium, $C_{1-16}$ alkanolammonium or $C_{1-16}$ alkylsulfonium salt of N-phosphonomethylglycine; and
 (b) a phenyl-substituted olefin compound in an amount sufficient, when the composition is further diluted in water and applied to foliage of a plant at a herbicidally effective rate of the N-phosphonomethylglycine, to provide a rate of about 0.25 to about 250 g/ha of the phenyl-substituted olefin compound; and
 (c) one or more surfactants in an amount sufficient to emulsify the oil phase in the aqueous phase;
 wherein the N-phosphonomethylglycine is present primarily in the aqueous phase and the phenyl-substituted olefin compound is present primarily in the oil phase.

37. The concentrate composition of claim 36 wherein the salt of N-phosphonomethylglycine is a sodium, ammonium, dimethylammonium, isopropylammonium, monoethanolammonium or trimethylsulfonium salt.

38. The concentrate composition of claim 36 wherein the phenyl-substituted olefin compound is present in an amount sufficient, when the composition is further diluted in water and applied to foliage of a plant at a herbicidally effective rate of the N-phosphonomethylglycine, to provide a rate of about 1 to about 25 g/ha of the phenyl-substituted olefin compound.

39. The concentrate composition of claim 36 wherein the oil phase consists essentially of said phenyl-substituted olefin compound.

40. The concentrate composition of claim 36 wherein the phenyl-substituted olefin compound is α-methyl-trans-cinnamaldehyde.

41. The concentrate composition of claim 40 containing about 350 to about 500 g a.e./l of the N-phosphonomethylglycine.

42. The concentrate composition of claim 40 containing about 450 to about 500 g a.e./l of the N-phosphonomethylglycine.

43. A water-soluble or water-dispersible dry concentrate herbicidal composition comprising
 (a) about 5% a.e. to about 80% a.e. by weight of a sodium or ammonium salt of N-phosphonomethylglycine; and
 (b) α-methyl-trans-cinnamaldehyde;
 wherein the α-methyl-trans-cinnamaldehyde is present in an amount sufficient, when the composition is dissolved or dispersed in water and applied to foliage of a plant at a herbicidally effective rate of the N-phosphonomethylglycine, to provide a rate of about 0.25 to about 250 g/ha of α-methyl-trans-cinnamaldehyde.

44. The concentrate composition of claim 43 wherein the α-methyl-trans-cinnamaldehyde is present in an amount sufficient, when the composition is dissolved or dispersed in water and applied to foliage of a plant at a herbicidally effective rate of the N-phosphonomethylglycine, to provide a rate of about 1 to about 25 g/ha of α-methyl-trans-cinnamaldehyde.

45. The concentrate composition of claim 43 containing about 50% a.e. to about 80% a.e. of the N-phosphonomethylglycine.

46. A concentrate herbicidal composition comprising
 (a) about 1 to about 5 g/l of α-methyl-trans-cinnamaldehyde;
 (b) about 350 to about 500 g a.e./l of a sodium, ammonium, dimethylammonium, isopropylammonium, monoethanolammonium or trimethylsulfonium salt of N-phosphonomethylglycine;
 (c) one or more surfactants in a total surfactant amount sufficient to emulsify the α-methyl-trans-cinnamaldehyde; and
 (d) water.

47. The composition of claim 46 comprising about 450 to about 500 g a.e./l of the salt of N-phosphonomethylglycine.

48. The composition of claim 46 wherein at least one of the surfactants is a cationic surfactant selected from the group consisting of polyoxyalkylene tertiary $C_{8-24}$ alkylamines having about 2 to about 100 $C_{2-4}$ alkylene oxide units, quaternary ammonium surfactants and polyoxyalkylene $C_{8-24}$ alkyletheramines having about 2 to about 100 $C_{2-4}$ alkylene oxide units.

49. A process for enhancing reliability of biological effectiveness of a herbicide comprising the steps of
 (a) applying to foliage of a plant a phenyl-substituted olefin compound having a molecular weight of about 100 to about 300, and having a molecular structure that comprises a phenyl ring linked to an olefinic carbon chain, said olefinic carbon chain being other than part of a ring structure fused to said phenyl ring and having an ethylenic double bond whose proximal carbon atom is the first or second carbon atom in the chain from said phenyl ring; and (b) applying a biologically effective amount of the herbicide to said foliage; wherein the phenyl-substituted olefin compound is applied in a substantially non-phytotoxic amount of at least about 0.25 g/ha but not in an amount sufficient to antagonize biological effectiveness of the herbicide.

50. The process of claim 49 wherein step (b) occurs within about 24 hours before or after step (a).

51. The process of claim 49 wherein steps (a) and (b) occur simultaneously.

52. The process of claim 51 wherein the herbicide and the phenyl-substituted olefin compound are present in a single plant treatment composition prior to being applied to the foliage.

53. The process of claim 52 wherein said single plant treatment composition is prepared by diluting, dispersing or dissolving in an application medium a concentrate composition comprising (a) the herbicide, (b) the phenyl-substituted olefin compound and (c) suitable excipient ingredients.

54. A process for enhancing reliability of biological effectiveness of a herbicide comprising the steps of (a) applying to foliage of a plant a phenyl-substituted olefin compound having a molecular weight of about 100 to about 300, and having a structure corresponding to formula (I) or formula (11):

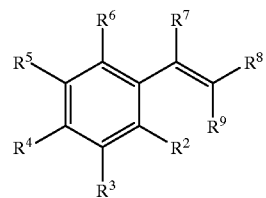

(I)

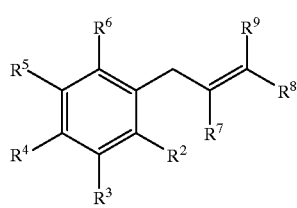

(II)

wherein:

$R^2$ and $R^6$ are independently hydrido, hydroxy or hydrocarbyloxy groups;

$R^3$, $R^4$ and Rs are independently hydrido, halogen, hydroxy, hydrocarbyl, hydrocarbyloxy, phenyl, phenylhydrocarbyloxy, hydroxyhydrocarbyl, halocarbyl, halohydrocarbyl, cyano, amino, nitro, or —COOR$^{11}$ groups where $R^{11}$ is a hydrido, hydrocarbyl, phenyl or phenylhydrocarbyl group, or two adjacent R groups among $R^3$, $R^4$ and $R^5$ form a hydrocarbylenedioxy bridge;

$R^7$ and $R^9$ are independently hydrido, hydroxy, hydrocarbyl, phenyl, cyano, or —COOR$^{12}$ groups where $R^{12}$ is a hydrido, hydrocarbyl, phenyl or phenylhydrocarbyl group, or $R^7$ together with $R^8$ and the carbon atoms linked by the ethylenic double bond of formula (1) or formula (II) form a cyclopentenedione ring substituent of formula (III):

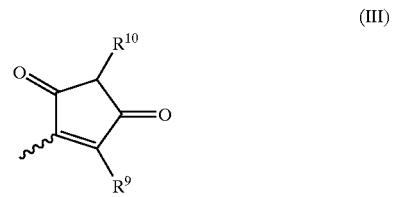

(III)

wherein the wavy line depicts the bond adjacent to the ethylenic double bond proximal to the phenyl ring of formula (I) or formula (II), $R^9$ is as defined above and $R^{10}$ is a hydrido, hydrocarbyl, phenyl or cyano group;

$R^8$, unless forming said cyclopentenedione ring with $R^7$, is a hydrido, hydrocarbyl, phenyl, phenylhydrocarbyl, cyano, amino, phenylamino, —ZOR$^{15}$, —ZOCOR$^{15}$, —CHO, —CO-hydrocarbyl, —CO-phenyl, —CO-furanyl, —COOR$^{15}$, —CONR$^{15}$R$^{16}$, —CONHN=CH-phenyl, —ZNR$^{15}$R$^{16}$, —CH=NOH, or —CH=C(CN)COOR$^{15}$ group, or a group of formula (IV):

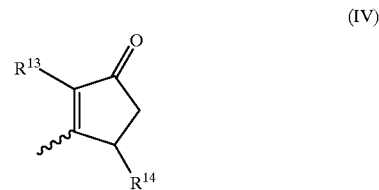

(IV)

wherein $R^{13}$ is —CH$_2$COOR$^{15}$ and $R^{14}$ is a hydrido, hydroxy or hydrocarbyloxy group; where Z is a $C_{1-6}$ hydrocarbylene group, and $R^{15}$ and $R^{16}$ are independently selected from hydrido, hydrocarbyl, phenyl and phenylhydrocarbyl groups; and $R^8$ and $R^9$ are stereochemically interchangeable;

wherein hydrocarbyl, hydrocarbyloxy, halocarbyl, halohydrocarbyl, hydroxyhydrocarbyl, hydrocarboyl and hydrocarbylenedioxy groups contain 1 to 6 carbon atoms and comprise a saturated or unsaturated linear or branched aliphatic or a saturated or unsaturated alicyclic structure;

wherein phenyl groups are themselves optionally and independently substituted at one or more positions with amino, carbamoyl, hydrocarbyl or hydrocarbyloxy groups;

and wherein phenylhydrocarbyl, phenylhydrocarboyl, phenylhydrocarbyloxy and phenylamino substituents comprise a phenyl substituent linked to a hydrocarbyl, hydrocarboyl, hydrocarbyloxy or amino group respectively; and (b) applying a biologically effective amount of the herbicide to said foliage; wherein the phenyl-substituted olefin compound is applied in a substantially non-phytotoxic amount of at least about 0.25 g/ha but not in an amount sufficient to antagonize biological effectiveness of the herbicide.

55. The process of claim 54 wherein:

$R^2$ and $R^6$ substituents are independently hydrido, hydroxy or methoxy groups with at least one of $R^2$ and $R^6$ being a hydrido group;

$R^3$ and $R^5$ substituents, except where either forms a methylenedioxy bridge with $R^4$, are independently hydrido, methyl, hydroxy or methoxy groups, with at least one of $R^3$ and $R^5$ being a hydrido group, and wherein one of $R^3$ and $R^5$ is a methyl or methoxy group when $R^4$ is a hydroxy group;

$R^4$ is a hydrido, halogen, methyl, ethyl, hydroxy, methoxy, benzyloxy, trifluoromethyl, amino or nitro group, or $R^4$ forms a methylenedioxy bridge with $R^3$ or $R^5$;

$R^7$ is a hydrido or $C_{1-3}$ alkyl group, or $R^7$ together with $R^8$ and the carbon atoms linked by the ethylenic double bond of formula (I) or formula (II) form a cyclopentenedione ring substituent of formula (III) wherein $R^9$ is a hydroxy group and $R^{10}$ is a hydrido group;

$R^8$, unless forming said cyclopentenedione ring with $R^7$, is hydrido, methyl, hydroxy-$C_{1-2}$ alkyl or the acetate ester thereof, cyano, anilino, carbamoyl, —CONHN═CH—(4-methoxy)phenyl, —CONHN═CH—(4-acetamido)phenyl, —COOR$^{17}$ where $R^{17}$ is a hydrido, methyl, ethyl, allyl, unsubstituted phenyl or benzyl group, or —COR$^{18}$ where $R^{18}$ is a hydrido, $C_{1-3}$ alkyl, unsubstituted phenyl or 4-methylphenyl group;

$R^9$, except where $R^7$ and $R^8$ form said cyclopentenedione ring, is a hydrido, hydroxy, $C_{1-6}$ alkyl, cyano, —COOH or —COCH$_3$ group; and $R^8$ and $R^9$ are stereochemically interchangeable.

56. The process of claim 55 wherein the phenyl-substituted olefin compound is safrole.

57. The process of claim 55 wherein the phenyl-substituted olefin compound displays stereoisomerism and is present predominantly as the trans isomer.

58. The process of claim 55 wherein the phenyl-substituted olefin compound has a structure corresponding to formula (V):

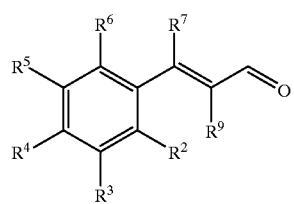

(V)

or a stereochemical isomer thereof, wherein $R^7$ and $R^9$ are independently hydrido or $C_{1-6}$ alkyl groups, $R^2$, $R^3$, $R^4$, $R^5$ and $R^6$ are independently hydrido, hydroxy or methoxy groups with at least three $R^2$ to $R^6$ substituents being hydrido groups and no more than one $R^2$ to $R^6$ substituent being a hydroxy group.

59. The process of claim 58 wherein the phenyl-substituted olefin compound is α-methylcinnamaldehyde.

60. The process of claim 50 wherein the phenyl-substituted olefin compound is α-methyl-trans-cinnamaldehyde.

61. The process of claim 54 wherein the phenyl-substituted olefin compound is applied at a rate of about 0.25 to about 250 g/ha.

62. The process of claim 54 wherein the phenyl-substituted olefin compound is applied at a rate of about 1 to about 25 g/ha.

63. A herbicidal process comprising the steps of
(i) mixing together (a) α-methyl-trans-cinnamaldehyde, (b) an alkali metal, ammonium, $C_{1-16}$ alkylammonium, $C_{1-6}$ alkanolammonium or $C_{1-16}$ alkylsulfonium salt of N-phosphonomethylglycine, (c) one or more surfactants in a total surfactant amount sufficient to emulsify the α-methyl-trans-cinnamaldehyde, and (d) water to form a concentrate composition,
(ii) diluting the concentrate composition in water to form a spray composition wherein the α-methyl-trans-cinnamaldehyde is present in an amount sufficient to provide a rate of about 0.25 to about 250 g/ha and the salt of N-phosphonomethylglycine is present in a herbicidally effective amount, and
(iii) spraying the spray composition on to foliage of a plant.

64. The process of claim 63 wherein the salt of N-phosphonomethylglycine is a sodium, ammonium, dimethylammonium, isopropylammonium, monoethanolammonium or trimethylsulfonium salt.

65. The process of claim 63 wherein the α-methyl-trans-cinnamaldehyde is present in the spray composition in an amount sufficient to provide a rate of about 1 to about g/ha.

66. The composition of claim 2 wherein the herbicide is a foliar-applied herbicide selected from aminotriazole, asulam, bentazon, bialaphos, bipyridyl herbicides, bromacil, clopyralid, cyclohexenone herbicides, diphenylether herbicides, fosamine, glufosinate, gllyphosate, hydroxybenzonitrile herbicides, imidazolinone herbicides, isoxaben, phenoxy herbicides, phenoxypropionate herbicides, picloram, substituted urea herbicides, sulfonylurea herbicides and triazine herbicides.

67. The composition of claim 2 wherein the herbicide is N-phosphonomethylglycine, a salt or ester thereof, or a compound which is converted to N-phosphonomethylglycine in plant tissues or which otherwise provides N-phosphonomethylglycine in ionic form.

68. The composition of claim 2 wherein the herbicide is water-soluble.

69. The composition of claim 2 wherein the herbicide is a salt of glyphosate or glufosinate.

70. The composition of claim 2 wherein the herbicide is a water-soluble salt of glyphosate.

71. The composition of claim 70 wherein the salt is an alkali metal, ammonium, $C_{1-16}$ alkylammonium, $C_{1-16}$ alkanolammonium or $C_{1-16}$ alkylsulfonium salt.

72. The composition of claim 70 wherein the salt is a sodium, ammonium, dimethylammonium, isopropylammonium, monoethanolammonium or trimethylsulfonium salt.

73. The composition of claim 13 wherein the herbicide is a foliar-applied herbicide selected from aminotriazole, asulam, bentazon, bialaphos, bipyridyl herbicides, bromacil, clopyralid, cyclohexenone herbicides, diphenylether herbicides, fosamine, glufosinate, glyphosate, hydroxybenzonitrile herbicides, imidazolinone herbicides, isoxaben, phenoxy herbicides, phenoxypropionate herbicides, picloram, substituted urea herbicides, sulfonylurea herbicides and triazine herbicides.

74. The composition of claim 13 wherein the herbicide is N-phosphonomethylglycine, a salt or ester thereof, or a compound which is converted to N-phosphonomethylglycine in plant tissues or which otherwise provides N-phosphonomethylglycine in ionic form.

75. The composition of claim 13 wherein the herbicide is water-soluble.

76. The composition of claim 13 wherein the herbicide is a salt of glyphosate or glufosinate.

77. The composition of claim 13 wherein the herbicide is a water-soluble salt of glyphosate.

78. The composition of claim 77 wherein the salt is an alkali metal, ammonium, $C_{1-16}$ alkylammonium, $C_{1-16}$ alkanolammonium or $C_{1-16}$ alkylsulfonium salt.

79. The composition of claim 78 wherein the salt is a sodium, ammonium, dimethylammonium, isopropylammonium, monoethanolammonium or trimethylsulfonium salt.

80. The process of claim 52 wherein the herbicide is a foliar-applied herbicide selected from aminotriazole, asulam, bentazon, bialaphos, bipyridyl herbicides, bromacil, clopyralid, cyclohexenone herbicides, diphenylether herbicides, fosamine, glufosinate, glyphosate, hydroxybenzonitrile herbicides, imidazolinone herbicides, isoxaben, phenoxy herbicides, phenoxypropionate herbicides, picloram, substituted urea herbicides, sulfonylurea herbicides and triazine herbicides.

81. The process of claim 52 wherein the herbicide is N-phosphonomethylglycine, a salt or ester thereof, or a compound which is converted to N-phosphonomethylglycine in plant tissues or which otherwise provides N-phosphonomethylglycine in ionic form.

82. The process of claim 52 wherein the herbicide is water-soluble.

83. The process of claim 52 wherein the herbicide is a salt of glyphosate or glufosinate.

84. The process of claim 52 wherein the herbicide is a water-soluble salt of glyphosate.

85. The process of claim 84 wherein the salt is an alkali metal, ammonium, $C_{1-16}$ alkylammonium, $C_{1-16}$ alkanolammonium or $C_{1-16}$ alkylsulfonium salt.

86. The process of claim 84 wherein the salt is a sodium, ammonium, dimethylammonium, isopropylammonium, monoethanolammonium or trimethylsulfonium salt.

* * * * *

UNITED STATES PATENT AND TRADEMARK OFFICE
CERTIFICATE OF CORRECTION

PATENT NO. : 6,020,287
DATED : February 1, 2000
INVENTOR(S) : Ronald J. Brinker, Jane L. Gillespie, Peter J. Raymond, Joseph J. Sandbrink, James M. Warner, Al S. Wideman, and Daniel R. Wright It is certified that error appears in the above-identified patent and that said Letters Patent is hereby corrected as shown below:

Column 64, claim 7,
Line 32, replace "$R_S$" with -- $R^5$ --

Column 69, claim 33,
Line 28, replace "cc-methyl-trans-cinnamaldehyde" with -- α-methyl-trans-cinnamaldehyde --.

Column 71, claim 54,
Line 33, replace "(11)" with -- (II) --.

Column 74, claim 65,
Line 20, replace "about g/ha." with -- about 25 g/ha. --.

Column 74, claim 66,
Line 25, replace "gIlyphosate" with -- glyphosate --.

Signed and Sealed this

Twenty-sixth Day of March, 2002

Attest:

*Attesting Officer*

JAMES E. ROGAN
*Director of the United States Patent and Trademark Office*